US011530388B2

(12) United States Patent
Soto-Gutierrez et al.

(10) Patent No.: US 11,530,388 B2
(45) Date of Patent: Dec. 20, 2022

(54) METHODS OF ENGINEERING HUMAN INDUCED PLURIPOTENT STEM CELLS TO PRODUCE LIVER TISSUE

(71) Applicant: University of Pittsburgh—Of the Commonwealth System of Higher Education, Pittsburgh, PA (US)

(72) Inventors: Alejandro Soto-Gutierrez, Pittsburgh, PA (US); Tomoji Mashimo, Osaka (JP); Alexandra Sylvie Collin de l'Hortet, Pittsburgh, PA (US); Eduardo Cervantes Alvarez, Huixquilucan (MX); Jorge Guzman Lepe, Pittsburgh, PA (US); Kan Handa, Pittsburgh, PA (US); Kazuki Takeishi, Pittsburgh, PA (US); Yang Wang, Pittsburgh, PA (US); Branimir Popovic, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 413 days.

(21) Appl. No.: 16/485,771

(22) PCT Filed: Feb. 13, 2018

(86) PCT No.: PCT/US2018/018032
§ 371 (c)(1),
(2) Date: Aug. 13, 2019

(87) PCT Pub. No.: WO2018/152120
PCT Pub. Date: Aug. 23, 2018

(65) Prior Publication Data
US 2019/0376029 A1    Dec. 12, 2019

Related U.S. Application Data

(60) Provisional application No. 62/459,003, filed on Feb. 14, 2017.

(51) Int. Cl.
| C12N 5/00 | (2006.01) |
| C12N 5/071 | (2010.01) |
| A01K 67/027 | (2006.01) |
| C12N 5/074 | (2010.01) |

(52) U.S. Cl.
CPC .......... *C12N 5/067* (2013.01); *A01K 67/0271* (2013.01); *C12N 5/0696* (2013.01); *A01K 2207/12* (2013.01); *A01K 2217/075* (2013.01); *A01K 2227/105* (2013.01); *A01K 2267/025* (2013.01); *C12N 2501/115* (2013.01); *C12N 2501/12* (2013.01); *C12N 2501/155* (2013.01); *C12N 2506/45* (2013.01)

(58) Field of Classification Search
None
See application file for complete search history.

(56) References Cited

U.S. PATENT DOCUMENTS

| 9,914,939 B2 * | 3/2018 | Church ............... C12N 5/0696 |
| 2013/0259836 A1 | 10/2013 | Lee et al. |
| 2014/0141509 A1 * | 5/2014 | Gadue .................. C12N 5/0672 435/357 |
| 2016/0256672 A1 | 9/2016 | Arumugaswami et al. |
| 2016/0272937 A1 | 9/2016 | Lam et al. |

FOREIGN PATENT DOCUMENTS

| CN | 106119284 A | 11/2016 |
| EP | 2 495 320 A1 | 9/2012 |
| JP | 2007-228962 A | 9/2007 |
| JP | 2011-519580 A | 7/2011 |
| JP | 2013-535980 A | 9/2013 |
| JP | 2014-525248 A | 9/2014 |
| JP | 2016-515401 A | 5/2016 |
| JP | 2016-521709 A | 7/2016 |
| JP | 2016-198110 A | 12/2016 |
| WO | WO 2008/151283 A1 | 12/2008 |
| WO | WO 2009/151844 A1 | 12/2009 |
| WO | WO 2011/146862 A1 | 11/2011 |
| WO | WO 2012/025725 A1 | 3/2012 |
| WO | WO 2013/032918 A1 | 3/2013 |
| WO | WO 2014/124527 A1 | 8/2014 |
| WO | WO 2014/172489 A2 | 10/2014 |
| WO | WO 2014/197638 A2 | 12/2014 |
| WO | WO 2015/088643 A1 | 6/2015 |
| WO | WO 2016/131959 A1 | 8/2016 |

OTHER PUBLICATIONS

Tafaleng (Hepatology, 2015, vol. 62, p. 147-157).*
Rodriguez-Burford (Biotechinic & Histochemistry, 2003, vol. 78, No. 1, p. 17-21).*
Na (Annals of Surgical Treatment and Res., 2014, vol. 87, No. 2, p. 53-60).*
Sun (World J Gastroenterology, 2015, vol. 21, No. 39, p. 11118-11126).*
Podda (Digestive diseases and Sciences, 1989 Supplement, vol. 34, No. 12, p. 59S-65S).*
Koga (Kanzo, 1987, vol. 28, vol. 12, p. 1597-1604; English abstract only).*
Koga (Kanzo, 1987, vol. 28, vol. 12, p. 1597-1604).*
Gibco manual for "chemically defined lipid concentrate" (2014).*
Imaoka (Drug Metab Dispos, 2013, vol. 41, p. 1442-1449).*
He (Am. J. Pathology, 2010, vol. 177, No. 3, p. 1311-1319).*
Laconi (Am. J. Path., 1998, vol. 153, No. 1, p. 319-329).*

(Continued)

*Primary Examiner* — Michael C Wilson
(74) *Attorney, Agent, or Firm* — Klarquist Sparkman, LLP

(57) ABSTRACT

Methods are disclosed herein for producing human hepatocytes from human induced pluripotent stem cells. Also provided are transgenic rats for the expansion of human hepatocytes, such as those produced using the methods disclosed herein.

40 Claims, 27 Drawing Sheets

Specification includes a Sequence Listing.

(56) References Cited

OTHER PUBLICATIONS

Song et al., "Efficient generation of hepatocyte-like cells from human induced pluripotent stem cells," *Cell Research* 19: 1233-1242 (ePUB Sep. 8, 2009).
Efthymiou et al., "Self-renewal and cell lineage differentiation strategies in human embryonic stem cells and induced pluripotent stem cells," *Expert Opinion on Biological Therapy* 14(9): 1744-7682 (e-PUB May 31, 2014).
Fegan et al., "Chemically controlled protein assembly: techniques and applications," *Chemical Reviews* 110(6): 3315-3336 (Jun. 9, 2010).
Azuma et al., "Robust expansion of human hepatocytes in $Fah^{-/-}/Rag2^{-/-}/Il2rg^{-/-}$ mice," *Nature Biotechnology* 25: 903-910 (2007)(Abstract).
Hannoun et al., "The potential of induced pluripotent stem cell derived hepatocytes," *Journal of Hepatology* 65: 182-199 (2016).
He et al., "Liver xeno-repopulation with human hepatocytes in $Fah^{-/-}Rag2^{-/-}$ mice after pharmacological immunosuppression," *American Journal of Pathology* 177(3): 1311-1319 (Sep. 2010).
International Search Report and Written Opinion from patent PCT Application No. PCT/US2018/018032, 11 pages (dated May 15, 2018).
Si-Tayeb et al., "Highly efficient generation of human hepatocyte-like cells from induced pluripotent stem cells," *Hepatology* 51(1): 297-305 (Jan. 2010).
Tafaleng et al., "Induced pluripotent stem cells model personalized variations in liver disease resulting from a1-antitrypsin deficiency," *Hepatology* 62(1): 147-157 (Jul. 2015).
Takebe et al., "Vascularized and functional human liver from an iPSC-derived organ bud transplant," *Nature* 499: 481-484 (Jul. 25, 2013)(Abstract).
Buehr et al., Capture of authentic embryonic stem cells from rat blastocycsts, Cell 135: 1287-1298 (Dec. 26, 2008).

\* cited by examiner

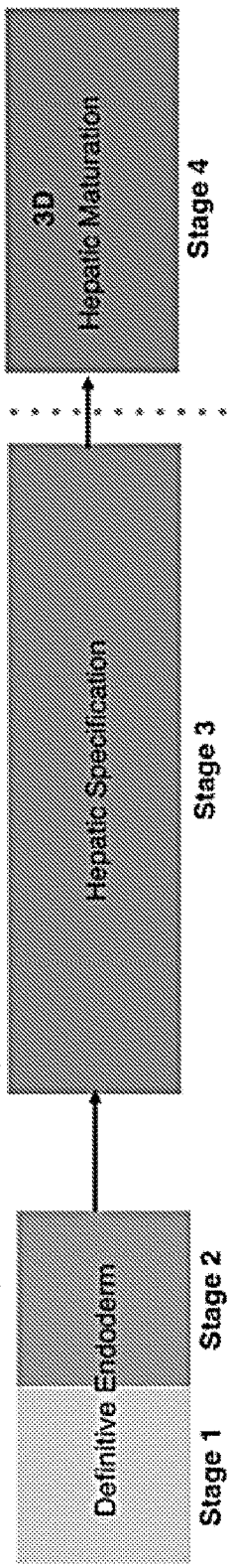
FIG. 2 Design of Hepatic Maturation of Human iPS-cell
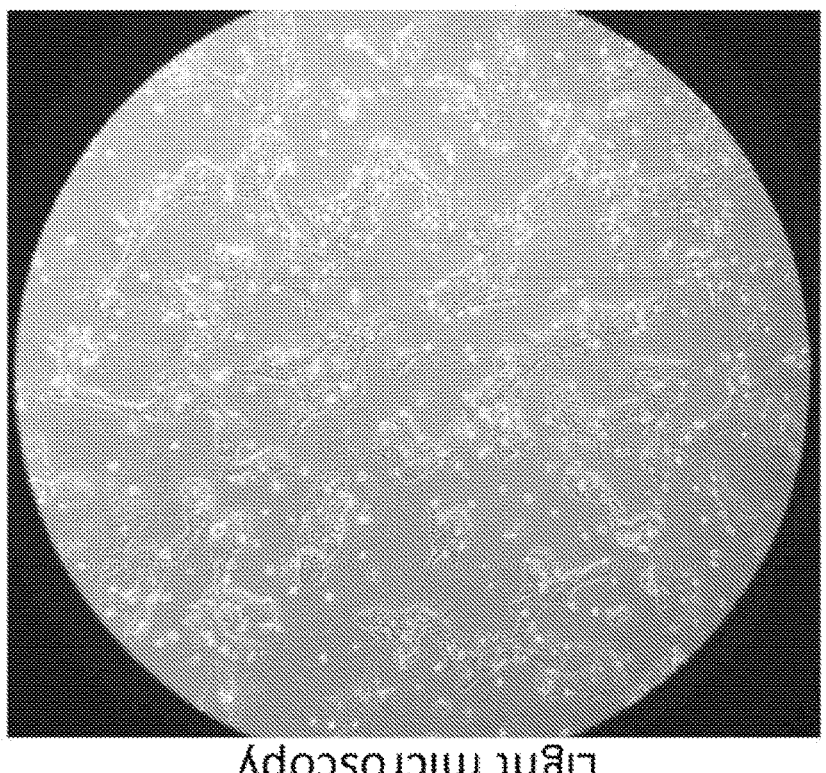
FIG. 3 Light microscopy

FIG. 14

| Virus | target | Cp Target | | Cp Reference (topoisomerase I (TOP1)) | |
|---|---|---|---|---|---|
| | | MW | Stdev | MW | Stdev |
| pEAlb123-iCasp9_IRES_GFP | Casp9 | 22,49 | 0,03 | 21,51 | 0,02 |
| pcDNA3-CMV-eGFP | | no product | 0,00 | 21,59 | 0,04 |
| pEAlb123-iCasp9_IRES_GFP | eGFP | 22,33 | 0,00 | 21,51 | 0,02 |
| pcDNA3-CMV-eGFP | | 18,24 | 0,01 | 21,59 | 0,04 |

FIG. 15A

```
                 PAM         gRNA-Il2rg
F344   wt   AGCCGACCAACCTCACTATGCACTATAGGTATGAG
No.1   -4   AGCCGACCAACC----TATGCACTATAGGTATGAG
No.2   -27  AGCA--(Δ27bp)--CTATGCACTATAGGTATGAG
       -5   AGCCGACCAAC-----TATGCACTATAGGTATGAG
No.3   +1   AGCCGACCAACCTTCACTATGCACTATAGGTATGAG
       -4   AGCCGACCAACC----TATGCACTATAGGTATGAG
No.4   +1   AGCCGACCAACCTTCACTATGCACTATAGGTATGAG
       -4   AGCCGACCAACC----TATGCACTATAGGTATGAG
No.5   -5   AGCCGACCAAC-----TATGCACTATAGGTATGAG
No.6   -5   AGCCGACCAAC-----TATGCACTATAGGTATGAG
No.7   -5   AGCCGACCAAC-----TATGCACTATAGGTATGAG
No.8   -9   AGCCGAC---------TATGCACTATAGGTATGAG
```

FIG. 15B

```
                 PAM         gRNA-Rag2
F344   wt   TACCTCCCACCTCTTCGTTACCCAGCTACTTGC
No.2   -18  TACCTCCC------------------TACTTGC
No.12  +2   TACCTCCCAGGCCTCTTCGTTACCCAGCTACTTGC
```

FIG. 16

Transplantation of Human Fetal Hepatocytes and Human iPS-Derived Hepatocytes (Alex Protocol) in Rats

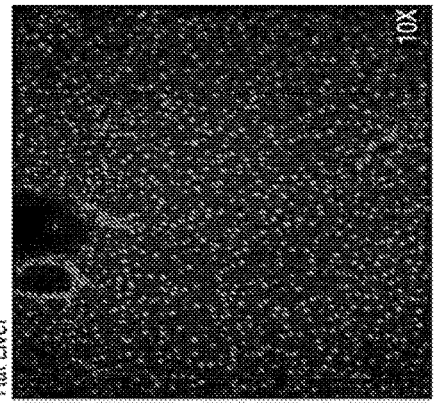
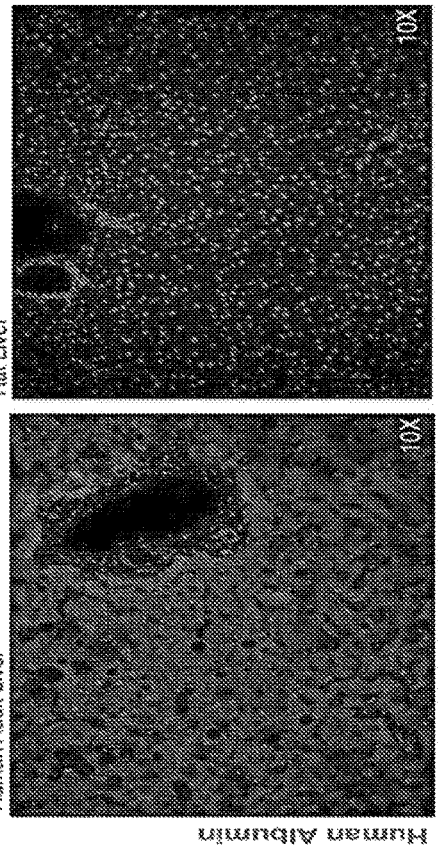
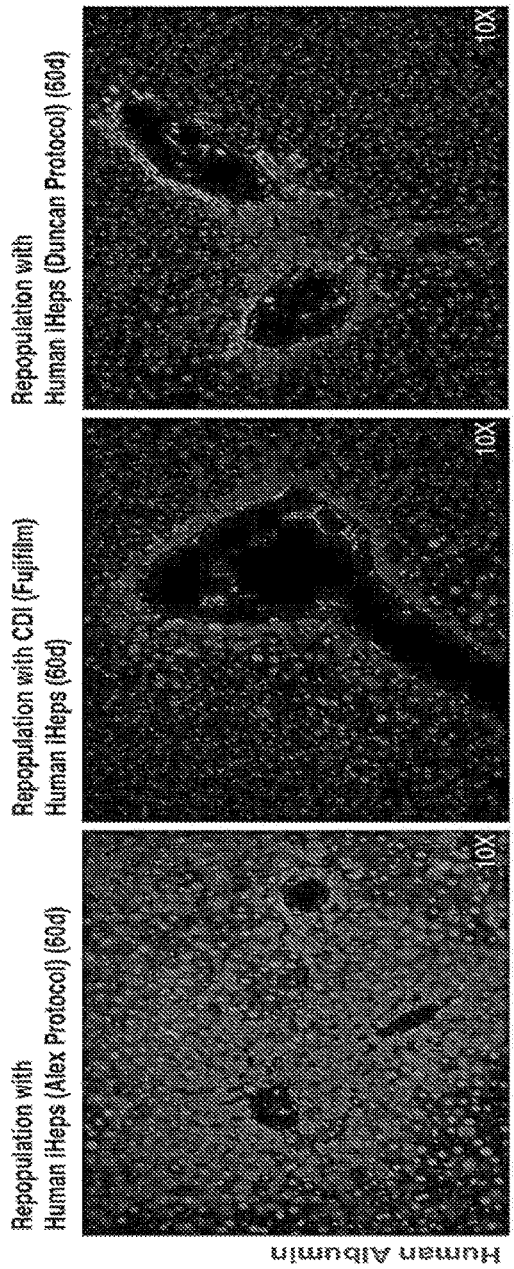
FIG. 18

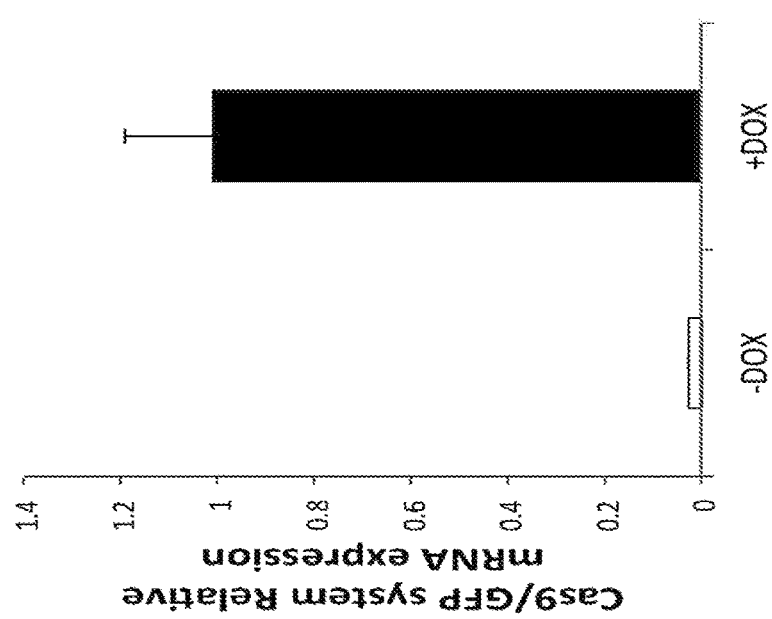
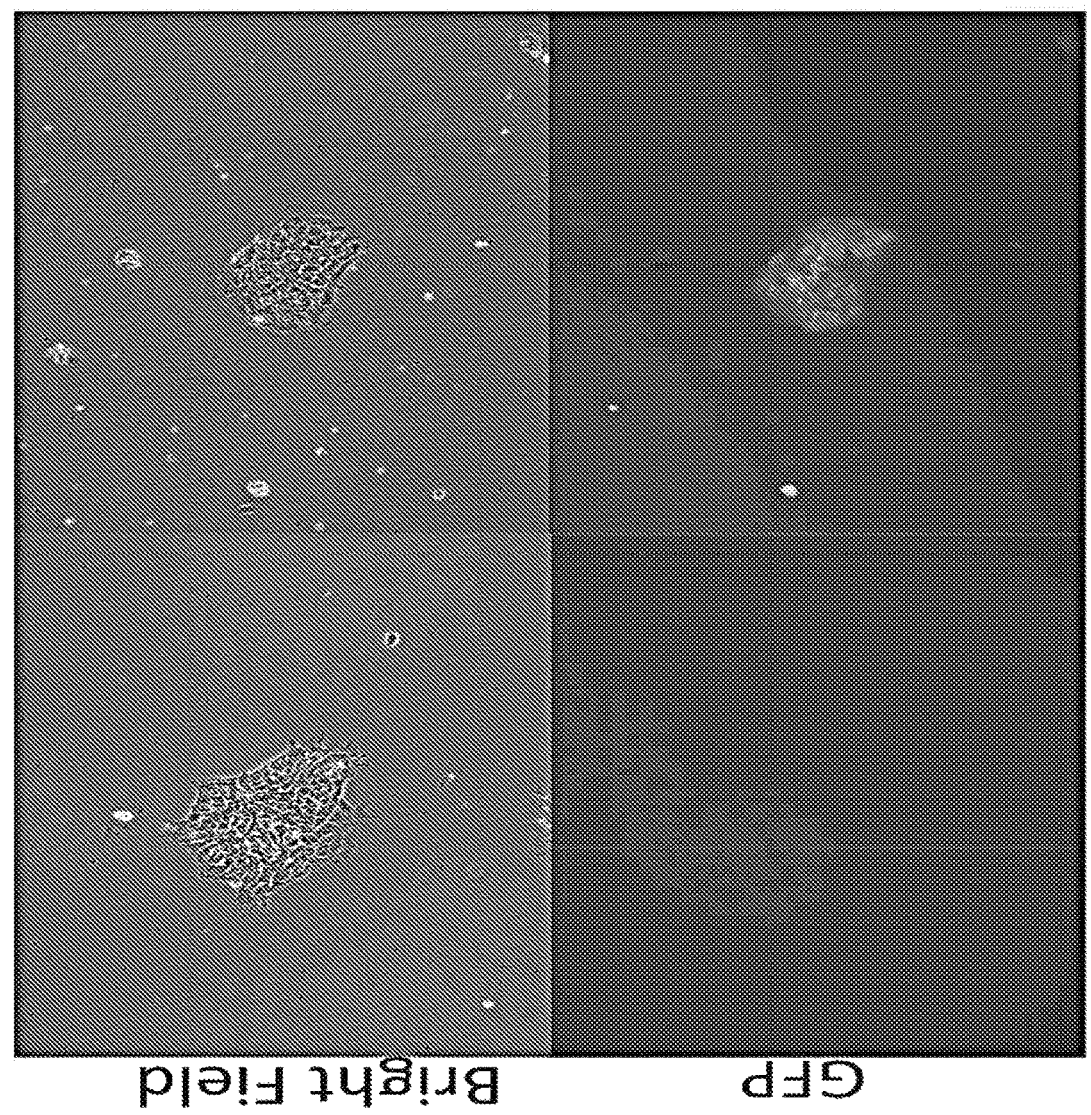

METHODS OF ENGINEERING HUMAN INDUCED PLURIPOTENT STEM CELLS TO PRODUCE LIVER TISSUE

CROSS REFERENCE TO RELATED APPLICATIONS

This is a § 371 U.S. national stage of International Application No. PCT/US2018/018032, filed Feb. 13, 2018, which was published in English under PCT Article 21(2), and which claims the benefit of U.S. Provisional Application No. 62/459,003, filed Feb. 14, 2017, which is herein incorporated by reference in its entirety

ACKNOWLEDGMENT OF GOVERNMENT SUPPORT

This invention was made with government support under grant no. DK099257 awarded by the National Institutes of Health. The government has certain rights in the invention.

FIELD

This relates to the field of stem cells, specifically to methods for producing human hepatocytes from induced pluripotent stem cells.

BACKGROUND

Liver transplantation is the only curative therapy for severe end-stage liver disease, either using a partial liver from a living or cadaveric donor or a whole cadaveric liver. Only a third of the individuals on the liver transplant waiting list will be transplanted and the demand for livers is projected to increase 23% in the next 20 years. Organ availability is a constraint on the number of liver transplants that can be performed.

Human induced pluripotent stem cells (iPSCs) have the capability of revolutionizing research and therapy of liver diseases by providing a source of hepatocytes for autologous cell/engineered liver therapy and disease modeling. However, despite progress in advancing the differentiation of human iPSCs into hepatocytes (iPSC-Heps) in vitro, cells that replicate the ability of human primary adult hepatocytes to proliferate and completely replace livers in vivo that generates sufficient cell numbers for clinical applications has not been achieved. Furthermore, protocols for directing differentiation of iPSCs into hepatocytes usually resulted in immature phenotype with suboptimal hepatic function. These deficiencies have hampered efforts to recreate human liver diseases in rodents, and have cause skepticism on the clinical potential of iPSC-Heps. Liver repopulation and engineered liver tissue are best suited to the task if an unlimited availability of functional induced Pluripotent Stem Cells-derived hepatocytes (iPS-Heps) can be accomplished. Creating an immediately available and inexhaustible supply of functioning liver cells from autologous tissue allows early intervention in patients with hepatic failure. Combined with recent advances in genome editing technology, such liver cells could be used widely to treat devastating liver based inborn errors of metabolism and eliminates the need for a life-long regimen of immune-suppressive drugs and their complications. Thus an effective system to ensure the production of human iPSC-Heps with function and regeneration-responsiveness identical to normal adult hepatocytes in clinically relevant numbers is needed.

SUMMARY

In one embodiment, a method is disclosed herein for producing human hepatocytes. The method includes a) culturing human induced pluripotent stem cells (iPSC) in a first medium comprising an effective amount of activin A, fibroblast growth factor (FGF)-2 and bone morphogenic protein (BMP)-4 for about 2 to about 3 days, to produce mesendoderm cells; b) culturing the mesendoderm cells in a second medium comprising an effective amount of activin A, and in the absence of FGF-2 and BMP-4, for about 2 to about 3 days, to produce definitive endoderm cells; c) culturing the definitive endoderm in a third medium comprising an effective amount of dimethyl sulfoxide (DMSO), and hepatocyte growth factor (HGF), wherein the medium is a low glucose medium for about eight to about 14 days, to produce hepatic progenitor cells; and d) culturing the hepatic progenitor cells in a fourth medium comprising an effective amount of HGF, urso deoxycholic acid, cholesterol, palmitic acid, oleic acid, rifampicin, and wherein the fourth medium is a low glucose medium, to produce human hepatocytes. The method also can include expanding the human hepatocytes in an immunocompromised animal.

In another embodiment, a method is disclosed for producing human hepatocytes, including: a) culturing human induced pluripotent stem cells (iPSC) in a first medium comprising an effective amount of activin A, fibroblast growth factor (FGF)-2 and bone morphogenic protein (BMP)-4 for about 2 to about 3 days, to produce mesendoderm cells; b) culturing the mesendoderm cells in a second medium comprising an effective amount of activin A, and in the absence of FGF-2 and BMP-4, for about 2 to about 3 days, to produce definitive endoderm cells; c) culturing the definitive endoderm in a third medium comprising an effective amount of dimethyl sulfoxide (DMSO), and hepatocyte growth factor (HGF), wherein the medium is a low glucose medium (0.2 to 2 grams/liter glucose) for about eight to about 14 days, to produce hepatic progenitor cells; d) transplanting the hepatic progenitor cells into a liver of an immunocompromised non-human transgenic animal; and e) harvesting hepatocytes from the liver of the immunocompromised non-human transgenic animal. In one specific non-limiting example, the transgenic animal is a Rag2$^{-/-}$ Il2rg$^{-/-}$ rat harboring an inducible Casp9 transgene that is expressed in hepatocytes.

In yet another embodiment, disclosed is a transgenic rat, wherein the transgenic rat is a Rag2$^{-/-}$ Il2rg$^{-/-}$ rat harboring a transgene comprising a promoter expressed in the liver, such as an albumin or transthyretin promoter and/or alpha-1-antitrypsin promoter, operably linked to a nucleic acid molecule encoding a fusion protein, wherein the fusion protein comprises FKBP12 and caspase 9, and wherein human hepatocytes can be expanded in the liver of the transgenic rat.

The foregoing and other objects, features, and advantages of the invention will become more apparent from the following detailed description, which proceeds with reference to the accompanying figures.

BRIEF DESCRIPTION OF THE DRAWINGS

FIG. 2 Schematic representation of one method of hepatic differentiation using human iPSC. Defined medium is added on the cells sequentially to initiate definitive endoderm (Stage 1 and 2), to induce hepatic specification (Stage 3). At the end of stage 3, iHeps cells are detached and size-sorted to be replated. A defined medium to induce hepatic maturation is added on the cells (Stage 4).

FIG. 3 Light microscopic picture of hIPSC one day after single cell passage.

FIG. 14 Both plasmid encoded genes (iCASP9 and eGFP) are well expressed in transfected H4-II-E-C3 cells.

FIGS. 15A-15B Sequencing assay for CRISPR-mediated mutations at the target sequences for Il2rg (A) and Rag2 (B) gene. Multiple deletions and insertions are depicted by dashes and letters, respectively, and are aligned along the WT sequences (SEQ ID NO: 34 and 35) shown on the top line. SEQ ID NOs: 34 and 36-46 are shown in FIG. 15A and SEQ ID NOs: 35 and 47-48 are shown in FIG. 15B.

FIG. 16 Transplantation of human fetal hepatocytes (21 weeks old) and human iHeps (presently disclosed methods) after 30 d demonstrated engraftment and the presence of large colonies of repopulating human hepatocytes as shown by the expression of specific human albumin. Moreover, similar levels of genomic DNA for the HNF4 gene was detected in the transplanted livers after 30 d.

FIG. 18 Immunohistochemistry analysis of XSCID rat livers retrorsine/hepatectomy pretreated and transplanted with human iHeps with either the present methods (presently disclosed methods), Duncan's protocol and commercially available human iPS-hepatocytes (CDI, Fujifilm).

FIGS. 19A-19B hiPS-tet-On-Cas9/GFP characterization. A) Bright field and fluorescent microscopy of hiPS-Tet-On-Cas9/GFP cells with and without doxycycline. B) Cas9/GFP system relative expression in hiPs-Tet-On-Cas9/GFP cells with and without doxycycline assessed by means of RTqPCR.

100 um. (B) A graph of the percentage of BrdU labeled cells is provided. Three different areas and at least 100 nuclei per area positive for BrdU immunofluorescence were quantified.

Figure 24A:
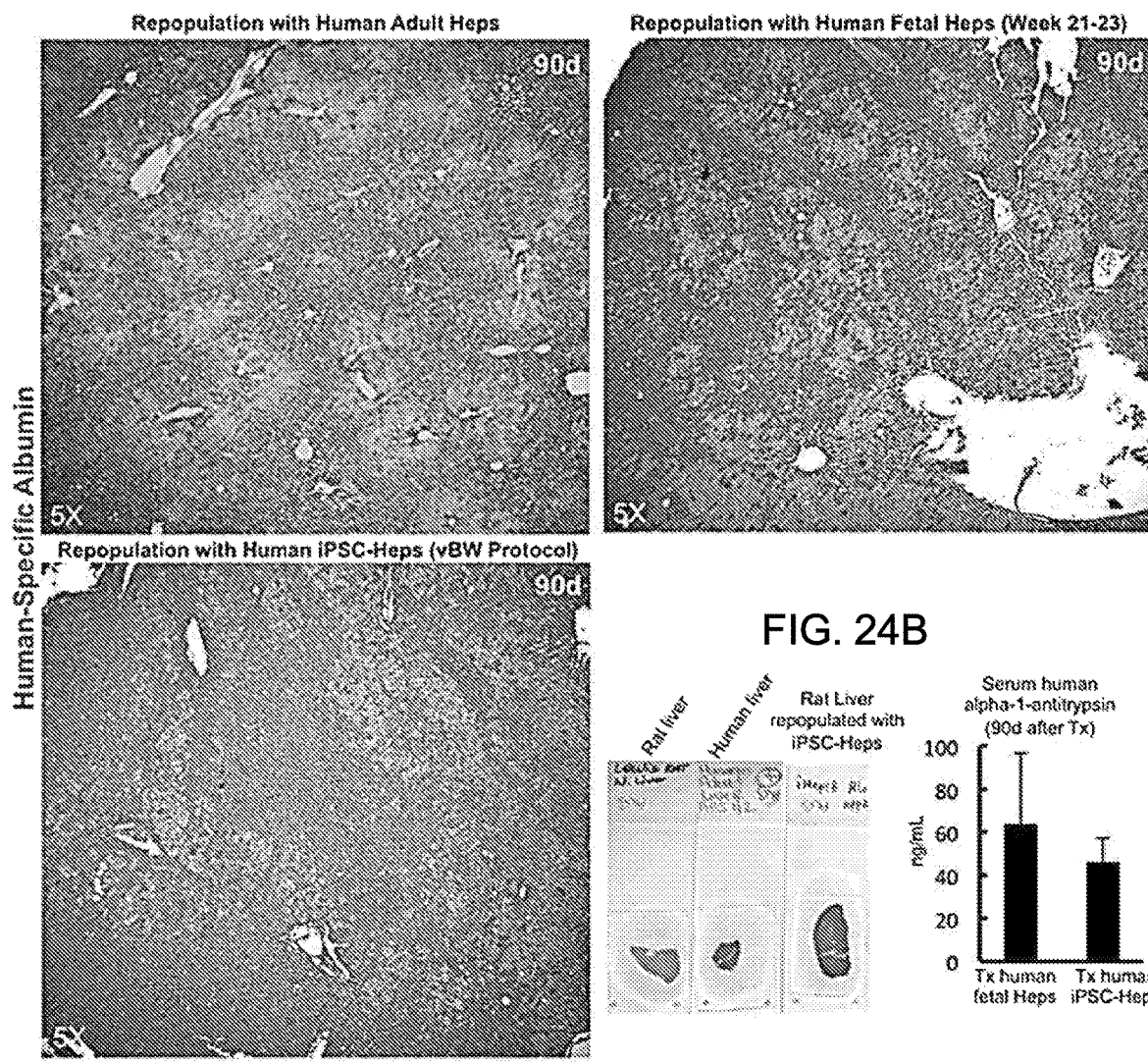
Figure 24B:
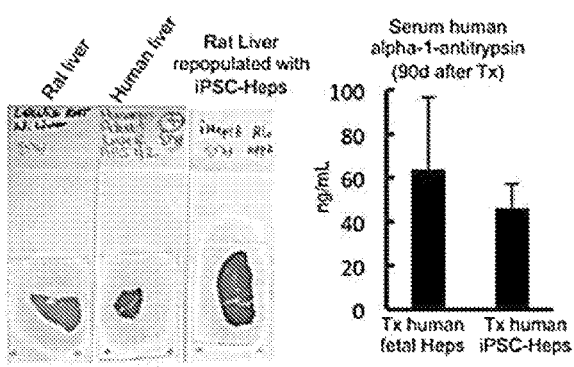

FIG. 24A-24B. Robust liver repopulation in immunocompromised-rats with human adult, fetal hepatocytes and iPSC-Heps. (A) Rats-animals were transplanted with either human adult hepatocytes (n=25), fetal hepatocytes (n=23) or human iPSC-Heps (disclosed-protocol). At 90d nearly 80% or the liver was replaced by human adult or fetal hepatocytes and nearly 70% of the liver was replaced by human iPSC-Heps (disclosed-protocol) as shown by immunohistochemistry of human specific albumin. (B) Enzyme-linked immunosorbent assay for human alpha 1 antitrypsin measurement at 90 d after transplantation corroborated the presence of human hepatocytes within the rat livers. Serum was analyzed for alpha 1 antitrypsin via ELISA (n=4, each experimental group).

Figure 25A:
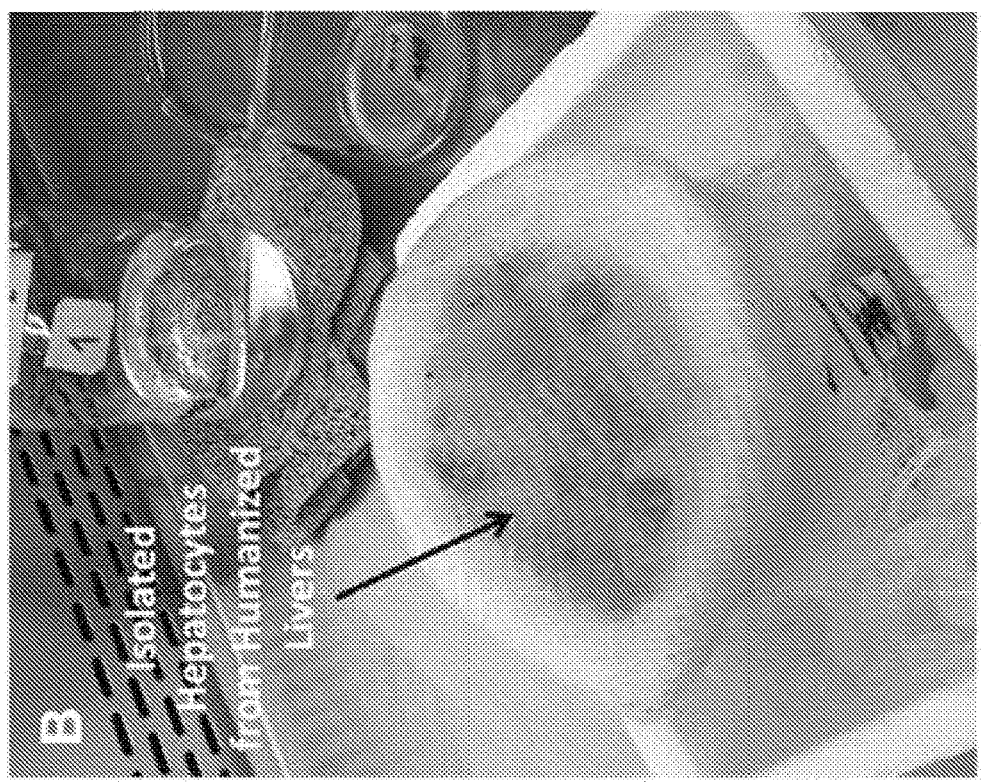
Figure 25B:
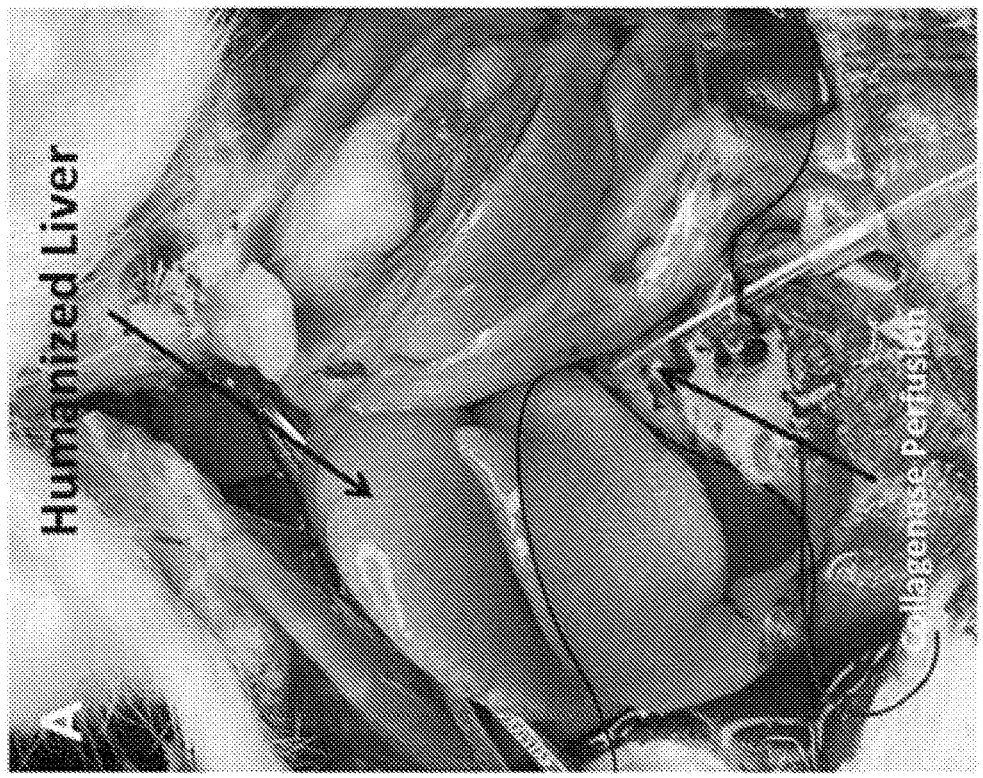

FIGS. 25A-25B. Isolation of humanized livers from rats. (A) Rat liver is perfused with a collagenase solution to produce single cells. (B) Digested livers are filtered and centrifuged to purify only hepatocytes.

Figure 26A:
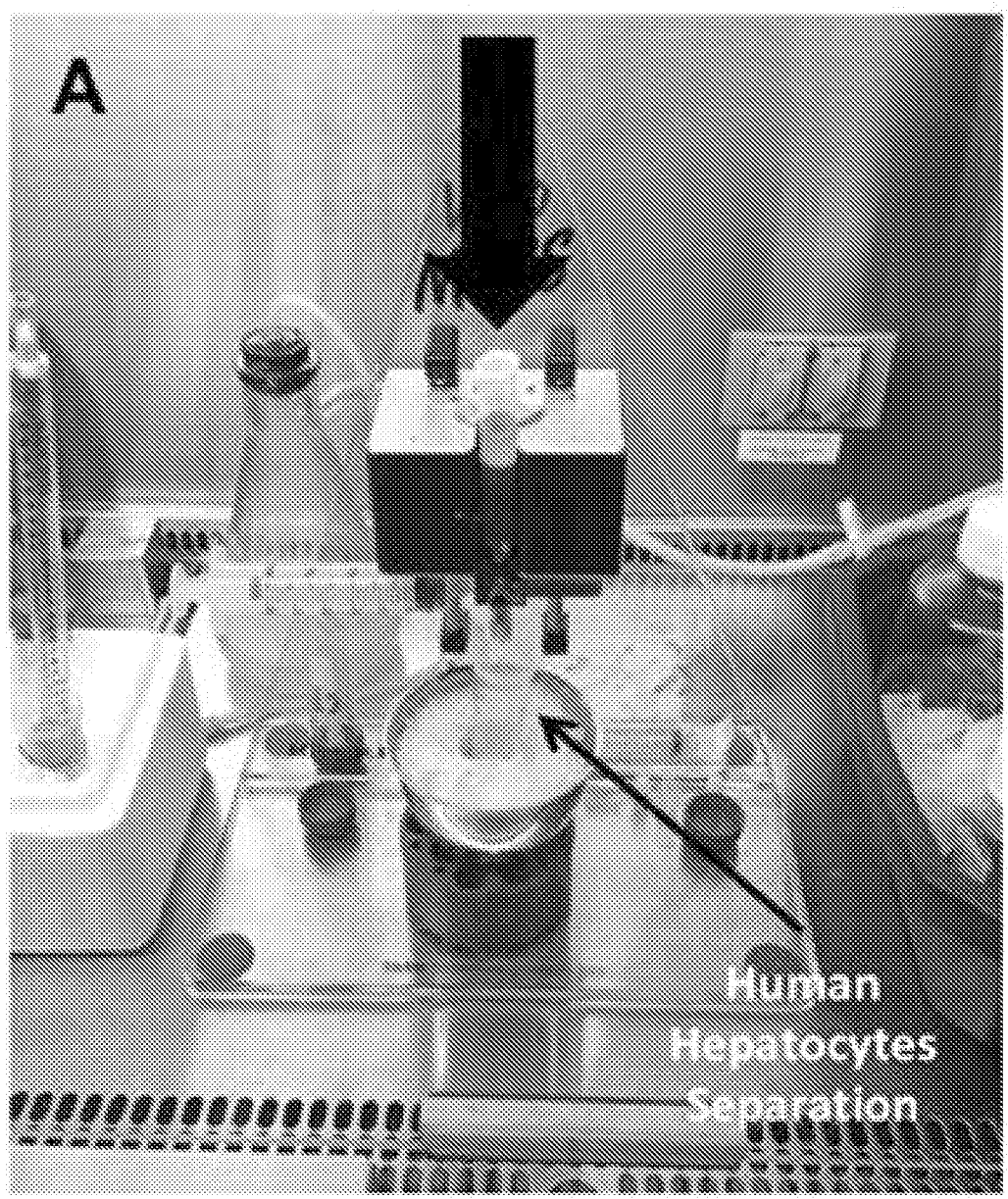
Figure 26B:
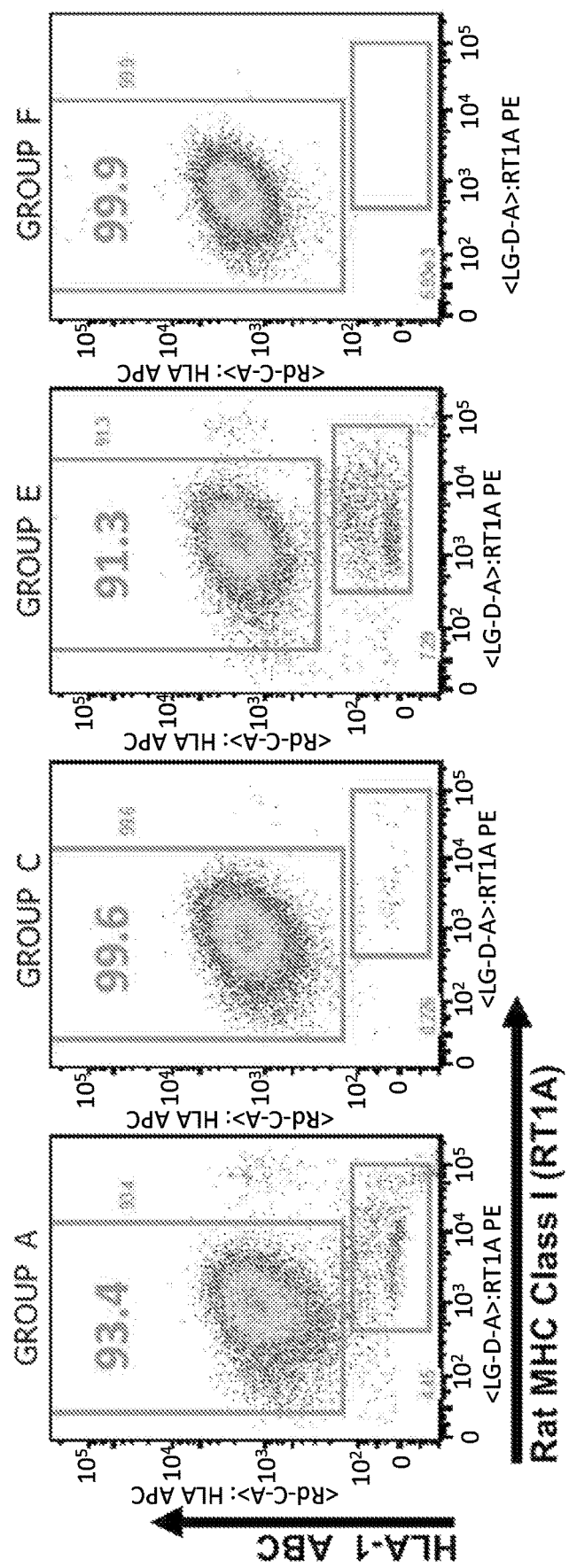

FIG. 26A-26B. Human hepatocytes magnetic-based purification. (A) The resulting single cell suspension is labeled with rat specific antibodies containing magnetic microbeads for rat cell depletion using magnetic-activated cell sorting. (B) Resulting cell suspensions can be immunomagnetically labeled using an antibody for rat MHC class 1 (RT1A) (Miltenyi Biotec). The cells were then sorted on a MACS column (Miltenyi Biotec) into positive and negative fractions. Different protocols wherein the antibody concentration and magnetic columns were varied (Group A-F) were tested and optimized for high human cell enrichment reaching up to 99.9% of human cells in the best optimized protocol in the collected negative cell fractions as shown by FACS analysis.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [Sequence_Listing, Aug. 13, 2019, 68.0 KB], which is incorporated by reference herein.

DETAILED DESCRIPTION

The ability to functionally repopulate immunodeficient mice has become the benchmark for having generated a hepatocyte vs a hepatocyte-like cell that is incapable of liver repopulation. Previously, only limited engraftment of stem cell-derived human hepatocyte-like cells has been reported. Disclosed herein are efficient hepatic differentiation protocols that utilize human induced pluripotent cells to produce hepatocytes and hepatocyte progenitor cells that can repopulate the liver in an immunocompromised animal. Also disclosed is the development of an immune compromised rat model where hepatocytes can engraft, expand, and repopulate the livers of these rats.

Using the disclosed methods, human hepatocytes can be produced as a preclinical step for the treatment of liver failure by autologous transplantation. Moreover, also disclosed is the engineering of human iPS cells including a heterologous nucleic acid, such as but not limited to, a doxycline promoter operably linked to a nucleic acid encoding Cas9 or shRNA. These cells can then be used to target in any gene of interest by introducing nucleic acids encoding sgRNAs or to down regulate any gene of interest after transplantation and liver repopulation (See, for example, FIG. 1).

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Activin: Members of the transforming growth factor beta (TGF-beta) superfamily which participate in regulation of several biological processes, including cell differentiation and proliferation. Activin A is a member of this family that mediates its biological effects through a complex of trans-membrane receptor serine/threonine kinases, and binds to specific Activin A receptors. It is a dimer composed of two subunits. Activin A participates in regulation of stem cell maintenance, via SMAD-dependent activation transcription of marker of pluripotency like POU class 5 homeobox 1 (Oct-3/4), nanog, nodal, and nodal-signaling regulators, Left-right determination factor 1 and 2 (Lefty-B and Lefty-A). Activin A also stimulates transcription of several hormones such as Gonadotropin-releasing hormone. An exemplary sequence for Activin A is provided in GENBANK® Accession No. NM_002192, as available on Jan. 20, 2017, incorporated herein by reference.

Alter: A change in an effective amount of a substance or parameter of interest, such as a polynucleotide, polypeptide or a property of a cell. An alteration in polypeptide or polynucleotide or enzymatic activity can affect a physiological property of a cell, such as the differentiation, proliferation, or senescence of the cell. The amount of the substance can be changed by a difference in the amount of the substance produced, by a difference in the amount of the substance that has a desired function, or by a difference in the activation of the substance. The change can be an increase or a decrease. The alteration can be in vivo or in vitro. In several embodiments, altering is at least about a 50%, 60%, 70%, 80%, 90%, 95%, 96%, 97%, 98%, 99%, or 100% increase or decrease in the effective amount (level) of a substance, the proliferation and/or survival of a cells, or the activity of a protein, such as an enzyme.

Animal: Living multi-cellular vertebrate organisms, a category that includes, for example, mammals and birds. The term mammal includes both human and non-human mammals. Similarly, the term "subject" includes both human and veterinary subjects.

Biological sample or sample: A sample obtained from cells, tissue or bodily fluid of a subject, such as peripheral blood, serum, plasma, cerebrospinal fluid, bone marrow, urine, saliva, tissue biopsy, surgical specimen, and autopsy material.

Bone Morphogenic Proteins (BMPs): A family of proteins, identified originally in extracts of demineralized bone that were capable of inducing bone formation at ectopic sites.

BMPs are found in minute amounts in bone material (approximately 1 microgram/kg dry weight of bone). Most members of this family (with the exception of BMP-1) belong to the transforming growth factor-β family of proteins.

BMPs can be isolated from demineralized bones and osteosarcoma cells. They have been shown also to be expressed in a variety of epithelial and mesenchymal tissues in the embryo. BMPs are proteins which act to induce the differentiation of mesenchymal-type cells into chondrocytes and osteoblasts before initiating bone formation. They promote the differentiation of cartilage- and bone-forming cells near sites of fractures but also at ectopic locations. Some of the proteins induce the synthesis of alkaline phosphatase and collagen in osteoblasts. Some BMPs act directly on osteoblasts and promote their maturation while at the same time suppressing myogenous differentiation. Other BMPs promote the conversion of typical fibroblasts into chondrocytes and are capable also of inducing the expression of an osteoblast phenotype in non-osteogenic cell types. BMPs include BMP-1 to BMP-15, such as BMP-2 and BMP-4. BMP-2 and BMP-4 and BMP-7 have been shown to promote bone formation. BMP2/4 is a hybrid gene in which the secretion signal of BMP4 is replaced with that of BMP2 (see Peng et al., *Mol. Therapy* 4:95-104, 2001, incorporated herein by reference). An exemplary amino aid sequence for BMP-1 is provided in GENBANK® Accession No. KR709446.1, as available on Feb. 11, 2017, incorporated herein by reference.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Cirrhosis: Refers to a group of chronic liver diseases characterized by loss of the normal microscopic lobular architecture and regenerative replacement of necrotic parenchymal tissue with fibrous bands of connective tissue that eventually constrict and partition the organ into irregular nodules. Cirrhosis has a lengthy latent period, usually followed by sudden abdominal pain and swelling with hematemesis, dependent edema, or jaundice. In advanced stages there may be ascites, pronounced jaundice, portal hypertension, varicose veins and central nervous system disorders that may end in hepatic coma.

Collecting: As used herein, "collecting" expanded human hepatocytes refers to the process of removing the expanded hepatocytes from a mouse that has been injected with isolated human hepatocytes (also referred to as a recipient mouse). Collecting optionally includes separating the hepatocytes from other cell types. In one embodiment, the expanded human hepatocytes are collected from the liver of a Fah-deficient mouse. In some examples, the expanded human hepatocytes are collected from the liver of an FRG mouse or an $F^{pm}RG$ mouse.

Common-γ chain of the interleukin receptor (Il2rg): A gene encoding the common gamma chain of interleukin receptors. Il2rg is a component of the receptors for a number of interleukins, including IL-2, IL-4, IL-7 and IL-15 (Di Santo et al. *Proc. Natl. Acad. Sci. U.S.A.* 92:377-381, 1995). Animals deficient in Il2rg exhibit a reduction in B cells and T cells and lack natural killer cells. Il2rg is also known as interleukin-2 receptor gamma chain.

Cryopreserved: As used herein, "cryopreserved" refers to a cell or tissue that has been preserved or maintained by cooling to low sub-zero temperatures, such in liquid nitrogen. At these low temperatures, any biological activity, including the biochemical reactions that would lead to cell death, is effectively stopped. A cryopreservative that integrates into the cell membrane and change its structure can be used to preserve cell viability.

Decreased liver function: An abnormal change in any one of a number of parameters that measure the health or function of the liver. Decreased liver function is also referred to herein as "liver dysfunction." Liver function can be evaluated by any one of a number of means well known in the art, such as, but not limited to, examination of liver histology and measurement of liver enzymes or other proteins. For example, liver dysfunction can be indicated by necrosis, inflammation, fibrosis, oxidative damage or dysplasia of the liver. In some instances, liver dysfunction is indicated by hepatic cancer, such as hepatocellular carcinoma. Examples of liver enzymes and proteins that can be tested to evaluate liver dysfunction include, but are not limited to, alanine aminotransferase (ALT), aspartate aminotransferase (AST), bilirubin, alkaline phosphatase and albumin. Liver dysfunction also can result in generalized liver failure. Procedures for testing liver function are well known in the art, such as those taught by Grompe et al. (*Genes Dev.* 7:2298-2307, 1993) and Manning et al. (*Proc. Natl. Acad. Sci. U.S.A.* 96:11928-11933, 1999).

Deficient: As used herein, "deficient" refers to an animal, such as a mouse, comprising a mutation in a gene of interest, which results in a substantial decrease in, or the absence of, mRNA expression and/or functional F protein. As used herein, the term "loss of expression" of functional protein does not refer to only a complete loss of expression, but also includes a substantial decrease in expression of functional protein, such as a decrease of about 80%, about 90%, about 95% or about 99%. In one embodiment, the animal comprises homozygous disruptions, such as homozygous deletions, in the gene of interest. A disruption includes, for example, an insertion, deletion, one or more point mutations, or any combination thereof. Rag1-deficient, Rag2-deficient, and Il2rg-deficient refer to animals comprising a mutation in Rag1, Rag2 and Il2rg, respectively, resulting in a substantial decrease in or absence of mRNA expression or production of functional protein. Rag1, Rag2 and Il2rg knockout mice have been previously described and are commercially available.

Definitive Endoderm: Cells that do not express brachyury (brach$^+$) and which, in the presence of differentiation-inducing conditions, are capable of generating the epithelial cells of internal organs comprising the digestive tract, lung cells, liver cells, pancreatic cells and associated structures.

Deplete: To reduce or remove. As used herein, "macrophage depletion" refers to the process of eliminating, removing, reducing or killing macrophages in an animal. An animal that has been depleted of macrophages is not necessarily completely devoid of macrophages but at least exhibits a reduction in the number or activity of macrophages. In one embodiment, macrophage depletion results in at least a 10%, at least a 25%, at least a 50%, at least a 75%, at least a 90% or a 100% reduction in functional macrophages.

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Disruption: As used herein, a "disruption" in a gene refers to any insertion, deletion or point mutation, or any combination thereof. In some embodiments, the disruption leads to a partial or complete loss of expression of mRNA and/or functional protein.

Embryonic stem cells: Embryonic cells derived from the inner cell mass of blastocysts or morulae, optionally that have been serially passaged as cell lines. The term includes cells isolated from one or more blastomeres of an embryo, preferably without destroying the remainder of the embryo. The term also includes cells produced by somatic cell nuclear transfer. "Human embryonic stem cells" (hES cells) includes embryonic cells derived from the inner cell mass of human blastocysts or morulae, optionally that have been serially passaged as cell lines. The hES cells may be derived from fertilization of an egg cell with sperm or DNA, nuclear transfer, parthenogenesis, or by means to generate hES cells with homozygosity in the HLA region. Human ES cells can be produced or derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce an embryonic cell. Human embryonic stem cells include, but are not limited to, MAO1, MAO9, ACT-4, No. 3, H1, H7, H9, H14 and ACT30 embryonic stem cells. Human embryonic stem cells, regardless of their source or the particular method used to produce them, can be identified based on (i) the ability to differentiate into cells of all three germ layers, (ii) expression of at least Oct-4 and alkaline phosphatase, and (iii) ability to produce teratomas when transplanted into immunocompromised animals.

Engraft: To implant cells or tissues in an animal. As used herein, engraftment of human hepatocytes in a recipient mouse refers to the process of human hepatocytes becoming implanted in the recipient mouse following injection. Engrafted human hepatocytes are capable of expansion in the recipient mouse. As described herein, "significant engraftment" refers to a recipient mouse wherein at least about 1% of the hepatocytes in the liver are human. A "highly engrafted" mouse is one having a liver wherein at least about 60% of the hepatocytes are human. However, engraftment efficiency can be higher, such as at least about 70%, at least about 80%, at least about 90% or at least about 95% of the hepatocytes in the mouse liver are human hepatocytes.

Expand: To increase in quantity. As used herein, "expanding" human hepatocytes refers to the process of allowing cell division to occur such that the number of human hepatocytes increases.

In some embodiments, "expansion" is a process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells, but divide to form more cells.

As described herein, human hepatocytes can expand in a recipient rat. The number of human hepatocytes resulting from expansion can vary. In some embodiments, expansion of human hepatocytes in a recipient rat results in an increase of at least 10-fold, at least 50-fold, at least 100-fold, at least 150-fold, at least 200-fold, at least 250-fold, at least 300-fold, at least 400-fold, at least 500-fold or at least 1000-fold.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

Fibroblast growth factor (FGF): Any suitable fibroblast growth factor, derived from any animal, and functional fragments thereof, such as those that bind the receptor and induce biological effects related to activation of the receptor. A variety of FGFs are known and include, but are not limited to, FGF-1 (acidic fibroblast growth factor), FGF-2 (basic fibroblast growth factor, bFGF), FGF-3 (int-2), FGF-4 (hst/K-FGF), FGF-5, FGF-6, FGF-7, FGF-8, FGF-9 and FGF-98. "FGF" refers to a fibroblast growth factor protein such as FGF-1, FGF-2, FGF-4, FGF-6, FGF-8, FGF-9 or FGF-98, or a biologically active fragment or mutant thereof. The FGF can be from any animal species. In one embodiment, the FGF is mammalian FGF, including but not limited to, rodent, avian, canine, bovine, porcine, equine and human. The amino acid sequences and method for making many of the FGFs are well known in the art.

The amino acid sequence of human bFGF (also called FGF-2) and methods for its recombinant expression are disclosed in U.S. Pat. No. 5,439,818, herein incorporated by reference. The amino acid sequence of bovine bFGF (FGF-2) and various methods for its recombinant expression are disclosed in U.S. Pat. No. 5,155,214, also herein incorporated by reference. When the 146 residue forms are compared, their amino acid sequences are nearly identical, with only two residues that differ. Recombinant FGF-2, and other FGFs, can be purified to pharmaceutical quality (98% or greater purity) using the techniques described in detail in U.S. Pat. No. 4,956,455.

An FGF inducer includes an active fragment of FGF. In its simplest form, the active fragment is made by the removal of the N-terminal methionine, using well-known techniques for N-terminal methionine removal, such as a treatment with a methionine aminopeptidase. A second desirable truncation includes an FGF without its leader sequence. Those skilled in the art recognize the leader sequence as the series of hydrophobic residues at the N-terminus of a protein that facilitate its passage through a cell membrane but that are not necessary for activity and that are not found on the mature protein. Human and murine bFGF are commercially available.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), hepatocyte growth factor (HGF) and nerve growth factor (NGF), and actvin-A.

Hepatic pathogen: Refers to any pathogen, such as a bacterial, viral or parasitic pathogen, that infects cells of the liver. In some embodiments, the hepatic pathogen is a "hepatotropic virus" (a virus that targets the liver), such as HBV or HCV.

Hepatocellular carcinoma (HCC): HCC is a primary malignancy of the liver typically occurring in patients with inflammatory livers resulting from viral hepatitis, liver toxins or hepatic cirrhosis.

Hepatocyte: A type of cell that makes up 70-80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile. Hepatocytes manufacture serum albumin, fibrinogen and the prothrombin group of clotting factors and are the main site for the synthesis of lipoproteins, ceruloplasmin, transferrin, complement and glycoproteins. In addition, hepatocytes have the ability to metabolize, detoxify, and inactivate exogenous compounds such as drugs and insecticides, and endogenous compounds such as steroids. A "hepatocyte progenitor" is an immature cell that differentiates into hepatocytes. These cells can express hepatic immature markers (e.g. human fetal hepatocytes express albumin and alphafeto protein). A "human hepatic-specified cell" is a cell after the stage 3 of differentiation using the presently disclosed methods is an immature hepatic cell that express both mRNA encoding Hepatocyte Nuclear Factor 4 Alpha (HNF4a), and the HNF4a protein, at levels comparable to normal human isolated adult hepatocytes. Human hepatic-specified cell also express mRNA of CCAAT/Enhancer Binding Protein Alpha (CEBPa) at levels comparable to human fetal hepatocytes (20-24 weeks gestational age). An IPS cell derived hepatocyte (iHeps) is a cell after the stage 4 of differentiation using the methods disclosed herein. These cells express mRNAs and proteins for the following markers: HNFa, liver X receptor (LXR), UDP glucuronosyltransferase family 1 member A1 (UGT1A1), all at levels comparable to normal human isolated adult hepatocytes. An IPS cell derived hepatocyte (iHeps) also expresses mRNA levels of Fumarylacetoacetate hydrolase (FAH) and ATP-binding cassette transporter ABCA1 at levels that are approximately 50% of the levels expressed by normal human isolated adult hepatocytes. "iHeps" differ from mature human hepatocytes as they have a reduced ability to metabolize, detoxify, and inactivate exogenous compounds such as drugs and insecticides, and endogenous compounds such as steroids.

Hepatocyte Growth Factor (HGF): A growth factor that regulates cell growth, cell motility, and morphogenesis by activating a tyrosine kinase signaling cascade after binding to the proto-oncogenic c-Met receptor. Hepatocyte growth factor is secreted by mesenchymal cells and acts as a multi-functional cytokine on cells of mainly epithelial origin. Its ability to stimulate mitogenesis, cell motility, and matrix invasion gives it a central role in angiogenesis, tumorogenesis, and tissue regeneration. An exemplary amino acid and mRNA sequence for human hepatocyte growth factor is provide in GENBANK® Accession No. NM_000601.5, Oct. 8, 2016, incorporated herein by reference.

Heterozygous: Having dissimilar alleles at corresponding chromosomal loci. For example, an animal heterozygous for a particular gene mutation has the mutation in one allele of the gene but not the other.

Homozygous: Having identical alleles at one or more loci. As used herein, "homozygous for disruptions" refers to an organism having identical disruptions (such as an insertion, deletion or point mutation) of both alleles of a gene.

Immunocompromised or Immunodeficient: Lacking in at least one essential function of the immune system. As used herein, an 'immunocompromised" or "immunodeficient" animal is one lacking specific components of the immune system or lacking function of specific components of the immune system. In one embodiment, an immunocompromised (immunodeficient) animal, such as a mouse or a rat, lacks functional B cells, T cells and/or NK cells. In another embodiment, an immunocompromised (immunodeficient) animal further lacks macrophages. In some embodiments, an "immunocompromised (immunodeficient) animal" comprises one or more of the following genetic alterations: $Rag1^{-/-}$, $Rag2^{-/-}$, $Il2rg^{-/-}$, SCID, NOD and nude. Immunodeficient strains are well known in the art and are commercially available, such as from The Jackson Laboratory (Bar Harbor, Me.) or Taconic (Hudson, N.Y.). In some embodiments, an immunocompromised (immunodeficient) animal is a rat that has been administered one or more immunosuppressants.

Immunosuppressant: Any compound that decreases the function or activity of one or more aspects of the immune system, such as a component of the humoral or cellular immune system or the complement system. In particular embodiments of the disclosure, the immunosuppressant is FK506, cyclosporin A, fludarabine, mycophenolate, prednisone, rapamycin or azathioprine, or combinations thereof.

Known immunosuppressants include, but are not limited to: (1) antimetabolites, such as purine synthesis inhibitors (e.g., azathioprine and mycophenolic acid), pyrimidine synthesis inhibitors (e.g., leflunomide and teriflunomide) and antifolates (e.g., methotrexate); (2) macrolides, such as FK506, cyclosporine A and pimecrolimus; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus and biolimus A9; (6) corticosteroids, such as prednisone; and (7) antibodies to any one of a number of cellular or serum targets.

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., Belimumab); CTLA-4 (e.g., ipilimumab, tremelimumab); CAT (e.g., bertilimumab, lerdelimumab, metelimumab); integrin (e.g., natalizumab); IL-6 receptor (e.g., Tocilizumab); LFA-1 (e.g., odulimomab); and IL-2 receptor/CD25 (e.g., basiliximab, daclizumab, inolimomab).

Other immunsuppressive agents include zolimomab aritox, atorolimumab, cedelizumab, dorlixizumab, fontolizumab, gantenerumab, gomiliximab, maslimomab, morolimumab, pexelizumab, reslizumab, rovelizumab, siplizumab, talizumab, telimomab aritox, vapaliximab, vepalimomab, anti-thymocyte globulin, anti-lymphocyte globulin; CTLA-4 inhibitors (e.g., abatacept, belatacept); aflibercept; alefacept; rilonacept; and TNF inhibitor (e.g., etanercept).

Immunosuppression: Refers to the act of reducing the activity or function of the immune system. Immunosuppression can be achieved by administration of an immunosuppressant compound or can be the effect of a disease or disorder (for example, immunosuppression that results from HIV infection or due to a genetic defect).

Induced pluripotent stem cells (IPSC): A type of pluripotent stem cell artificially derived from a non-pluripotent cell, typically an adult somatic cell, by inducing expression of certain genes. IPSCs can be derived from any organism, such as a mammal. In some embodiments, IPSCs are produced from mice, rats, rabbits, guinea pigs, goats, pigs, cows, non-human primates or humans. Human derived IPSCs are exemplary.

IPSCs are similar to ES cells in many respects, such as the expression of certain stem cell genes and proteins, chromatin methylation patterns, doubling time, embryoid body formation, teratoma formation, viable chimera formation, and potency and differentiability. Methods for producing IPSCs are known in the art. For example, IPSCs are typically derived by transfection of certain stem cell-associated genes (such as Oct-3/4 (Pouf51) and Sox2) into non-pluripotent cells, such as adult fibroblasts. Transfection can be achieved through viral vectors, such as retroviruses, lentiviruses, or adenoviruses. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. In one example, IPSCs from adult human cells are generated by the method of Yu et al. (*Science* 318(5854):1224, 2007) or Takahashi et al. (*Cell* 131(5):861-72, 2007). IPSCs are also known as iPS cells. iPS-Heps, are mature hepatocytes derived from IPSC.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

An "isolated hepatocyte" refers to a hepatocyte that has been obtained from a particular source, such as an organ donor. In some embodiments, an "isolated hepatocyte" is a hepatocyte that has been removed from the body of a donor. In some embodiments, "isolated hepatocytes" are hepatocytes in suspension or hepatocytes contained within a piece of tissue. In particular examples, isolated hepatocytes are those that are substantially separated or purified away from other cell types, or purified away from other types of tissue, such as adipose tissue or fibrotic tissue.

Mammal: This term includes both human and non-human mammals. Examples of mammals include, but are not limited to: humans and veterinary and laboratory animals, such as pigs, cows, goats, cats, dogs, rabbits and mice.

Marker or Label: An agent capable of detection, for example by ELISA, spectrophotometry, flow cytometry, immunohistochemistry, immunofluorescence, microscopy, Northern analysis or Southern analysis. For example, a marker can be attached to a nucleic acid molecule or protein, thereby permitting detection of the nucleic acid molecule or protein. Examples of markers include, but are not limited to, radioactive isotopes, nitorimidazoles, enzyme substrates, co-factors, ligands, chemiluminescent agents, fluorophores, haptens, enzymes, and combinations thereof. Methods for labeling and guidance in the choice of markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the marker is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540 k. Red fluorophores, for example Texas Red, Cy5 and tetramethylrhodamine, are characterized by their emission at wavelengths generally in the range of 590-690 k. In other embodiments, the marker is a protein tag recognized by an antibody, for example a histidine (His)-tag, a hemagglutinin (HA)-tag, or a c-Myc-tag.

Medium or growth medium: A synthetic set of culture conditions with the nutrients necessary to support the growth (cell proliferation/expansion) of a specific population of cells. In one embodiment, the cells are stem cells, such as iPSCs. In another embodiment, the cells are hepatocyte progenitor cells or hepatocytes. Growth media generally include a carbon source, a nitrogen source and a buffer to maintain pH. In one embodiment, growth medium contains a minimal essential media, such as DMEM, supplemented with various nutrients to enhance stem cell growth. Additionally, the minimal essential media may be supplemented with additives such as horse, calf or fetal bovine serum. A "low glucose" medium includes about 0.2 to about 2 grams/liter glucose.

Mesendoderm Cells: Cells that express brachyury (brach$^+$) and which, in the presence of differentiation-inducing conditions, are capable of generating mesoderm and mesoderm derivatives such as cardiac and skeletal muscle, vascular smooth muscle, endothelium and hematopoietic cells, and also are capable of generating endoderm and endoderm derivatives including liver cells.

Nude mouse: Refers to a mouse strain with a genetic mutation that causes a deteriorated or absent thymus, resulting in an inhibited immune system due to a greatly reduced number of T cells. The phenotypic appearance of the mouse is a lack of body hair. Nude mice have a spontaneous deletion in the forkhead box N1 (Foxn1) gene.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pluripotent stem cells: Stem cells that: (a) are capable of inducing teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc), but that cannot form an embryo and the extraembryonic membranes (are not totipotent).

Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). These embryonic stem cells can be generated from embryonic material produced by fertilization or by asexual means, including somatic cell nuclear transfer (SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro).

Pluripotent stem cells also include "induced pluripotent stem cells (iPSCs)" generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell. iPSCs are similar in properties to embryonic stem cells.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: Three or more covalently attached amino acids. The term encompasses proteins, protein fragments, and protein domains. A "DNA-binding" polypeptide is a polypeptide with the ability to specifically bind DNA.

The term "polypeptide" is specifically intended to cover naturally occurring proteins, as well as those which are recombinantly or synthetically produced. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |

| Original Residue | Conservative Substitutions |
| --- | --- |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A promoter can be a constitutively active promoter (i.e., a promoter that is constitutively in an active/"ON" state), an inducible promoter (i.e., a promoter whose state, active/"ON" or inactive/"OFF", is controlled by an external stimulus, e.g., the presence of a particular temperature, compound, or protein.), a spatially restricted promoter (e.g., tissue specific promoter, cell type specific promoter, etc.), or it may be a temporally restricted promoter (i.e., the promoter is in the "ON" state or "OFF" state during specific stages of embryonic development or during specific stages of a biological process, e.g., hair follicle cycle in mice).

Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, steroid-regulated promoters, metal-regulated promoters, estrogen receptor-regulated promoter, etc. Inducible promoters can be regulated by molecules including, but not limited to, doxycycline; RNA polymerase, e.g., T7 RNA polymerase; an estrogen receptor; an estrogen receptor fusion; etc.

Recipient: As used herein, a "recipient rat" is a rat that has been injected with the isolated human hepatocytes described herein. Typically, a portion (the percentage can vary) of the human hepatocytes engraft in the recipient mouse. In one embodiment, the recipient rat is an immunodeficient rat.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Recombinase activating gene 1 (Rag1): A gene involved in activation of immunoglobulin V(D)J recombination. The RAG1 protein is involved in recognition of the DNA substrate, but stable binding and cleavage activity also requires RAG2.

Recombinase activating gene 2 (Rag2): A gene involved in recombination of immunoglobulin and T cell receptor loci. Animals deficient in the Rag2 gene are unable to undergo V(D)J recombination, resulting in a complete loss of functional T cells and B cells (Shinkai et al., *Cell* 68:855-867, 1992).

Serial transplantation: The process for expanding human hepatocytes in vivo in which hepatocytes expanded in a first mouse are collected and transplanted, such as by injection, into a secondary mouse for further expansion. Serial transplantation can further include tertiary, quaternary or additional mice (Overturf et al., *Am. J. Pathol.* 151: 1078-9107, 1997).

Severe combined immunodeficiency (SCID) mouse: Refers to a strain of mice that is unable to undergo V(D)J recombination and therefore lack functional T cells and B cells. SCID mice also have an impaired ability to activate some components of the complement system. SCID mice are homozygous for the $Prkdc^{scid}$ mutation.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, embryonic stem (ES) cells, embryonic germ (EG) cells, germline stem (GS) cells, human mesenchymal stem cells (hMSCs), adipose tissue-derived stem cells (ADSCs), multipotent adult progenitor cells (MAPCs), multipotent adult germline stem cells (maGSCs) and unrestricted somatic stem cell (USSCs). The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation. In one embodiment, the stem cells give rise to hepatocytes.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. As used herein, a "candidate agent" is a compound selected for screening to determine if it can function as a therapeutic agent for a particular disease or disorder.

Titer: In the context of the present disclosure, titer refers to the amount of a particular pathogen in a sample.

Transgene: An exogenous nucleic acid sequence introduced into a cell or the genome of an organism.

Transgenic animal: A non-human animal, usually a mammal, having a non-endogenous (heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, such as, heterologous nucleic acid in the form of an expression construct (such as for the production of a "knock-in" transgenic animal) or a heterologous nucleic acid that upon insertion within or adjacent to a target gene results in a decrease in target gene expression (such as for production of a "knock-out" transgenic animal). A "knock-out" of a gene means that an alteration in the sequence of the gene that results in a decrease of function of the target gene, preferably such that target gene expression is undetectable or insignificant. Transgenic knock-out animals can comprise a heterozygous knock-out of a target gene, or a homozygous knock-out of a target gene. "Knock-outs" also include conditional knock-outs, where alteration of the target gene can occur upon, for example, exposure of the animal to a substance that promotes target gene alteration, introduction of an enzyme that promotes recombination at the target gene site (for example, Cre in the Cre-lox system), or other method for directing the target gene alteration postnatally.

Transplant or transplanting: Refers to the process of grafting an organ, tissue or cells from one subject to another subject, or to another region of the same subject.

Undifferentiated: Cells that display characteristic markers and morphological characteristics of undifferentiated cells, distinguishing them from differentiated cells of embryo or adult origin. Thus, in some embodiments, undifferentiated cells do not express cell lineage specific markers.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes. In one embodiment, a vector is a plasmid vector. In another embodiment, the vector is a viral vector, such as an adenovirus vector or an adeno-associated virus (AAV) vector.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Producing Hepatocytes

Methods are provided herein wherein human somatic cells are used to prepare human induced iPSCs that, in turn, can be used to produce human hepatocytes. The human iPSC, or the human hepatocytes, can be transformed with a nucleic acid molecule operably linked to a heterologous promoter. Optionally, the nucleic acid molecule encodes Cas9, or is transcribed into an inhibitory RNA.

Methods for Producing Induced Pluripotent Stem Cells (iPSC)

iPSC cells can be indefinitely maintained in vitro in an undifferentiated state and yet are capable of differentiating into virtually any cell type.

Somatic Cells

The starting somatic cell can be any cell of interest. Any cells other than germ cells of mammalian origin (such as, humans, mice, monkeys, pigs, rats etc.) can be used as starting material for the production of iPSCs. In one embodiment, the stem cells are human. Examples include keratinizing epithelial cells, mucosal epithelial cells, exocrine gland epithelial cells, endocrine cells, liver cells, epithelial cells, endothelial cells, fibroblasts, muscle cells, cells of the blood and the immune system, cells of the nervous system including nerve cells and glia cells, pigment cells, and progenitor cells, including hematopoietic stem cells, amongst others. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. The somatic cell can be an adult or a fetal cell. In a specific non-limiting example, the somatic cell is a fibroblast. In another specific non-limiting example, the somatic cell is a hepatocyte.

The choice of individuals as a source of somatic cells is not particularly limited. Allogenic cells can be used, if the resulting cells will be transplanted into a subject. Thus, in some embodiments, the iPSCs are not matched for MHC (e.g., HLA) to a subject. In some embodiments, when the iPSCs obtained are to be used for regenerative medicine in humans, cells can be collected from the somatic cells from the subject to be treated, or another subject with the same or substantially the same HLA type as that of the patient. Thus, the stem cells can be autologous or substantially the same HLA type. "Substantially the same HLA type" indicates that the HLA type of donor matches with that of a patient to the extent that the transplanted cells, which have been obtained by inducing differentiation of iPSCs derived from the donor's somatic cells, can be engrafted when they are transplanted to the subject. The subject optionally can be treated with an immunosuppressant. In one example, it includes an HLA type wherein major HLAs (e.g., the three major loci of HLA-A, HLA-B and HLA-DR, the four major loci further including HLA-Cw) are identical.

Somatic cells isolated from a human can be pre-cultured using a medium known to be suitable for their cultivation according to the choice of cells before being subjected to the step of nuclear reprogramming. Specific non-limiting examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. One of skill in the art can readily ascertain appropriate tissue culture conditions to propagate particular cell types from a mammal, such as a human. In some embodiments, to obtain completely xeno-free human iPSCs, the medium can exclude ingredients derived from non-human animals, such as FCS. Media comprising a basal medium supplemented with human-derived ingredients suitable for cultivation of various somatic cells (particularly, recombinant human proteins such as growth factors), non-essential amino acids, vitamins and the like are commercially available; those skilled in the art are able to choose an appropriate xeno-free medium according to the source of somatic cells. Somatic cells pre-cultured using a xeno-free medium are dissociated from the culture vessel using an appropriate xeno-free cell dissociation solution, and recovered, after which they are brought into contact with nuclear reprogramming substances.

Generally, cells are cultured at about 35 to 38° C., usually at 37° C., in about 4-6% $CO_2$, generally at 5% $CO_2$, unless specifically indicated otherwise below.

Constructs Including a Doxycycline Inducible Promoter Operably Linked to a Nucleic Acid Molecule Encoding Cas9 and sgRNAs As disclosed in U.S. Provisional Application No. 62/369,698, incorporated herein by reference, somatic cells can be transfected to introduce a nucleic acid molecule including a doxycycline promoter operably linked to a nucleic acid encoding Cas9. These somatic cells can be used to produce iPSC, which can be differentiated into hepatocytes using the methods disclosed herein. SgRNAs can then be introduced into the iPSC or the iPSC-derived hepatocytes, to induce recombination.

One skilled in the art will recognize that any Cas9 protein can be used in the systems and methods. This promoter provides for inducible expression of Cas9. In a Tet-On system, the rtTA protein is capable of binding the operator (the deoxycycline promoter) only if bound by a tetracycline. Thus, the promoter is activated by doxycycline. The systems disclosed herein utilize an inducible expression platform based on 3 G TET technology. The sequence of this promoter is shown below (SEQ ID NO: 1).

(SEQ ID NO: 1)
ATCGATACTAGACTCGAGTTTACTCCCTATCAGTGATAGAGAACGTATGA

AGAGTTTACTCCCTATCAGTGATAGAGAACGTATGCAGACTTTACTCCCT

ATCAGTGATAGAGAACGTATAAGGAGTTTACTCCCTATCAGTGATAGAGA

ACGTATGACCAGTTTACTCCCTATCAGTGATAGAGAACGTATCTACAGTT

TACTCCCTATCAGTGATAGAGAACGTATATCCAGTTTACTCCCTATCAGT

GATAGAGAACGTATAAGCTTTAGGCGTGTACGGTGGGCGCCTATAAAAGC

AGAGCTCGTTTAGTGAACCGTCAGATCGCCTGGA

Figure 1:
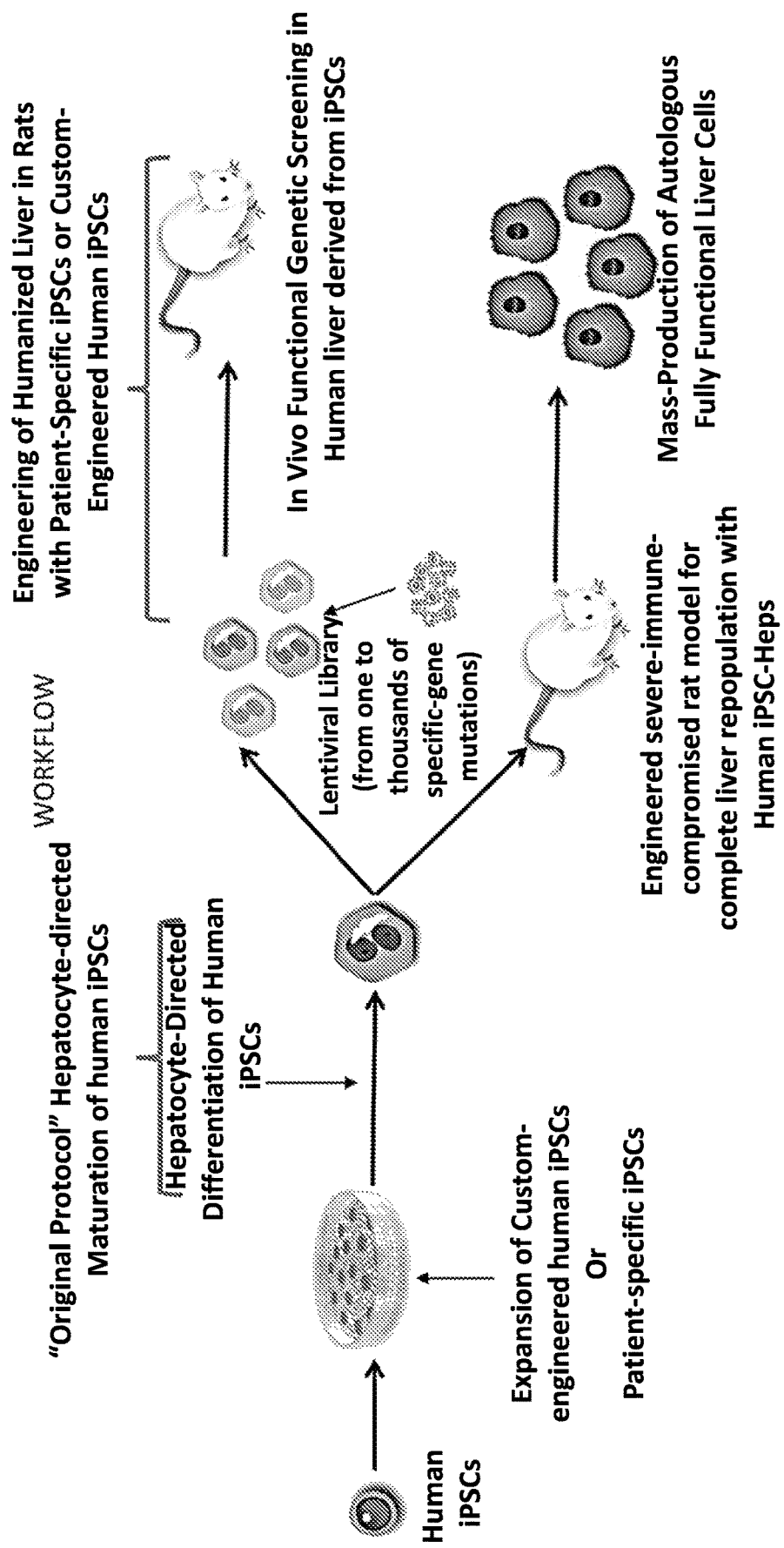
FIG. 1 Schematic of the Workflow for liver repopulation in immune-compromised rats using human iPS-heps.

A doxycycline inducible promoter is a highly sensitive and provides transcription without leakiness. Inducible genetic engineering can be used, using the method disclosed herein, to produce a knockdown, knockin or dual knockins-knockdowns in genes of interest. One form of a doxycycline inducible promoter is the Tet-on-3 G system. This system is composed of these two elements: (1) a reverse tetracycline-controlled transactivator inducible promoter (rtTA) expressed constitutively, under the control of an Ubiquitin C promoter; (2) a Tetracycline Response Element (TRE) controlling the transcription of a sequence of interest. The TRE is composed of 7 repeats of the 19 bp bacterial tet-O sequence placed upstream of a minimal promoter with very low basal expression in the absence of Tet-On. The rtTA protein binds the TRE only if bound by a doxycycline. The addition of doxycycline to the system initiates the transcription of the sequence of interest (fluorescent reporter genes; Cas9 etc.). An exemplary construct is shown in FIG. 1. Additional suitable promoters are disclosed, for example, in Published U.S. Patent Application No. 2014/0107190, which is incorporated herein by reference.

In some embodiments, a doxycycline promoter operably linked to a nucleic acid sequence encoding Cas9 is introduced into the somatic cell. One Cas9 of use is from *Streptococcus pyogenes* as depicted in SEQ ID NO: 2 below.

(SEQ ID NO: 2)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

In other embodiments, the *Streptococcus pyogenes* Cas9 peptide can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M et al. Science. 2012 Aug. 17; 337(6096):816-21; and Jinek M. et al. Science. 2014 Mar. 14; 343(6176). Thus in some embodiments the systems and methods disclosed herein can be used with the wild type Cas9 protein having double-stranded nuclease activity, Cas9 mutants that act as single stranded nickases, or other mutants with modified nuclease activity.

The Cas9 peptide can be an activating Cas9 (Cas9a). Suitable Cas9 sequences include SpCas9-HF1, dCas9-

VP64. Suitable Cas9 molecules are disclosed, for example, in Chavez et al., Nat. Methods 12: 326-328, Oct. 1, 2015, which is incorporated herein by reference. Optionally, and synergistic activator can be encoded with the Cas9, see the internet, sam.genome-engineering.org, incorporated herein by reference.

CRISPR-Cas9 uses a short guide RNA (sgRNA) to direct nuclease Cas9 to the target site and generate double-strand breaks, stimulating DNA repair processes that give rise to DNA editing. To circumvent off targets effects, a modified Cas9 can be utilized, without any reported off target effect (SpCas9-HF1). SpCas9-HF1 enables loss, but also gain of function, provided that the desired template sequence is delivered and used by the Homology Directed Repair cell machinery. Additionally, SpCas9-HF1 can be used for whole genome loss-of-function screening using sgRNA libraries. To enable gain-of-function for whole genome screening, a CRISPR-Cas9 Synergistic Activation Mediator (SAM) complex can be used. This is a protein complex composed of an inactive Cas9-VP64 fusion and activation helper proteins (MS2-P65-HSF1). This complex interacts with sgRNA to ensure robust transcriptional activation of target genes. This system can be used in the present methods for gain-of-function screening.

Cas9 can be used for inhibiting genes (Cas9i). This is a catalytically active Cas9 that, when guided with sgRNA, will induce loss of function by site-specific cleavage of double-stranded DNA, resulting in the activation of the doublestrand break (DSB) repair machinery. Thus, use of Cas9 results in loss of gene function. A single or a library of gRNA can be used for loss-of-function screens. CRISPR knockout libraries or single gRNA render genes non-functional by inducing insertions or deletions in targeted genes.

The Cas9 includes a catalytically active nuclease domain. In some embodiments, the Cas9 nuclease includes an HNH-like endonuclease and a RuvC-like endonuclease. Thus in some embodiments, to generate a double-stranded DNA break, the HNH-like endonuclease cleaves the DNA strand complementary to the sgRNA, and the RuvC-like domain cleaves the non-complementary DNA strand. A Cas9 endonuclease can be guided to specific genomic targets using specific sgRNA (see below).

Optionally, a nucleic acid molecule encoding a marker also can be operably linked to the doxycycline inducible promoter, or to another promoter. Markers include, but are not limited to, enzymes and fluorescent proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the promoter. In addition, other genes can be included, such as genes that may influence stem cells to differentiate, or influence function, or physiology.

In specific non-limiting examples, the marker is tdTomato fluorescent protein or green fluorescent protein. In other embodiments, a nucleic acid molecule encoding a marker is not operably linked the doxycycline promoter.

In some embodiments, the doxycycline promoter operably linked to the nucleic acid encoding Cas9 are included in a vector. Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in $E.\ coli$, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids of use are composed of: (1) a high copy number replication origin, (2) a selectable marker, such as, but not limited to, the neo gene for antibiotic selection, such as with kanamycin, puromycin, neomycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

Viral vectors can be utilized for the introduction of nucleic acids, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377), human herpesvirus vectors (HHV) such as HHV-6 and HHV-7, and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors can be used. Vectors can be obtained from commercial sources (such as PharMingen, San Diego, Calif.; Protein Sciences Corp., Meriden, Conn.; Stratagene, La Jolla, Calif.). Suitable vectors are disclosed, for example, in U.S. Published Patent Application No. 2010/0247486, which is incorporated herein by reference. In specific non-limiting examples, the vectors are retrovirus vectors (for example, lentivirus vectors), measles virus vectors, alphavirus vectors, baculovirus vectors, Sindbis virus vectors, adenovirus and poliovirus vectors.

In some embodiments, the vector is a lentiviral vector. An advantage of lentiviruses for infection of cells is the ability for sustained transgene expression. Leintiviruses include, but are not limited to, Human Immunodeficiency Virus type 1 (HIV-1), Human Immunodeficiency Virus type 2 (HIV-2), Simian Immunodeficiency Virus (SIV), Feline Immunodeficiency Virus (FIV), Equine Infectious Anaemia Virus (EIAV), Bovine Immunodeficiency Virus (BIV), Visna Virus of sheep (VISNA) and Caprine Arthritis-Encephalitis Virus (CAEV). Lentiviral vectors are well known in the art (see, for example, Naldini et al., Science, 272(5259):263-267, 1996; Zufferey et al., Nat Biotechnol, 15(9):871-875, 1997; Blomer et al., J Virol, 71(9):6641-6649, 1997; U.S. Pat. Nos. 6,013,516 and 5,994,136). Recombinant lentiviral vectors are capable of infecting non-dividing cells and can be used for both in vivo and in vitro gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

A recombinant lentivirus can be targeted to a specific cell type by linkage of the envelope protein with an antibody or a particular ligand for targeting to a receptor of a particular cell-type. A sequence (including a regulatory region) of interest is inserted into the viral vector, along with another gene which encodes the ligand for a receptor on a specific target cell, in order to produce a target-specific vector. The recombinant lentiviruses can be genetically modified in such a way that certain genes constituting the native infectious virus are eliminated and replaced with a nucleic acid sequence of interest to be introduced into the target cells.

In some embodiments, a lentiviral vector can integrate into the genome of the host cell. The genetic material thus transferred is then transcribed and possibly translated into proteins inside the host cell. In other embodiments, a lentiviral vector is a non integrative lentiviral vector, such that the vector is present in episomal forms.

The lentiviral vector can further comprise additional elements which help to improve expression of the genes encoded within the vector. Regions required for the integration of the vector into the genome of the target cell such as the Long-terminal repeats (LTRs). Thus, a lentiviral vector can include a 5' LTR and a 3' LTR. "5' LTR" refers to a 5' retroviral or lentiviral long terminal repeat, which may or may not be modified from its corresponding native 5' LTR by deleting and/or mutating endogenous sequences and/or adding heterologous sequences. The 5' LTR may be natural or synthetic. "3' LTR" refers to a 3' retroviral or lentiviral long terminal repeat, which may or may not be modified from its corresponding native (i.e., that existing in the wild-type retrovirus) 3' LTR by deleting and/or mutating endogenous sequences and/or adding heterologous sequences. The 3' LTR may be natural or synthetic.

An encapsidation sequence such as the lentiviral Psi (ψ) sequence can be included in the vector. In some embodiments, sequences enhancing the RNA nuclear export, such as the sequence comprising the HIV-1 REV response element (RRE) sequence, can be included in the vector. Another sequence that enhances the RNA nuclear export is the CTE sequence (Oh et al, 2007, Retrovirology. 2007 Jun. 5; 4:38.). These sequences are also useful for determining the copy number of the integrated lentiviral vectors. Other sequences that enhance DNA nuclear import are lentiviral cPPT CTS sequences from HIV-2, SIV, FIV, EIAV, BIV, VISNA and CAEV. Any of these sequences can be included in the vector.

In another embodiment the lentiviral vector is another form of self-inactivating (SIN) vector as a result of a deletion in the 3' long terminal repeat region (LTR). In some examples, the vector contains a deletion within the viral promoter. The LTR of lentiviruses such as the HIV LTR contains a viral promoter. Although this promoter is relatively inefficient, when transactivated by e.g. tat, the promoter is efficient because tat-mediated transactivation increases the rate of transcription about 100 fold. In some circumstances, the presence of the viral promoter can interfere with transcription of heterologous promoters operably linked to a transgene. To minimize such interference and better regulate the expression of transgenes, the lentiviral promoter may be deleted.

In some embodiments, the lentiviral vector comprises, in the 5' to 3' orientation: the 5' LTR (wild-type or modified), A Rev response element (RRE), a c polypurine tract (cPPT), the transcriptional regulatory region, the doxycycline promoter linked to Cas9, an optional transcriptional regulation element, and the 3' LTR.

Methods of transfection of DNA include calcium phosphate coprecipitates, conventional mechanical procedures such as microinjection, electroporation, insertion of a plasmid encased in liposomes, or virus vectors.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins.

In some embodiments, the methods also include introducing nucleic acids encoding guide RNAs (gRNAs). In some embodiments, the methods disclosed herein can include introducing the nucleic acid encoding the sgRNAs into the somatic cell, prior to inducing formation of an iPSC. In other embodiments, the methods disclosed herein can include introducing the nucleic acid encoding the sgRNAs into an iPSC including the doxycycline promoter operably linked to Cas9. In further embodiments, the methods disclosed herein can include introducing the nucleic acid encoding the sgRNAs into a differentiated cell, after inducing the iPSC (including the doxycycline promoter operably linked to Cas9) to differentiate.

The nucleic acid encoding the sgRNA can be linked to a constitutive promoter. Suitable promoters include, but are not limited to, the U6 promoter or the ubiquitin promoter.

```
                                              (SEQ ID NO: 6)
CGATACAAGGCTGTTAGAGAGATAATTAGAATTAATTTGACTGTAAACAC

AAAGATATTAGTACAAAATACGTGACGTAGAAAGTAATAATTTCTTGGGT

AGTTTGCAGTTTTAAAATTATGTTTTAAAATGGACTATCATATGCTTACC

GTAACTTGAAAGTATTTCGATTTCTTGGCTTTATATATCTTGTGGAAAGG

ACGAAACACCGGAGACGGTTGTAAATGAGCACACAAAATACACATGCTAA
```

```
AATATTATATTCTATGACCTTTATAAAATCAACCAAAATCTTCTTTTTAA

TAACTTTAGTATCAATAATTAGAATTTTTATGTTCCTTTTTGCAAACTTT

TAATAAAAATGAGCAAAATAAAAAAACGCTAGTTTTAGTAACTCGCGTTG

TTTTCTTCACCTTTAATAATAGCTACTCCACCACTTGTTCCTAAGCGGTC

AGCTCCTGCTTCAATCATTTTTTGAGCATCTTCAAATGTTCTAACTCCAC

CAGCTGCTTTAACTAAAGCATTGTCTTTAACAACTGACTTCATTAGTTTA

ACATCTTCAAATGTTGCACCTGATTTTGAAAATCCTGTTGATGTTTTAAC

AAATTCTAATCCAGCTTCAACAGCTATTTCACAAGCTTTCATGATTTCTT

CTTTTGTTAATAAACAATTTTCCATAATACATTTAACAACATGTGATCCA

GCTGCTTTTTTTACAGCTTTCATGTCTTCTAAAACTAATTCATAATTTTT

GTCTTTTAATGCACCAATATTTAATACCATATCAATTTCTGTTGCACCAT

CTTTAATTGCTTCAGAAACTTCGAATGCTTTTGTAGCTGTTGTGCATGCA

CCTAGAGGAAAACCTACAACATTTGTTATTCCTACATTTGTGCCTTTTAA

TAATTCTTTACAATAGCTTGTTCAATATGAATTAACACAAACTGTTGCAA

AATCAAATTCAATTGC
```

In some embodiments, these primers are used when sequencing nucleic acids encoding sgRNAs into an iPSC or into a cell differentiated from the iPSC. Suitable primers include, but are not limited to:

```
hU6-F
                                    (SEQ ID NO: 32)
    5'-GAGGGCCTATTTCCCATGATT-3'

LKO.1 5'
                                    (SEQ ID NO: 33)
    5'-GACTATCATATGCTTACCGT-3'
```

In other embodiments, an inducible promoter is utilized, and the sgRNAs are introduced into the starting somatic cell. The sgRNA can also be introduced into cells differentiated from the iPSC. When recombination is desired, expression can, in some circumstances, be induced from this inducible promoter. Thus, expression can be induced in the starting somatic cells, iPSCs, or cells differentiated from the iPSCs. These promoters include, but are not limited to:

| Target Issue | Promoter | Vector | Transgene | References |
|---|---|---|---|---|
| LIVER | Apo A-I | Ad | Apo A-I | [De Geest et al., 2000] |
| | ApoE | HCAd | ApoE | [Kim et al., 2001] |
| | α$_1$-antitrypsin (hAAT) | Ad | Apo A-I | [Van Linthout et al., 2002] |
| | | HCAd | hAAT | |
| | | Plasmid | factorIX | [Schniedner et al., 1998] [Schniedner et at, 2002] |
| | | | | [Miao et al., 2001] |
| | | | | [Ehrhardt et al., 2002] |
| | hAAT & Apo A-I | Retroviral | hAAT | [Okuyama, 1996] |
| | Transthyretin | HCAd | hGH | [Burcin et al., 1999] |
| | Liver-enriched activator | Transgenic | LUC | [Kistner et al., 1996] |
| | Albumin | HCAd | FactorVIII | [Reddy et al., 2002] |
| | | Lentivirus | factorIX | [Follenzi et al., 2002] |
| | Phosphoenolpyruvate Carboxykinase (PEPCK) | HCAd | VLDLR | [Oka et al., 2001] |
| | RNAP$_{11}$ promoter | Retrovirus | hAAT | [Rettinger et al., 1994] |
| ENDOTHELIUM | PAI-1 | AAV | Thrombomodulin | [Mimur J, 2001] |
| | ICAM-2, Endoglin | Plasmid | Endoglin | [Velasco et al., 2001] |
| | ICAM-2, flt-1, vWF | Ad | lacZ | Nicklin et al., 2001] |
| MUSCLE | MCK | Ad | LacZ, LUC | [Hauser et al., 2000] |
| | | Plasmid | hBSAg | [Larochelle et al., 2002] |
| | | Ad/AAV | γ-sarcoglycan | |
| | | | | [Weeratna et al., 2001] |
| | | | | [Cordier et al., 2000] |
| | SMC α-actin | Plasmid | LUC | [Keogh et al., 1999] |
| | | Ad | Rb/E2F hybrid | [Prentice et al., 1997] |
| | | Ad | GFP, lacZ, IFN$_y$ | [Wills et al., 2001] |
| | | AAV | Factor IX | [Ribault et al., 2001] |
| | | | | [Hagstrom et al., 2000] |
| | Myosin heavy-chain | Plasmid | CAT | [Skarli et al., 1998] |
| | | AAV | lacZ, hGH | [Aikawa et al., 2002] |
| | Myosin light-chain | Ad | LacZ, LUC | [Griscelli et al., 1998] |
| | | AAV | GFP, antisense | [Franz et al., 1997] |
| | | | | [Phillips et al., 2002] |
| EPITHELIUM | Cytokeratin 18 | Plasmid | LacZ, CFTR | [Chow et al., 1997] |
| | | | | [Koehler et al., 2001] |
| | CFTR | Ad | LacZ, LUC | [Imler et al., 1996] |
| | | | | [Suzuki et al., 1996] |

-continued

| Target Issue | Promoter | Vector | Transgene | References |
|---|---|---|---|---|
| NEURONAL | GFAP, NSE, Synapsin I, Preproenkephalin, Dopamine β-Hydroxylase (dβH) | Ad AAV Plasmid, Ad | LacZ, GFP LUC, GFP CAT, GFP, lacZ | [Smith-Arica et al., 2000] [Glover et al., 2002] [Xu et al., 2001] [Hwang et al., 2001] |
| | Prolactin | Ad | LacZ, HSV-tk | [Southgate et al., 2000] |
| | Myelin basic protein | AAV | GFP | [Chen et al., 1998] |
| ERYTHROID | Ankyrin | Retrovirus Lentivirus | γ-globin ferrochelatase | [Sabatino et al., 2001] [Richard et al., 2001] |
| | α-spectrin, Globin | Lentivirus | GFP, β/γ -globin | [Moreau-Gaudry et al., 2001] |
| | HLA-Drα | Lentivirus | GFP | [Cui et al., 2002] |
| | CD4 | Retroviral | GFP | [Zhao-Emonet J C, 2000] |
| | Dectin-2 | Plasmid | GFP, LUC | [Morita et al., 2001] |

ABBREVIATIONS: PAI-1, plasminogen activator inhibitor 1; ICAM-2, intercellular adhesion molecule2; flt-1, fms-like tyrosine kinase-1; vWF, von-Willebrand factor; MCK, muscle creatine kinase; CFTR cystic fibrosis transmembrane conductance regulator; GFAP, glial fibrillary acidic protein; NSE, neuronal-specific endolase; LUC, luciferase; GFP, green fluorescent protein; HSV-tk, herpes simplex virus thymidine kinase.

Table from Papadkis et al., Current Gene Therapy 4: 89-113, 2004, incorporated herein by reference. One of skill in the art can readily identify promoters of use.

The promoter can be a constitutive promoter, such as, but not limited to, the ubiquitin promoter, see below.

The Cas9 RNA guide system consists of mature crRNA that is base-paired to trans-activating crRNA (tracrRNA), forming a two-RNA structure that directs Cas9 to the locus of a desired double-stranded (ds) break in target DNA. In some embodiments base-paired tracrRNA:crRNA combination is engineered as a single RNA chimera to produce a guide sequence (e.g. sgRNA) which preserves the ability to direct sequence-specific Cas9 dsDNA cleavage (see Jinek, M., et. al., Science. 17 Aug. 2012:337; 816-821). In some embodiments, the Cas9-guide sequence complex results in cleavage of one or both strands at a target sequence within a gene of interest. Thus, the Cas9 endonuclease (Jinek, M., et. al., Science. 2012; Mali, P., et. al., Nat Methods. 2013 October; 10(10): 1028-1034) and the sgRNA molecules are used sequence-specific target recognition, cleavage, and genome editing of the gene of interest. In one embodiment, the cleavage site is at a specific nucleotide, such as, but not limited to the 16, 17, or 18th nucleotide of a 20 nucleotide target. In one non-limiting example, the cleavage site is at the 17th nucleotide of a 20-nt target sequence (see FIG. 1 and FIG. 3). The cleavage can be a double stranded cleavage. The cleavage site can be in the coding region of any gene, or in a non-coding region, such as in a promoter, enhancer, intron, etc. In some embodiments, a loss of function is produced. In other embodiments, a gain of function is produced.

In some embodiments, the sgRNA molecule is selected so that the target genomic targets bear a protospacer adjacent motif (PAM). In some embodiments, DNA recognition by guide RNA and consequent cleavage by the endonuclease requires the presence of a protospacer adjacent motif (PAM) (e.g. 5'-NGG-3') in immediately after the target.

In some embodiments, cleavage occurs at a site about three base-pairs upstream from the PAM. In some embodiments, the Cas9 nuclease cleaves a double stranded nucleic acid sequence.

In some embodiments, the guide sequence is selected to reduce the degree of secondary structure within the sequence. Secondary structure may be determined by any suitable polynucleotide folding algorithm. Some programs are based on calculating the minimal Gibbs free energy. An example of one such algorithm is mFold (Zuker and Stiegler, Nucleic Acids Res. 9 (1981), 133-148). Another example folding algorithm is the online webserver RNAfold, which uses the centroid structure prediction algorithm (see e.g. A. R. Gruber et al., 2008, Cell 106(1): 23-24; and PA Can and GM Church, 2009, *Nature Biotechnology* 27(12): 1151-62). Guide sequences can be designed using the MIT CRISPR design tool found at crispr.mit.edu or the E-CRISP tool found at www.e-crisp.org/E-CRISP. Additional tools for designing tracrRNA and guide sequences are described in Naito Y et al., Bioinformatics. 2014 Nov. 20, and Ma et al. BioMed Research International, Volume 2013 (2013), Article ID 270805. The crRNA can be 18-48 nucleotides in length. The crRNA can be 18, 19, 20, 21, 22, 23, 24 or 25 nucleotides in length. In one example, the crRNA is 20 nucleotides in length. In additional embodiments, the tracrRNA is pre-optimized, and is 83 nucleotides in length, see SEQ ID NO: 3, see below:

(SEQ ID NO: 3)
GTTTTAGAGCTAGAAATAGCAAGTTAAAATAAGGCTAGTCCGTTATCAAC
TTGAAAAAGTGGCACCGAGTCGGTGCTTTTTTT.

As noted above, the system disclosed herein can include a promoter, such as, but not limited to, a U6 or H1 promoter operably linked to one or more nucleotide sequences, such as the sgRNAs.

The U6 promoter can include the following nucleic acid sequence:

(SEQ ID NO: 4)
GAGGGCCTATTTCCCATGATTCCTTCATATTTGCATATACGATACAAGGC

TGTTAGAGAGATAATTGGAATTAATTTGACTGTAAACACAAAGATATTAG

TACAAAATACGTGACGTAGAAAGTAATAATTTCTTGGGTAGTTTGCAGTT

TTAAAATTATGTTTTAAAATGGACTATCATATGCTTACCGTAACTTGAAA

GTATTTCGATTTCTTGGCTTTATATATCTTGTGGAAAGGACGAAACACC, see also GENBANK® Accession No. X07425.1, incorporate herein by reference).

Disclosed below is a U6 sgRNA sequence, wherein the tracrRNA is underlined. The tracer sequence includes seven thymidines for terminating RNA transcription. The small "g," "ga," and the second "g" border the SapIrev and SapI sites where the nucleic acid encoding the sgRNA is inserted.

```
                                          (SEQ ID NO: 5)
GGCGCGCCGGATCCGAGGGCCTATTTCCCATGATTCCTTCATATTTGCAT

ATACGATACAAGGCTGTTAGAGAGATAATTGGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCgGAAGAGCgaGCTCTTCgGTTTTAGAGCTAGAAATAG

CAAGTTAAAATAAGGCTAGTCCGTTATCAACTTGAAAAAGTGGCACCGAG

TCGGTGCTTTTTTTGGTACCGGCGCGCC
```

In some embodiments, more than one DNA break can be introduced by using more than one sgRNA. For example, two sgRNAs can be utilized, such that two breaks are achieved. When two or more sgRNAs are used to position two or more cleavage events, in a target nucleic acid, it is contemplated that in an embodiment the two or more cleavage events may be made by the same or different Cas9 proteins. For example, when two sgRNAs are used to position two double strand breaks, a single Cas9 nuclease may be used to create both double strand breaks.

In some embodiments, the disclosed methods include the use of one or more vectors comprising: a) doxycycline promoter operably linked to a nucleotide sequence encoding a Type II Cas9 nuclease, b) a U6 promoter operably linked to one or more nucleotide sequences encoding one or more CRISPR-Cas guide RNAs that hybridize with the gene of interest in a eukaryotic cell. Components (a) and (b) can be located on same or different vectors, whereby the one or more guide RNAs target the gene of interest in the eukaryotic cell and the Cas9 protein cleaves the gene of interest. Thus, the sequence of the gene of interest is modified in the target cell. Suitable vectors are disclosed above.

The disclosed methods can be used to target any gene of interest, including increasing or decreasing expression. Thus disclosed herein are methods for the knock-in or knock-out of any gene.

Some targets, to the extent that they are present in or conditions of the liver are metabolic disorders, are: Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); hepatic steatosis (SIRT1, EGFR, GH, SIRT6); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3); Hepatic failure, early onset, and neurologic disorder (SCOD1, SCO1, HNF4a, FOXA2, FOXA1, HNF1a, FXR, LXR, PPRa, FOXO1, PGCA, PXR, CAR, RXR, NTCP, OATP, ABCA1, CX32, ABCB11), Hepatic lipase deficiency (LIPC), Hepatoblastoma, cancer and carcinomas (CTNNB1, PDGFRL, PDGRL, PRLTS, AXIN1, AXIN, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63).); liver regeneration (GH, JAK2, STAT5, SHC, SOS, GRB2, RAS, RAF, MEK, ERK1/2, FAK, P130, CRKII, MEKK, JNK, P38, IRS1-3, PI3K, AKT, PLC, PKC, GHR, IGF-1, IGF-2, ALS, SOCS2, SHP1, EGFR, AR, P21, HB-EGF, EGF, TGFa, C-SRC, STAT1, STAT3, P110, P85, AKT, mTOR, GSK3B, IKK, NFKB, CREB, PLC, PKC, PIP2, IP3, DAG, C-MYC, ADAM17, PDGFa, PDGFRa, PDGFRb, C/EBPa, p27), metabolic deficiencies (OTC, ALB, AFP, TDO, PEPCK, UGT1A1, A1AT, TAT, ADH1, CPS), Liver detoxification (CYP2C9, CYP2C19, CYP2D6, CYP3A4, CYP3A7, CYP7A1, CYP1A2, CYP2B6, CYP2C8); Cholangiocyte function (CFTR, SOX9, CK7, CK19, HNF6, HNF1b). Other preferred targets include any one or more of include one or more of: PCSK9; Hmgcr; SERPINA1; ApoB; and.or LDL. Of course, the disclosed methods are not limited to targeting metabolic disorders. These targets are provided only by way of example.

In specific non-limiting embodiments, the gene of interest is SIRT1, SIRT6, SLC5A5, or ß-catenin.

B. Inhibitory Nucleic Acid Molecules

Inhibitory nucleic acids that decrease the expression and/or activity of any protein of interest. The starting somatic cells, or the resulting iPSC can also be transformed with a nucleic acid encoding such an inhibitory RNA. Thus, the iPSC can include a promoter, such as a liver specific promoter, operably linked to a nucleic acid molecule that is transcribed to produce an inhibitory RNA. Additionally, shRNA sequences can be used for identification of active shmir sequences against a gene of interest. The shmir sequence is placed under the control of an inducible promoter activated by doxycycline. In the presence of doxycycline, the reverse tetracycline-controlled transactivator (rtTA) recognizes the tetO operator sequences within the Tetracyclin Responsive Element (TRE). The system activates of shmir leading to a knockdown of a gene of interest. This down technology can be used to knockdown any gene inside the genome to more than 80%. In some examples, shmir template oligonucleotide cassettes against for instance SIRT1 are cloned into a shuttle plasmid under the control of the human EF1a promoter.

In some specific non-limiting examples, the coding region of the full length SIRT1 target cDNA specified is PCR-amplified and cloned into a vector, such as the validation vector pVal downstream of the EGFP coding region resulting in pVal-target. The EFla-target regions of the shuttle plasmids are transferred into pVal-target by recombinational cloning. NIH-3T3 cells are transfected at a confluency of about 50% with the validation plasmids and are incubated under standard cell culture condition for 48 h. Total RNA is then isolated and 1 μg is reverse transcribed using a mixture of random hexamer and oligo-dT primer. The Shmir silencing efficiency of is determined by quantification of the target cDNA expression levels relative to that found in cells transfected with the NT-shRNA control vector using the vector-encoded marker transcript as internal reference gene. Systems fulfilling validation criteria (>80% knock downs, complete knock-outs or knock-ins) were cloned into a pcLVi(3 G) lentiviral vector.

In some examples, such inhibitor nucleic acid molecules decrease expression or activity of a gene expressed in the liver by at least 20%, at least 40%, at least 50%, at least 75%, at least 80%, at least 90%, at least 95%, at least 98% or even 100%. One embodiment is a RNA interference (RNAi), such as, but not limited to, small inhibitory RNA (siRNA) or short hairpin RNA, which can be used for interference or inhibition of expression of a target. RNAis that specifically target genes expressed in the liver are commercially available, for example from Santa Cruz Biotechnology, Inc., ThermoFisher Scientific, and Sigma Aldrich.

Generally, siRNAs are generated by the cleavage of relatively long double-stranded RNA molecules by Dicer or DCL enzymes (Zamore, *Science,* 296:1265-1269, 2002; Bernstein et al., *Nature,* 409:363-366, 2001). In animals and plants, siRNAs are assembled into RISC and guide the sequence specific ribonucleolytic activity of RISC, thereby resulting in the cleavage of mRNAs or other RNA target molecules in the cytoplasm. In the nucleus, siRNAs also guide heterochromatin-associated histone and DNA methylation, resulting in transcriptional silencing of individual genes or large chromatin domains.

The present disclosure can utilize RNA suitable for interference or inhibition of expression of a gene expressed in the liver, which RNA includes double stranded RNA of about 19 to about 40 nucleotides with the sequence that is substantially identical to a portion of an mRNA or transcript of a target gene, for which interference or inhibition of expression is desired. For purposes of this disclosure, a sequence of the RNA "substantially identical" to a specific portion of the mRNA or transcript of the target gene for which interference or inhibition of expression is desired differs by no more than about 30 percent, and in some embodiments no more than about 10 percent, from the specific portion of the mRNA or transcript of the target gene. In particular embodiments, the sequence of the RNA is exactly identical to a specific portion of the mRNA or transcript of the target gene.

Thus, siRNAs of use include double-stranded RNA of about 15 to about 40 nucleotides in length and a 3' or 5' overhang having a length of 0 to 5-nucleotides on each strand, wherein the sequence of the double stranded RNA is substantially identical to (see above) a portion of a mRNA or transcript of a nucleic acid encoding a protein of interest. In particular examples, the double stranded RNA contains about 19 to about 25 nucleotides, for instance 20, 21, or 22 nucleotides substantially identical to a nucleic acid encoding a protein of interest. In additional examples, the double stranded RNA contains about 19 to about 25 nucleotides 100% identical to a nucleic acid encoding a protein of interest. It should be not that in this context "about" refers to integer amounts only. In one example, "about" 20 nucleotides refers to a nucleotide of 19 to 21 nucleotides in length.

Regarding the overhang on the double-stranded RNA, the length of the overhang is independent between the two strands, in that the length of one overhang is not dependent on the length of the overhang on other strand. In specific examples, the length of the 3' or 5' overhang is 0-nucleotide on at least one strand, and in some cases it is 0-nucleotide on both strands (thus, a blunt dsRNA). In other examples, the length of the 3' or 5' overhang is 1-nucleotide to 5-nucleotides on at least one strand. More particularly, in some examples the length of the 3' or 5' overhang is 2-nucleotides on at least one strand, or 2-nucleotides on both strands. In particular examples, the dsRNA molecule has 3' overhangs of 2-nucleotides on both strands.

Thus, in one particular provided RNA embodiment, the double-stranded RNA contains 20, 21, or 22 nucleotides, and the length of the 3' overhang is 2-nucleotides on both strands. In embodiments of the RNAs provided herein, the double-stranded RNA contains about 40-60% adenine+uracil (AU) and about 60-40% guanine+cytosine (GC). More particularly, in specific examples the double-stranded RNA contains about 50% AU and about 50% GC.

Also described herein are RNAs that further include at least one modified ribonucleotide, for instance in the sense strand of the double-stranded RNA. In particular examples, the modified ribonucleotide is in the 3' overhang of at least one strand, or more particularly in the 3' overhang of the sense strand. It is particularly contemplated that examples of modified ribonucleotides include ribonucleotides that include a detectable label (for instance, a fluorophore, such as rhodamine or FITC), a thiophosphate nucleotide analog, a deoxynucleotide (considered modified because the base molecule is ribonucleic acid), a 2'-fluorouracil, a 2'-aminouracil, a 2'-aminocytidine, a 4-thiouracil, a 5-bromouracil, a 5-iodouracil, a 5-(3-aminoallyl)-uracil, an inosine, or a 2'O-Me-nucleotide analog.

Antisense and ribozyme molecules for a gene of interest are also of use in the method disclosed herein. Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target cell producing a protein of interest. The use of antisense methods to inhibit the in vitro translation of genes is well known (see, for example, Marcus-Sakura, *Anal. Biochem.* 172:289, 1988).

An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid molecule can be chemically synthesized using naturally occurring nucleotides or variously modified nucleotides designed to increase the biological stability of the molecules or to increase the physical stability of the duplex formed between the antisense and sense nucleic acids, such as phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, amongst others.

Use of an oligonucleotide to stall transcription is known as the triplex strategy where an oligonucleotide winds around double-helical DNA, forming a three-strand helix. Therefore, these triplex compounds can be designed to recognize a unique site on a chosen gene (Maher, et al., *Antisense Res. and Dev.* 1(3):227, 1991; Helene, C., *Anticancer Drug Design* 6(6):569), 1991. This type of inhibitory oligonucleotide is also of use in the methods disclosed herein.

Ribozymes, which are RNA molecules possessing the ability to specifically cleave other single-stranded RNA in a manner analogous to DNA restriction endonucleases, are also of use. Through the modification of nucleotide sequences, which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

Various delivery systems are known and can be used to administer the siRNAs and other inhibitory nucleic acid molecules as therapeutics. Such systems include, for example, encapsulation in liposomes, microparticles, microcapsules, nanoparticles, recombinant cells capable of expressing the therapeutic molecule(s) (see, e.g., Wu et al., J. Biol. Chem. 262, 4429, 1987), construction of a therapeutic nucleic acid as part of a retroviral or other vector, and the like. Any of the vectors disclosed above, for the introduction of Cas9, can also be used for introducing inhibitory nucleic acids.

Reprogramming to Produce iPSC

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 2012/0196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HPV16 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

After being cultured with nuclear reprogramming substances, the cell can, for example, be cultured under conditions suitable for culturing stem cells. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

In some embodiments, the cell is cultured in the co-presence of mouse embryonic fibroblasts treated with radiation or an antibiotic to terminate the cell division, as feeder cells. Mouse embryonic fibroblasts in common use as feeders include the STO cell line (ATCC CRL-1503) and the like; for induction of an iPSC, useful cells can be generated by stably integrating the neomycin resistance gene and the LIF gene in the STO cell (SNL76/7 STO cell; ECACC 07032801) (McMahon, A. P. & Bradley, A. Cell 62, 1073-1085, 1990) and the like can be used. Mitomycin C-treated MEFs are commercially available from Millipore. Gamma-irradiated MEFs are commercially available from Global Stem Generally, somatic cells are transduced with reprogramming factors in the absence of MEFs. In some embodiments, about 7 to eight days after transduction, the cells are re-seeded onto MEFs.

The expression of a key pluripotency factor, NANOG, and embryonic stem cell specific surface antigens (SSEA-3, SSEA-4, TRA1-60, TRA1-81) have been routinely used to identify fully reprogrammed human cells. At the functional level, iPSCs also demonstrate the ability to differentiate into lineages from all three embryonic germ layers.

In some embodiments, upon inducing the somatic cells to produce the human iPSC, more than 10% of the human induced pluripotent stem cells express the Cas9 when the cells are exposed to doxycycline. In additional embodiments, more than about 15%, about 20%, about 25%, about 30%, about 35%, about 40%, about 45%, or about 50% of the human induced pluripotent stem cells express the Cas9 when the cells are exposed to doxycycline. In specific non-limiting examples, about 35% to about 45% of the human induced pluripotent stem cells express the Cas9 when the cells are exposed to doxycycline, such as about 38% to about 42%, such as about 40%. In this context, "about" indicates within one percent. In other embodiments, more than 15%, 20%, 25%, 30%, 35%, 40%, 45% or 50% of the human induced pluripotent stem cell clones or colonies express the Cas9 when the cells are exposed to doxycycline.

In specific non-limiting examples, 35% to 45% of the human induced pluripotent stem cell clones or colonies express the Cas9 when the cells are exposed to doxycycline, such as 38% to 42%, such as 40%.

Differentiation of iPSC

Several methods are disclosed herein for differentiating human iPSC into human hepatocytes. In the disclosed methods, in vitro steps are utilized to produce human hepatocytes from human IPSC. Optionally, the human hepatocytes can be expanded in an immunocompromised animal, such as, but not limited to, an immunocompromised transgenic rat.

In some embodiments, methods are provided herein for producing human hepatocytes. The method includes a) culturing human induced pluripotent stem cells (iPSC) in a first medium comprising an effective amount of activin A, fibroblast growth factor (FGF)-2 and bone morphogenic protein (BMP)-4 for a sufficient amount of time to produce mesendoderm cells. In the presence of specific differentiation-inducing conditions, mesendoderm cells are capable of generating endoderm and endoderm derivatives including liver cells and also are capable of generating mesoderm and mesoderm derivatives such as cardiac and skeletal muscle, vascular smooth muscle, endothelium and hematopoietic cells. In some embodiments, the human iPSC are cultured in the first medium for 2 to 3 days, such as for 2, 2.5 or 3 days. The culture conditions are generally in standard culture conditions, at about 37° C., and atmospheric oxygen (e.g., about 21% oxygen).

In some non-limiting examples, the first medium can include, for example, about 50 to about 200 ng/mL activin A, such as about 100 to about 200 ng/mL of activin A. Thus, the first medium can include about 50, 60, 70, 80, 90, 100, 110, 120, 130, 140, 150, 160, 170, 180, 190, or 200 ng/ml of activin A. In additional non-limiting examples, the first medium can include about 10 to about 50 ng/mL of FGF-2, such as about 20 to about 50 ng of FGF-2. Thus, the first medium can include about 20, 25, 30, 35, 40, 35 or 50 ng/mL of FGF-2. In additional non-limiting examples, the first medium can include about 20 to about 100 ng/mL of BMP-4, such as about 30 to about 90 ng/mL of BMP-4. Thus, the first medium can include about 20, 25, 30, 35, 40, 45, 50, 55, 60, 65, 70, 75, 80, 85, 90, 95 or 100 ng/mL of BMP-4. The medium can be changed, in some non-limiting examples, every day or every other day. Culturing the IPSC in the first medium produces mesendoderm cells.

The mesendoderm cells are then cultured in a second medium comprising an effective amount of activin A, and in the absence of exogenously added FGF-2 and BMP-4, for an amount of time sufficient to produce definitive endoderm cells. In some embodiments, the mesendoderm cells are cultured in the second medium, for about 2 to about 3 days, such as for 2, 2.5 or 3 days, to produce definitive endoderm cells. In some non-limiting examples, the second medium can include, for example, about 50 to about 200 ng/mL activin A, such as about 100 to about 200 ng/mL of activin A. Thus, the first medium can include about 50, 60, 70, 80, 90, 100, 110, 120, 130, 140, 150, 160, 170, 180, 190, or 200 ng/ml of activin A. In additional non-limiting examples, the second medium further comprises an effective amount of L-glutamine. For example, the second medium can include about 0.5 to about 2% volume/volume (v/v) L-glutamine, such as about 0.5%, 1.0%, 1.5% or 2% L-glutamine. The second medium can be changed, for example, every day or every other day.

The definitive endoderm is cultured in a third medium comprising an effective amount of dimethyl sulfoxide (DMSO), and hepatocyte growth factor (HGF). In some embodiments, the third medium comprises about 1 to about 3 percent volume/volume (v/v) DMSO, such as about 1, 1.5, 2, 25, or 3 percent v/v DMSO. In further embodiments, the third medium includes about 20 to about 150 µg/mL of HGF, such as about 50 µg/mL to about 100 µg/mL HGF. In specific, non-limiting examples, the third medium includes about 20, 20, 30, 40, 50, 60, 70, 80, 90, 100, 110, 120, 130, 140, or 150 µg/mL of HGF. In additional non-limiting examples, the third medium further comprises an effective amount of L-glutamine. For example, the third medium can include about 0.5 to about 2% volume/volume (v/v) L-glutamine, such as about 0.5%, 1.0%, 1.5% or 2% L-glutamine. Generally, the third medium is a low glucose medium e.g. it includes 0.2 to 2 grams/liter glucose. The definitive endoderm is cultured in the third medium for about eight to about 14 days, such as for about 8, 9, 10, 11, 12, 13, or 14 days, to produce hepatic-specified cells (Stage 3). The third medium can be replenished every day, or every other day.

In some embodiments, the hepatic-specified cells are transplanted into an immunocompromised animal, see below. Thus the hepatic-specified cells differentiate into hepatocytes in the immunocompromised animal, and are also expanded in the immunocompromised animal.

Optionally, the hepatic-specified cells are cultured in a fourth medium comprising an effective amount of HGF, urso deoxycholic acid, cholesterol, palmitic acid, oleic acid, rifampicin, and optionally cholesterol, to produce human iPS cell derived hepatocytes (iHeps). Generally, the fourth medium is a low glucose medium, e.g. it includes about 0.2 to about 2 grams/liter glucose. The fourth medium can be replenished every day, or every other day.

In some embodiments, the fourth medium includes about 20 to about 150 µg/mL of HGF, such as about 50 µg/mL to about 100 µg/mL HGF. In specific, non-limiting examples, the fourth medium includes about 20, 20, 30, 40, 50, 60, 70, 80, 90, 100, 110, 120, 130, 140, or 150 µg/mL of HGF. In further embodiments, the fourth medium includes about 50 mM to about 150 mM urso deoxycholic acid, such as about 75 to about 125 mM urso deoxycholic acid, for example, 50, 60, 70, 80, 90, 100, 110, 120, 130, 140, or 150 mM urso deoxycholic acid. In additional embodiments, the fourth medium includes about 10 µM to about 50 µM palmitic acid, such as 20 µM to about 40 µM palmitic acid. In specific non-limiting examples, the fourth medium includes about 10, 15, 20, 25, 30, 35, 40, 45 or 50 µM palmitic acid. In more embodiments, the fourth medium includes about 10 µM to about 50 µM oleic acid, such as 20 µM to about 40 µM oleic acid. In specific non-limiting examples, the fourth medium includes about 10, 15, 20, 25, 30, 35, 40, 45 or 50 µM oleic acid. In even more embodiments, the fourth medium includes about 10 µM to about 50 µM rifampicin, such as 20 µM to about 40 µM rifampicin. In specific non-limiting examples, the fourth medium includes about 10, 15, 20, 25, 30, 35, 40, 45 or 50 µM rifampicin.

In more embodiments, the fourth medium further comprises an effective amount of L-glutamine, DMSO, and/or dexamethasone. For example, the fourth medium can include about 0.5 to about 2% v/v L-glutamine, such as about 0.5%, 1.0%, 1.5% or 2% L-glutamine. In additional examples, the fourth medium includes about 1 to about 3 percent v/v DMSO, such as about 1, 1.5, 2, 2.5, or 3 percent v/v DMSO. In further examples, the fourth medium includes about 0.5 to about 2 mM dexamethasone, such as about 0.5, 1.0, 1.5 or 2 mM dexamethasone.

The above methods can also include expanding the human iHeps in vivo, such as in the liver of an immunocompromised non-human animal. This expansion is disclosed in the section below.

In other embodiments, cells produced by the disclosed methods can be cryopreserved, such as by using a cryopreservative that integrates into the cell membrane can changes its structure, so that the cells are viable when frozen. Exemplary non-limiting examples of a cryopreservative are glycerol and DMSO.

Expansion of Hepatocytes in Mammalian Hosts

The disclosed methods can include transplanting hepatic-specified (Stage 3) cells and/or human iHeps (Stage 4) into an immunocompromised non-human animal. Any immunocompromised non-human animal can be used in the methods disclosed herein. In some specific non-limiting examples, the non-human immunocompromised animal is a rat, mouse, pig or rabbit. The immunocompromised non-human animal can have severe combined immunodeficiency (SCID) mouse or rat, or can be a nude mouse or rat. In other examples, the immunocompromised animal is a fumarylaetoacetate hydrolase (FAH) deficient mice, rat and/or pig, see Patent Application number PCT/US2008/065937; also U.S. patent application Ser. No. 14/241,316 and U.S. Pat. No. 9,000,257, all incorporated herein by reference.

The hepatic-specified cells and/or human iHeps can be transplanted into any tissue, using any suitable means known in the art. In one embodiment, the harvested human hepatic-specified cells and/or iHeps are transplanted, such as by injection, into the spleen of the recipient animal. In another embodiment, the expanded human mature hepatocytes (after Stage 5) are transplanted into the liver of the recipient animal.

Human hepatic-specified cells and/or iHeps are retained in the recipient animal for a period of time sufficient to permit production and expansion of human mature hepatocytes. The precise period of time for expansion can be determined empirically with routine experimentation. In one embodiment, the human hepatocytes are allowed to expand for up to six months. In another embodiment, the human mature hepatocytes are allowed to expand for at least about four weeks, at least about six weeks, at least about 8 weeks, at least about 12 weeks, at least about 16 weeks, at least about 20 weeks, at least about 24 weeks, at least about 28 weeks, at least about 36 weeks, at least about 48 weeks, at least about 72 weeks and at least about 96 weeks. The extent of human hepatocytes expansion can vary. In some embodiments, expansion of human hepatocytes in a recipient rat results in an increase of at least about 10-fold, at least about 50-fold, at least about 100-fold, at least about 150-fold, at least about 200-fold, at least about 250-fold, at least about 300-fold, at least about 400-fold, at least about 500-fold or at least about 1000-fold.

Successful engraftment, maturation and expansion of human hepatocytes in the liver requires an immunocompromised animal with some degree of liver dysfunction. Mice livers have been repopulated with human hepatocytes in a variety of different types of immunocompromised mice, including RAG-2 knockout or SCID mice, both of which lack B cells and T cells (U.S. Pat. No. 6,509,514; PCT Publication No. WO 01/07338; U.S. Publication No. 2005-0255591, incorporated herein by reference). Several groups engrafted and expanded primary human hepatocytes in rodents (U.S. Pat. No. 6,509,514; PCT Publication No. WO 01/07338; U.S. Publication No. 2005-0255591). Dandri et al. (*Hepatology* 33:981-988, 2001) reported successful repopulation of mouse livers with human hepatocytes. Since then, other groups have reported successful engraftment of human liver cells in mice. In addition, PCT Publication No. 2008/151283, incorporated herein by reference discloses Fah deficient animals and their use for expanding hepatocytes.

In some embodiments, the recipient is treated with an agent to inhibit growth response of native liver cells in the animal. The factor can be, for example, radiation or retrorsine or tyrosine kinase inhibitor antineoplastic agents such as but not limited; sorafenib or alkylating antineoplastic agents such as but not limited; cisplatin. Briefly, an effective amount of the agent is administered to the recipient for a sufficient amount of time to inhibit growth response of the recipients' liver cells, prior to transplanting human hepatocytes into the recipient.

A double mutant rat deficient for recombinase activating gene 2 (Rag2) and the common gamma chain of the interleukin receptor (Il2rg), provide an efficient in vivo system for expanding human hepatic-specified cells and/or human iHeps and/or human hepatocytes and/or human fetal hepatocytes in vivo. Thus, some embodiments, the immunocompromised non-human animal is a $Rag2^{-/-}/Il2rg^{-/-}$ animal, such as a mouse or a rat. In some non-limiting examples, the present methods can utilize rats that are deficient for $Rag2^{-/-}$ $Il2rg^{-/-}$.

In one embodiment, the rat is a $Rag2^{-/-}/Il2rg^{-/-}$ rat which also includes a nucleic acid molecule encoding Caspase 9 (Casp9). An exemplary Casp9 amino acid sequence is disclosed in GENBANK® Accession No. NM001229, Jan. 20, 2017, incorporated herein by reference. The nucleic acid encoding Casp9 can be operably linked to a promoter expressed in the liver (a liver specific promoter), such as, but not limited to, an albumin or transthyretin promoter and/or alpha-1-antitrypsin promoter. Non-limiting examples of liver-specific promoters are provided on the Liver Specific Gene Promoter Database (LSPD, rulai.cshl.edu/LSPD/), and include, for example, the transthyretin (TTR) promoter or TTR-minimal promoter (TTRm), the alpha 1-antitrypsin (AAT) promoter, the albumin (ALB) promotor or minimal promoter, the apolipoprotein A1 (APOA1) promoter or minimal promoter, the complement factor B (CFB) promoter, the ketohexokinase (KHK) promoter, the hemopexin (H4PX) promoter or minimal promoter, the nicounatmide N-methyltransferase (NNMT) promoter or minimal promoter, the (liver) carboxylesterase 1 (CES1) promoter or minimal promoter, the protein C (PROC) promoter or minimal promoter, the apolipoprotein C3 (APOC3) promoter or minimal promoter, the mannan-binding lectin serine protease 2 (MASP2) promoter or minimal promoter, the hepcidin antimicrobial peptide (HAMP) promoter or minimal promoter, and the serpin peptidase inhibitor, clade C (antithrombin), member 1 (SERPINC1) promoter or minimal promoter. These promoters confer a significant degree of liver specific expression in vivo (and/or in hepatocytes/hepatic cell lines in vitro) of the transgene. In some embodiments, the promoter can also be operably linked to a nucleic acid encoding an FK506 binding protein, such as FKBP12. Selective apotosis can be included, see Di Stasi et al., N Engl J Med. 2011 3; 365(18):1673-83 and PCT Publication No. WO2011146862, both incorporated herein by reference.

It is described herein that an immunocompromised rat ($Rag2^{-/-}/Il2rg^{-/-}$) that includes a gene encoding exogenous Casp9 can be used for engraftment and expansion of human hepatic-specified cells and/or human iHeps and/or human mature iHepatocytes and/or human fetal hepatocytes and/or human adult hepatocytes in vivo.

In some embodiments, the transgenic rats include a liver specific-tissue promoter operably linked to a nucleic acid encoding a fusion protein, specifically an FK506 binding protein (FKBP), such as FKBP12, fused to Caspase 9 (Casp9, GENBANK® Accession No., NM001229, Feb. 11, 2017, incorporated herein by reference). FKBP 12 (e.g., GENBNAK® No. AH002818, Feb. 11, 2017, incorporated herein by reference) can be directly fused to Casp9, or linker can be included between the FKBP12 and the Casp9. The linker can be, for example, 4-10 amino acids in length, such as 4, 5, 6, 7, 8, 9, or 10 amino acids in length. Suitable linkers are known in the art. In a specific non-limiting example, the liver specific promoter, is the albumin promoter and/or transthyretin promoter and/or alpha-1-antitrypsin promoter.

Caspase-9 is a member of caspase family of cysteine proteases that have been implicated in apoptosis and cytokine processing. When cells receive apoptotic stimuli, mitochondria releases cytochrome c which then binds to Apaf-1, the mammalian Ced-4 homologue, together with dATP. The human 12 kDa FK506-binding protein with an F36 to V substitution, the complete mature coding sequence, provides a binding site for synthetic dimerizer drug AP1903 (see Jemal, A. et al., CA Cancer J. Clinic. 58, 71-96 (2008); Scher, H. I. and Kelly, W. K., Journal of Clinical Oncology 11, 1566-72 (1993), incorporated herein by reference).

One specific non-limiting example of a plasmid of use is pEALB123-iCasp9_IRES-GFP, disclosed herein. The pEALB123-iCasp9_IRES-GFP plasmid was constructed by cloning the rat promoter/enhancer sequence of albumin/a fetoprotein from the plasmid pEALB123CAT (Wen and Locker, DNA Cell Biol 1995, 14:267-72, incorporated herein by reference with the FKBP12(V36)-p30Caspase9 sequence from the plasmid pMSCV-F-del Casp9.IRES.GFP 2 Addgene Plasmid #15567, see Straathof et al., Blood 2005, 105:4247-54, incorporated herein by reference). The rat albumin promoter used in this plasmid is only expressed in rat hepatocytes, ensuring that only rat hepatocytes can express the FKBP12(V36)-p30Caspase9 sequence. This modified Caspase 9 system is fused to a modified FK-binding protein, allowing conditional dimerization in the presence 5 of an inducing compound. The sequence used from the pEALB123CAT is:

(SEQ ID NO: 8)

TGAAAGACCCCACCTGTAGGTTTGGCAAGCTAGCTTAAGTAACGCCATTTTGCAAGGC

ATGGAAAATACATAACTGAGAATAGAGAAGTTCAGATCAAGGTTAGGAACAGAGAGA

CAGCAGAATATGGGCCAAACAGGATATCTGTGGTAAGCAGTTCCTGCCCCGGCTCAGG

GCCAAGAACAGATGGTCCCCAGATGCGGTCCCGCCCTCAGCAGTTTCTAGAGAACCAT

CAGATGTTTCCAGGGTGCCCCAAGGACCTGAAAATGACCCTGTGCCTTATTTGAACTA

ACCAATCAGTTCGCTTCTCGCTTCTGTTCGCGCGCTTCTGCTCCCCGAGCTCAATAAAA

GAGCCCACAACCCCTCACTCGGCGCGCCAGTCCTCCGATAGACTGCGTCGCCCGGGTA

CCCGTATTCCCAATAAAGCCTCTTGCTGTTTGCATCCGAATCGTGGACTCGCTGATCCT

TGGGAGGGTCTCCTCAGATTGATTGACTGCCCACCTCGGGGGTCTTTCATTTGGAGGTT

CCACCGAGATTTGGAGACCCCTGCCTAGGGACCACCGACCCCCCGCCGGGAGGTAAG

CTGGCCAGCGGTCGTTTCGTGTCTGTCTCTGTCTTTGTGCGTGTTTGTGCCGGCATCTAA

TGTTTGCGCCTGCGTCTGTACTAGT

CCGCGGACACTGCTGTAACTCTCCTTGACCTATATCGATGTTCTAGTGTACCTTTATTG

ACTTTGACATATTTCTGTCCTTTTAAGTTCGGCGGGCAGCTCGGTTGCTCAATTCGTCTC

TGGACTCTTTTACTTTGTTCCTGTGTGGGGAAGAAAAATATTTTCTCCTCTAAACAC

CAAAGATCCAAAGATAAAATTCCTTTGATGGAGGGAAAACAGCCCCCCTTCCCCATTT

TGATTTTCTTTCGAGCGAAACATGTTCACAGCCAACGGGGAGGGTAAAGGATTCCCCC

CCCCGCCCAGATAGGCTCGAATTAAACAAAGGAGGGAGAGTTGACAGAAACCAACCA

AGGGGAGGATTATGGTGACGTCTGGGGCTAGATGTGAAGAGATCAAGGAAGAAACCA

GCAGAGAAGACATTGGTCAGGCTTGTCATGAGCAGTGTGATGGTGCCTATACATTTTC

ATGCTGGGCAGAAACATCTTTCCACATTTGACCTCCAGTTCCTTGATGTAATCATATGT

TTGGGGTTCCTTGAGAAAGTGTGGGGAGAGTCTTCATATATTAGCTCAAGGAACATGT

ATAGAATAGGTAGAGAGAATTTAGCAGCATTAGGGAAACAGACAAAGAAACGTCAG

GCAAACTGTGGGCTGCCCTCTCAATCCTTGAGTTCCCAGTAATTTAGAGACTATAACAG

TCACGAGATCGTTCTCTGCTCACAGATAACAAGAGCAGGGGGTAAGTGTAACAAAATC

TTCAGAGTAAGGAGGGCCATAGTGGTCTAAAACACTCCTTATAGTTGGAGTGCGTCGC

-continued

```
TTTGCAGGGTTCATTTGAAAATCTGAAGGTTTCCTTGCGAGACGCTAGATTCCATACCA
TTCTCACATATGCTTTTGTGCCTGTGGAGTTTCAGACCTAGATAAGAGAATGATTGAAT
ATTTCACTAACGTTCTGTTACCAGAAGAGCGTGAGAGGCGTGTGATTCATTTGTGGGC
GTAAATCGCTGACTACCATTTGATTCGATGACATTTGATTTCTGTTTGTAAAGATGATG
CTGTGTTTCGGATGTTGTGCTAAGCACCATGGTAAATGCAAGAAGTTAATCATCTGGG
AAAGGGCCAGATTGCCTCCCAGAAGACTGGGACTTAAGGGCACACATGAAGTTCCCTG
AGAAGTCAATCTAGAGAGTGTTAGAAGTTGTCAGAGAGGGACCTTCTCTAGTGAGTGC
TAAACACCCACAGACAATTATATGATCGATGCCTTGAGAACTGGTGGTAAGTTATTAT
AAGCATTGAAGGGCAAGGCACTAGAAATGTAAGAACTATGCTTTCATGGAACACACA
CACAGACACACACACAGATACCCACATGCACACACACACACATGCACACGCACACAG
ACACACACATACACACAGACATACATACACACACAGCACATACACACATACATACATG
CACACACAGAGAGCAAGCACACACAGAGAGAGTCATACACACACACACACAAACACA
CAAACACACAAACACACAAGCAGACACAAACAGACACAGCAAAAAGGATCCTGAAG
GAGTGAAAGTCATTTTCTGCCAACTCACATGTGCAGTCTAACTGTGCATTCTAGAAGTG
CCAGTCCTAAGAATGGTGATATTTACTCACACCTTTTTAGAAATATTTGTAGCTGTCCA
GCATTTAGGACACACCACTCCGCCTCCACACATGAAAGTATACTTTCAGAGAAGTATT
ATTTTGTGAGATGAATCATAAGACTCAGAATCAGTCATGTTAAATTATTCACCGAATGT
CATAGGACTGATAACTGGCACACACACGATTAGCATCTTCTGATGGCGGGGTTCAGTT
TACCGGGTCACGCTGCACTGGGGAAGATTCGAGGATTTATGGAAAAAGTCAACAGAA
CAAGAATTGGAGCAGCCGGAAAGTATTTGCTGCGAACTCTGTACTTAGGACTTAGCTT
TGAGCAATAGCCCCGAAAGGTTTTAGCACTGTTTGCGGTCAGCACACAAACCGTGGTT
CAAAGCTCCTCCTTATCTCTTCCTGCGGCATTTGCCGTCTCTGGTTCTGCACACGGTTTC
TCACCCGCTCCCACACACCTACACTAAGCCCTGTAAGCTGGAGCTATTCCAGTATCCAT
CCCCTCTGTGTGATTCTGGAGATAGGAAGCAATACACCAGTGCCTGTCAACTTCTTCGA
TCTGCAAATCAGGGTGTTTGGCCCACAACATTCCTGGGAGTAAAAAGCAAGCTTGGAT
TACATTAACTCACCACATACTAAACCAGAACCAGTAGGGTAAACCAATCTCTGTCTCT
GTCTCTCTGTCTCTCTCCCTCACTCCCTCTTGCTTTCTCTCTAGGAGTCAGTATGTGTGA
ACTTAGCTTTTAAAGCATTTTTTTCTTTAATTTTACTTCATCCACATTACGAAATTTTAT
GTGGATTTCTCACTTCCTGTCAGCGATGCCTTCACCCACGTGGCTTTGTTAGATTACAC
ATTGCAGTAGTTTAATTGGTCTCATCTCTTTTTGACAGCAGCAGAGACATTTTCAAAGG
ACAGAGATGATTTTTTTTTTTACCAGCTCCTCTTTGAGGTCCTTCATGAAGCGGGAAC
ACGAGGTCCTTAAGAGACAGCCTGTGCCAGCCTCATCAAAAACACTGCCCCCATTAGG
TTGCCAGTAGGTAAAGCCCTTAGCATCATAGTCTTAGCCACCTGAGTTCCATCTCTGGA
GCTCTCAGAAGAGCGGAGAGAGAGATCAGACTCTACAGGGTTGCCTCTGACTGCCACT
GAGGGTCTGCCAACTTTTTGTGTCATGGGGAGTTGAACCCAGAGCCTCACACAAACTC
GGCGAGCCACGATCCGCTGAGTCCTGCCATTTCTGAACACTGTGTCTCACATATTGCCT
TTCTTCTCATTCCTGAACTACGCTGTTCTCTCCATTAATGGGTCTCTCGCTGTCTTTTAC
AATTCCTCGAGGTAAAAGGCAAGCCTTGCTATTCGGCCTACCTACCAACTTTTCTTTGG
GTCTCTTGGAAATGTGACTTCCTCTAAAAATACCTCACCGGTAGAAAGACACTAGGAG
CTGTTTTCCTTCCACATAGCAGGACATCCATCAGAGAACTTGGATACAGTGGATGCAG
```

-continued

```
TCATTTTTCCACCAGATGAGATGTGGTCTCAGTCAGTAATGCTGACACTCATTGCTGAC
ACTTCCCTTCAGTGAACAACATCTCATATGCGGACTTCACACTTTTTGTTGAATGAATC
ATGGAACCCCCAACTGTTGAGTTCTACTTGGTGGCGGCCCTATTCTGAGTGACCCTCTT
ACTAGTTTATCTAACCCTCGTTTATTAAAAAGGATATTAATTTTCGTAACTATAATTTTT
ATATGTTGGGAGTAAAACCATTTTGAGTGTTTTGTCCAATGTCACCTGACCGACAGTTT
GAATAGTCGGGGGTAGAGCCTTTCGTATACTAAAGTCCAGTTTGTTTAACCATATTGCT
TCAGTGGGGTTTCATGGGCTCAGGAAGTAACGAATGAACCAGACATAGAGCTATGAA
AGGTATGTGGTGCGAGCTCAGCCCTTGCGACAAAGCTTTGAGCAACAGCCCGCGTGGG
CTTAGGGTTGTTTGCAGTTGGTGTTAGAGACCTCACACAAAGTCATGTGGCAGATAAC
CCGGAGGCAAAATTCAAACCCAGTCGCCATATGCTCATGTTTAACGGTGACCCTGTGC
ACCTTTCTGATCACATGCTTTGGAATTGCAAAGATCTCCCCACAAGGCAGAGTGCAGA
GAGAATTAAGGATGACATAACCCTGTGGGCTGGGCTGATCTGGGCTGCTCCTCTTGGC
TTAGGTGTAGAAGCATAGCAGTGAATTGGTGACTGATATAACGTGTATTTATTATCTAT
AGTTTTGTGTGTGTGTGTGTGTGTGTGTGTGTGTGTGTGTGTGTGTGTATGATCAT
ATTTACACATGATTCATCTAGCCTTTATGAAAGGATGATGAAACCAGACATTTAGCCTT
GCGGTTACATGCATACTAGCAAGAAACTCGATATAGGATCTTTAAAGGTAGGAAGATC
TCAGAGTGGTCAAGGAGAGGTGTAGCACACCTGTAATCCAGGACCCAGGAGATAGGA
AAATCAGGAACTCAAAGCCAACTGCTCACAAACCGACCATGCAAACGATTGACCAAA
CTAAAATGGAGACTCTTATTTCACTTTAAACCCTTGTCACTGGATAAATACATTCATTA
TCTACTCAGCAAGTGTTGGGTCCTGTCTCAACACTTGACGTGCTATGCATAGTGTAAAA
CGTACTCAGTGTACTTAGACCATTTATTGTTATTTTATCCAATGAGTAGGGATGAGAGG
AGAGGGAGACAGAGACAGAGACAGAGACAGAGACAGAGAGAGACAGAGACAGAGA
GAGACAGAGAGAGACAGAGAGAGACAGAGAGAGACAGAGAGGAGAGAGAGGAG
AGAGATAGAGAGGACAGAGAAGACAGAGAGAAGAGCAGTAGACAGACACACAGAGA
GAGAGAGAGAGAGAGAGAGAGAGAGAGAGAGAGAGAGAGAGAGAGAGAGAGACAG
AGAGAGACAGAGAGAGACAGATAGACACACAGAGAGAGAAAGAGAGGGAGAGA
GAGACACAGAGAGAGAGGTAGACAGACAGACACACATACACACAGACAGACAGACA
GACAGACACACACACAGAGAGAGAGAGAGAGAGAGAGAGAGAGAGAGAGAGAGAG
AGAGAGAGAGAGAGAGAGAGAGAGGTCTGATTTCCCTTGCAATCTAGAAAGTTAA
CGTTAAACTCTGGCCTGTCATTGCTTTGTTCTATTTTGAGAACAGGAAGAAGTGCAGGT
ATGGTCTGATAATAAGGCCTTATTGTGTGTGTTTCTTGGTTTCTATTATTAATATGTTAT
GAAAATCTTTCCATTACATCAACTATTAATCTACAAAATCGGTTTGATAGCGGCATTGC
TCTCCATTTAATGAATACACTATATTTATTTCTGGTGTAAGTCATTTTGTTTTTATAATC
ACATCTTTAAAGTAGCTACTCACAGGCTATGCAGATGACTCAGCTGTTAAGGGCCCTTT
CTGCTCTTCTAGAGGCCCTAGGTTCAATTCCCAGCCCACAGGGCAGCTCATAACCACCT
GTGACTCCAGTTCCGAGGGATCCAATGCCCTCTTCTGACCTCTGCAGCTTCAGATGGCA
AACATACTTAAGGGATTTAGTTAAACAACTTTTTTTTTCGAATTGGCAAGGATCATAT
GATTTTGTAATGGCGCCGGAACCAATGAAATGCTAGCTTAGTGTGGTTAATGATCTAC
CGGTATTGGTTAGAGAAGTATATTATCGCGAGTTTCTCTGCACACAGACCACCTTTCCT
GTCCAGATCTGAGCTTGGCGAGATTTTCAGGAGCTAA
```

The sequence used from the pMSCV-F-del Casp9.IRES.GFP is:

(SEQ ID NO: 9)
```
ATGCTCGAGGGAGTGCAGGTGGAGACTATCTCCCCAGGAGACGGGCGCACCTTCCCCA
AGCGCGGCCAGACCTGCGTGGTGCACTACACCGGGATGCTTGAAGATGGAAAGAAAG
TTGATTCCTCCCGGGACAGAAACAAGCCCTTTAAGTTTATGCTAGGCAAGCAGGAGGT
GATCCGAGGCTGGGAAGAAGGGGTTGCCCAGATGAGTGTGGGTCAGAGAGCCAAACT
GACTATATCTCCAGATTATGCCTATGGTGCCACTGGGCACCCAGGCATCATCCCACCAC
ATGCCACTCTCGTCTTCGATGTGGAGCTTCTAAAACTGGAATCTGGCGGTGGATCCGGA
GTCGACGGATTTGGTGATGTCGGTGCTCTTGAGAGTTTGAGGGGAAATGCAGATTTGG
CTTACATCCTGAGCATGGAGCCCTGTGGCCACTGCCTCATTATCAACAATGTGAACTTC
TGCCGTGAGTCCGGGCTCCGCACCCGCACTGGCTCCAACATCGACTGTGAGAAGTTGC
GGCGTCGCTTCTCCTCGCTGCATTTCATGGTGGAGGTGAAGGGCGACCTGACTGCCAA
GAAAATGGTGCTGGCTTTGCTGGAGCTGGCGCGGCAGGACCACGGTGCTCTGGACTGC
TGCGTGGTGGTCATTCTCTCTCACGGCTGTCAGGCCAGCCACCTGCAGTTCCCAGGGGC
TGTCTACGGCACAGATGGATGCCCTGTGTCGGTCGAGAAGATTGTGAACATCTTCAAT
GGGACCAGCTGCCCCAGCCTGGGAGGGAAGCCCAAGCTCTTTTTCATCCAGGCCTGTG
GTGGGGAGCAGAAAGACCATGGGTTTGAGGTGGCCTCCACTTCCCCTGAAGACGAGTC
CCCTGGCAGTAACCCCGAGCCAGATGCCACCCCGTTCCAGGAAGGTTTGAGGACCTTC
GACCAGCTGGACGCCATATCTAGTTTGCCCACACCCAGTGACATCTTTGTGTCCTACTC
TACTTTCCCAGGTTTTGTTTCCTGGAGGGACCCCAAGAGTGGCTCCTGGTACGTTGAGA
CCCTGGACGACATCTTTGAGCAGTGGGCTCACTCTGAAGACCTGCAGTCCCTCCTGCTT
AGGGTCGCTAATGCTGTTTCGGTGAAAGGGATTTATAAACAGATGCCTGGTTGCTTTAA
TTTCCTCCGGAAAAAACTTTTCTTTAAAACATCAGTCGACTATCCGTACGACGTACCAG
ACTACGCACTCGACTAAGAATTCATCGAGCGGGATCAATTCCGCCCCCCCCCTAACGTT
ACTGGCCGAAGCCGCTTGGAATAAGGCCGGTGTGCGTTTGTCTATATGTTATTTTCCAC
CATATTGCCGTCTTTTGGCAATGTGAGGGCCCGGAAACCTGGCCCTGTCTTCTTGACGA
GCATTCCTAGGGGTCTTTCCCCTCTCGCCAAAGGAATGCAAGGTCTGTTGAATGTCGTG
AAGGAAGCAGTTCCTCTGGAAGCTTCTTGAAGACAAACAACGTCTGTAGCGACCCTTT
GCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTT
GTGGAAAGAGTCAAATGGCTCTCCTCAAGCGTATTCAACAAGGGGCTGAAGGATGCCC
AGAAGGTACCCCATTGTATGGGATCTGATCTGGGGCCTCGGTGCACATGCTTTACATGT
GTTTAGTCGAGGTTAAAAAACGTCTAGGCCCCCCGAACCACGGGACGTGGTTTTCCTT
TGAAAAACACGATAATACCATGGTGAGCAAGGGCGAGGAGCTGTTCACCGGGGTGGT
GCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTGCACCACCG
GCAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCCCG
AAGGCTACGTCCAGGAGCGCACCATCTTCTTCAAGGACGACGGCAACTACAAGACCCG
CGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGC
```

-continued

```
CACAACGTCTATATCATGGCCGACAAGCAGAAGAACGGCATCAAGGTGAACTTCAAGA

TCCGCCACAACATCGAGGACGGCAGCGTGCAGCTCGCCGACCACTACCAGCAGAACAC

CCCCATCGGCGACGGCCCCGTGCTGCTGCCCGACAACCACTACCTGAGCACCCAGTCC

GCCCTGAGCAAAGACCCCAACGAGAAGCGCGATCACATGGTCCTGCTGGAGTTCGTGA

CCGCCGCCGGGATCACTCTCGGCATGGACGAGCTGTACAAGTAAAGCGGCCGCGACTC

TAGAGTCGACCTGCAGGCATGCAAGCTTCAGGTAGCCGGCTAACGTTAACAACCGGTA

CCTCTAGAACTATAGCTAGCATGCGCAAATTTAAAGCGCTGATATCGATAAAATAAAA

GATTTTATTTAGTCTCCAGAAAAAGGGGGGAATGAAAGACCCCACCTGTAGGTTTGGC

AAGCTAGCTTAAGTAACGCCATTTTGCAAGGCATGGAAAATACATAACTGAGAATAGA

GAAGTTCAGATCAAGGTTAGGAACAGAGAGACAGCAGAATATGGGCCAAACAGGATA

TCTGTGGTAAGCAGTTCCTGCCCCGGCTCAGGGCCAAGAACAGATGGTCCCCAGATGC

GGTCCCGCCCTCAGCAGTTTCTAGAGAACCATCAGATGTTTCCAGGGTGCCCCAAGGA

CCTGAAAATGACCCTGTGCCTTATTTGAACTAACCAATCAGTTCGCTTCTCGCTTCTGTT

CGCGCGCTTCTGCTCCCCGAGCTCAATAAAAGAGCCCACAACCCCTCACTCGGCGCGC

CAGTCCTCCGATAGACTGCGTCGCCCGGGTACCCGTGTATCCAATAAACCCTCTTGCAG

TTGCATCCGACTTGTGGTCTCGCTGTTCCTTGGGAGGGTCTCCTCTGAGTGATTGACTA

CCCGTCAGCGGGGGTCTTTCATGGGTAACAGTTTCTTGAAGTTGGAGAACAACATTCTG

AGGGTAGGAGTCGAATATTAAGTAATCCTGACTCAATTAGCCACTGTTTTGAATCCACA

TACTCCAATACTCCGTAAATAGTTCATTATGGACAGCGCAGAAAGAGCTGGGGAGAAT

TGTGAAATTGTTATCCGCTCACAATTCCACACAACATACGAGCCGGAAGCATAAAGTG

TAAAGCCTGGGGTGCCTAATGAGTGAGCTAACTCACATTAATTGCGTTGCGCTCACTGC

CCGCTTTCCAGTCGGGAAACCTGTCGTGCCAGCTGCATTAATGAATCGGCCAACGCGC

GGGGAGAGGCGGTTTGCGTATTGGGCGCTCTTCCGCTTCCTCGCTCACTGACTCGCTGC

GCTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAAAA

GGCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACTA

TAAAGATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTAGC

AGAGCGAGGTATGTAGGCGGTGCTACAGAGTTCTTGAAGTGGTGGCCTAACTACGGCT

ACACTAGAAGGACAGTATTTGGTATCTGCGCTCTGCTGAAGCCAGTTACCTTCGGAAA

AAGAGTTGGTAGCTCTTGATCCGGCAAACAAACCACCGCTGGTAGCGGTGGTTTTTTG

TTTGCAAGCAGCAGATTACGCGCAGAAAAAAAGGATCTCAAGAAGATCCTTTGATCTT

TTCTACGGGGTCTGACGCTCAGTGGAACGAAAACTCACGTTAAGGGATTTTGGTCATG

AGATTATCAAAAAGGATCTTCACCTAGATCCTTTTAAATTAAAAATGAAGTTTTAAATC

AATCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTCCCCGTCGTG
```

```
-continued
TAGATAACTACGATACGGGAGGGCTTACCATCTGGCCCCAGTGCTGCAATGATACCGC

GAGACCCACGCTCACCGGCTCCAGATTTATCAGCAATAAACCAGCCAGCCGGAAGGGC

CGAGCGCAGAAGTGGTCCTGCAACTTTATCCGCCTCCATCCAGTCTATTAATTGTTGCC

GGGAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTAGCTCCTTC

GGTCCTCCGATCGTTGTCAGAAGTAAGTTGGCCGCAGTGTTATCACTCATGGTTATGGC

AGCACTGCATAATTCTCTTACTGTCATGCCATCCGTAAGATGCTTTTCTGTGACTGGTG

AGTACTCAACCAAGTCATTCTGAGAATAGTGTATGCGGCGACCGAGTTGCTCTTGCCCG

GCGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTTC

GATGTAACCCACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGGCGACAC

GGAAATGTTGAATACTCATACTCTTCCTTTTTCAATATTATTGAAGCATTTATCAGGGTT

ATTGTCTCATGAGCGGATACATATTTGAATGTATTTAGAAAAATAAACAAATAGGGGT

TCCGCGCACATTTCCCCGAAAAGTGCCACCTGACGTCTAAGAAACCATTATTATCATGA

CATTAACCTATAAAAATAGGCGTATCACGAGGCCCTTTCGTCTCGCGCGTTTCGGTGAT

GACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTC

GGGGCTGGCTTAACTATGCGGCATCAGAGCAGATTGTACTGAGAGTGCACCATATGCG

GTGTGAAATACCGCACAGATGCGTAAGGAGAAAATACCGCATCAGGCGCCATTCGCCA

TTCAGGCTGCGCAACTGTTGGGAAGGGCGATCGGTGCGGGCCTCTTCGCTATTACGCC

AGCTGGCGAAAGGGGGATGTGCTGCAAGGCGATTAAGTTGGGTAACGCCAGGGTTTTC

CCAGTCACGACGTTGTAAAACGACGGCCAGTGCCANNNNCGCTCTCCCTTATGCGACT

CCTGCATTAGGAAGCAGCCCAGTAGTAGGTTGAGGCCGTTGAGCACCGCCGCCGCAAG

GAATGGTGCATGCAAGGAGATGGCGCCCAACAGTCCCCCGGCCACGGGGCCTGCCACC

ATACCCACGCCGAAACAAGCGCTCATGAGCCCGAAGTGGCGAGCCCGATCTTCCCCAT

CGGTGATGTCGGCGATATAGGCGCCAGCAACCGCACCTGTGGCGCCGGTGATGCCGGC

CACGATGCGTCCGGCGTAGAGGCGATTAGTCCAATTTGTTAAAGACAGGATATCAGTG

GTCCAGGCTCTAGTTTTGACTCAACAATATCACCAGCTGAAGCCTATAGAGTACGAGC

CATAGATAAAATAAAGATTTTATTTAGTCTCCAGAAAA
```

Exemplary amino acid sequences that are encoded are:

iCasp9:
(SEQ ID NO: 10)
MLEGVQVETISPGDGRTFPKRGQTCVVHYTGMLEDGKKVDSSRDRNKPFK
FMLGKQEVIRGWEEGVAQMSVGQRAKLTISPDYAYGATGHPGIIPPHATL
VFDVELLKLESGGGSGVDGFGDVGALESLRGNADLAYILSMEPCGHCLII
NNVNFCRESGLRTRTGSNIDCEKLRRRFSSLHFMVEVKGDLTAKKMVLAL
LELARQDHGALDCCVVVILSHGCQASHLQFPGAVYGTDGCPVSVEKIVNI
FNGTSCPSLGGKPKLFFIQACGGEQKDHGFEVASTSPEDESPGSNPEPDA
TPFQEGLRTFDQLDAISSLPTPSDIFVSYSTFPGFVSWRDPKSGSWYVET
LDDIFEQWAHSEDLQSLLLRVANAVSVKGIYKQMPGCFNFLRKKLFFKTS
VDYPYDVPDYALD GFP:
(SEQ ID NO: 11)
MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN -continued
```
VYIMADKQKNGIKVNFKIRHNIEDGSVQLADHYQQNTPIGDGPVLLPDNH

YLSTQSALSKDPNEKRDHMVLLEFVTAAGITLGMDELYK
```

AmpR:
(SEQ ID NO: 12)
```
MSTFKVLLCGAVLSRIDAGQEQLGRRIHYSQNDLVEYSPVTEKHLTDGMT

VRELCSAAITMSDNTAANLLLTTIGGPKELTAFLHNMGDHVTRLDRWEPE

LNEAIPNDERDTTMPVAMATTLRKLLTGELLTLASRQQLIDWMEADKVAG

PLLRSALPAGWFIADKSGAGERGSRGIIAALGPDKPSRIVVIYTTGSQA

TMDERNRQIAEIGASLIKHW
```

LacZ alpha:
(SEQ ID NO: 13)
```
PFAIQAAQLLGRAIGAGLFAITP
```

Linkers:

Linker between Alb promoter and iCasp9 encoded by:
(SEQ ID NO: 14)
```
ATTACGCCACC
```

Linker between iCasp9 and IRES/GFP:
GA

Linker between iCasp9 and IRES/GFP:
GA

The following components can be included in constructs of use.

MLV-LTR:
(SEQ ID NO: 15)
```
CGTCTGTACTAGT
```

Start alpha fetoprotein enhancer:
(SEQ ID NO: 16)
```
CCGCGGACACTGC
```

Complex 3 enhancer:
(SEQ ID NO: 17)
```
GTGTACCTTTATTGACTTTGACATATTTCTGTCCTTTTAAGTTCGGCGGGCAGCTCGGTT

GCTCAATTCGTCTCTGGACTCTTTTACTTTGTTCCTGTGTGGGGGAAGAAAAAATATTT

TCTCCTCTAAACACCAAAGATCCAAAGATAAAATTCCTTTGATGGAGGGAAAACAGCC
```

Complex 2 enhancer:
(SEQ ID NO: 18)
```
CACACACGATTAGCATCTTCTGATGGCGGGGTTCAGTTTACCGGGTCACGCTGCACTG

GGGAAGATTCGAGGATTTATGGAAAAAGTCAACAGAACAAGAATTGGAGCAGCCGGA

AAGTATTTGCTGCGAACTCTGTACTTAGGACTTAGCTTTGAGCAATAGCCCCGAAAGG

TTTTAGCACTGTTTGCGGTCAGCACACAAACCGTGGTTCAAAGCTCCTCCTTATCTCTT

CCTGC
```

Complex 1 enhancer:
(SEQ ID NO: 19)
```
ATGTCACCTGACCGACAGTTTGAATAGTCGGGGGTAGAGCCTTTCGTATACTAAAGTC

CAGTTTGTTTAACCATATTGCTTCAGTGGGGTTTCATGGGCTCAGGAAGTAACGAATGA

ACCAGACATAGAGCTATGAAAGGTATGTGGTGCGAGCTCAGCCCTTGCGACAAAGCTT

TGAGCAACAGCCCGCGTGGGCTTAGGGTTGTTTGCAGTTGGTGTTAGAGACCTCACAC

AAAGTCATGTGGCAGATAACCCGGAGGCAAAATTCAAACCCAGTCGCCATATGCTCAT

GTTTAACGGTGACCCTGTGCACCTTTCTGATCACATGCTTTGGAATTGCAAAGAT
```

End alpha fetoprotein enhancer:
(SEQ ID NO: 20)
```
TTCTGACCTCTGCAG
```

Alb 123 promoter:
(SEQ ID NO: 21)
```
GCTTCAGATGGCAAACATACTTAAGGGATTTAGTTAAACAACTTTTTTTTTCGAATTG

GCAAGGATCATATGATTTTGTAATGGCGCCGGAACCAATGAAATGCTAGCTTAGTGTG

GTTAATGATCTACCGGTATTGGTTAGAGAAGTATATTATCGCGAGTTTCTCTGCACACA

GACCACCTTTCCTGTCCA
```

HNF1:
(SEQ ID NO: 22)
```
GGTTAATGATCTACC
```

-continued

Tata box:
TATATTAT

Icasp9:
(SEQ ID NO: 23)
ATGCTCGAGGGAGTGCAGGTGGAGACTATCTCCCCAGGAGACGGGCGCACCTTCCCA

AGCGCGGCCAGACCTGCGTGGTGCACTACACCGGGATGCTTGAAGATGGAAAGAAAG

TTGATTCCTCCCGGGACAGAAACAAGCCCTTTAAGTTTATGCTAGGCAAGCAGGAGGT

GATCCGAGGCTGGGAAGAAGGGGTTGCCCAGATGAGTGTGGGTCAGAGAGCCAAACT

GACTATATCTCCAGATTATGCCTATGGTGCCACTGGGCACCCAGGCATCATCCCACCAC

ATGCCACTCTCGTCTTCGATGTGGAGCTTCTAAAACTGGAATCTGGCGGTGGATCCGG

AGTCGACGGATTTGGTGATGTCGGTGCTCTTGAGAGTTTGAGGGGAAATGCAGATTTG

GCTTACATCCTGAGCATGGAGCCCTGTGGCCACTGCCTCATTATCAACAATGTGAACTT

CTGCCGTGAGTCCGGGCTCCGCACCCGCACTGGCTCCAACATCGACTGTGAGAAGTTG

CGGCGTCGCTTCTCCTCGCTGCATTTCATGGTGGAGGTGAAGGGCGACCTGACTGCCA

AGAAAATGGTGCTGGCTTTGCTGGAGCTGGCGCGGCAGGACCACGGTGCTCTGGACTG

CTGCGTGGTGGTCATTCTCTCTCACGGCTGTCAGGCCAGCCACCTGCAGTTCCCAGGGG

CTGTCTACGGCACAGATGGATGCCCTGTGTCGGTCGAGAAGATTGTGAACATCTTCAA

TGGGACCAGCTGCCCCAGCCTGGGAGGGAAGCCCAAGCTCTTTTTCATCCAGGCCTGT

GGTGGGGAGCAGAAAGACCATGGGTTTGAGGTGGCCTCCACTTCCCCTGAAGACGAGT

CCCCTGGCAGTAACCCCGAGCCAGATGCCACCCCGTTCCAGGAAGGTTTGAGGACCTT

CGACCAGCTGGACGCCATATCTAGTTTGCCCACACCCAGTGACATCTTTGTGTCCTACT

CTACTTTCCCAGGTTTTGTTTCCTGGAGGGACCCCAAGAGTGGCTCCTGGTACGTTGAG

ACCCTGGACGACATCTTTGAGCAGTGGGCTCACTCTGAAGACCTGCAGTCCCTCCTGCT

TAGGGTCGCTAATGCTGTTTCGGTGAAAGGGATTTATAAACAGATGCCTGGTTGCTTTA

ATTTCCTCCGGAAAAAACTTTTCTTTAAAACATCAGTCGACTATCCGTACGACGTACCA

GACTACGCACTCGACTAA

IRES:
(SEQ ID NO: 24)
ATTCATCGAGCGGGATCAATTCCGCCCCCCCCTAACGTTACTGGCCGAAGCCGCTTG

GAATAAGGCCGGTGTGCGTTTGTCTATATGTTATTTTCCACCATATTGCCGTCTTTTGGC

AATGTGAGGGCCCGGAAACCTGGCCCTGTCTTCTTGACGAGCATTCCTAGGGGTCTTTC

CCCTCTCGCCAAAGGAATGCAAGGTCTGTTGAATGTCGTGAAGGAAGCAGTTCCTCTG

GAAGCTTCTTGAAGACAAACAACGTCTGTAGCGACCCTTTGCAGGCAGCGGAACCCCC

CACCTGGCGACAGGTGCCTCTGCGGCCAAAAGCCACGTGTATAAGATACACCTGCAAA

GGCGGCACAACCCCAGTGCCACGTTGTGAGTTGGATAGTTGTGGAAAGAGTCAAATGG

-continued

CTCTCCTCAAGCGTATTCAACAAGGGGCTGAAGGATGCCCAGAAGGTACCCCATTGTA

TGGGATCTGATCTGGGGCCTCGGTGCACATGCTTTACATGTGTTTAGTCGAGGTTAAAA

AACGTCTAGGCCCCCCGAACCACGGGGACGTGGTTTTCCTTTGAAAAACACGATAATA

CC

GFP:

(SEQ ID NO: 25)

ATGGTGAGCAAGGGCGAGGAGCTGTTCACCGGGGTGGTGCCCATCCTGGTCGAGCTGG

ACGGCGACGTAAACGGCCACAAGTTCAGCGTGTCCGGCGAGGGCGAGGGCGATGCCA

CCTACGGCAAGCTGACCCTGAAGTTCATCTGCACCACCGGCAAGCTGCCCGTGCCCTG

GCCCACCCTCGTGACCACCCTGACCTACGGCGTGCAGTGCTTCAGCCGCTACCCCGAC

CACATGAAGCAGCACGACTTCTTCAAGTCCGCCATGCCCGAAGGCTACGTCCAGGAGC

GCACCATCTTCTTCAAGGACGACGGCAACTACAAGACCCGCGCCGAGGTGAAGTTCGA

GGGCGACACCCTGGTGAACCGCATCGAGCTGAAGGGCATCGACTTCAAGGAGGACGG

CAACATCCTGGGGCACAAGCTGGAGTACAACTACAACAGCCACAACGTCTATATCATG

GCCGACAAGCAGAAGAACGGCATCAAGGTGAACTTCAAGATCCGCCACAACATCGAG

GACGGCAGCGTGCAGCTCGCCGACCACTACCAGCAGAACACCCCCATCGGCGACGGC

CCCGTGCTGCTGCCCGACAACCACTACCTGAGCACCCAGTCCGCCCTGAGCAAAGACC

CCAACGAGAAGCGCGATCACATGGTCCTGCTGGAGTTCGTGACCGCCGCCGGGATCAC

TCTCGGCATGGACGAGCTGTACAAGTAA

Poly A:

(SEQ ID NO: 26)

TAGAGTCGACCTGCAGGCATGCAAGCTTCAGGTAGCCGGCTAACGTTAACAACCGGTA

CCTCTAGAACTATAGCTAGCATGCGCAAATTTAAAGCGCTGATATCGATAAAATAAAA

GATTTTATTTAGTCTCCAGAAAAAGGGGGGAATGAAAGACCCCACCTGTAGGTTTGGC

AAGCTAGCTTAAGTAACGCCATTTTGCAAGGCATGGAAAATACATAACTGAGAATAGA

GAAGTTCAGATCAAGGTTAGGAACAGAGAGACAGCAGAATATGGGCCAAACAGGATA

TCTGTGGTAAGCAGTTCCTGCCCCGGCTCAGGGCCAAGAACAGATGGTCCCCAGATGC

GGTCCCGCCCTCAGCAGTTTCTAGAGAACCATCAGATGTTTCCAGGGTGCCCCAAGGA

CCTGAAAATGACCCTGTGCCTTATTTGAACTAACCAATCAGTTCGCTTCTCGCTTCTGT

TCGCGCGCTTCTGCTCCCCGAGCTCAATAAAAGAGCCCACAACCCCTCACTCGGCGCG

CCAGTCCTCCG

LacO:

(SEQ ID NO: 27)

AATTGTTATCCGCTCACAATTCC

-continued

ColE1 Origin:

(SEQ ID NO: 28)
GGCCGCGTTGCTGGCGTTTTTCCATAGGCTCCGCCCCCCTGACGAGCATCACAAAAATC

GACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATCT

CAGTTCGGTGTAGGTCGTTCGCTCCAAGCTGGGCTGTGTGCACGAACCCCCCGTTCAGC

CCGACCGCTGCGCCTTATCCGGTAACTATCGTCTTGAGTCCAACCCGGTAAGACACGA

CTTATCGCCACTGGCAGCAGCCACTGGTAACAGGATTAGCAGAGCGAGGTATGTAGGC

GGTGCTACAGAGTTCTTGAAGTGGTGGCCTAACTACGGCTACACTAGAAGGACAGTAT

TTGGTATCTGCGCTCTGCTGAAGCCAGTTACCTTCGGAAAAAGAGTTGGTAGCTCTTGA

TCCGGCAAACAAACCACCGCTGGTAGCGGTGGTTTTTTTGTTTGCAAGCAGCAGATTA

CGCGCAGAAAAAAAGGATCTCAAGAAGATCCTTTGATCTTTTCTACGGGGTCTGACGC

TCAGTGGAACGAAAACTCACGTTAAGGGATTTTGGTCATGA

AmpR:

(SEQ ID NO: 29)
CCAATGCTTAATCAGTGAGGCACCTATCTCAGCGATCTGTCTATTTCGTTCATCCATAG

TTGCCTGACTCCCCGTCGTGTAGATAACTACGATACGGGAGGGCTTACCATCTGGCCCC

AGTGCTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGC

GCAACGTTGTTGCCATTGCTACAGGCATCGTGGTGTCACGCTCGTCGTTTGGTATGGCT

TCATTCAGCTCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGGCCGCAGTG

TTATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCGGC

GACCGAGTTGCTCTTGCCCGGCGTCAATACGGGATAATACCGCGCCACATAGCAGAAC

TTTAAAAGTGCTCAT

LacZ alpha:

(SEQ ID NO: 30)
CCATTCGCCATTCAGGCTGCGCAACTGTTGGGAAGGGCGATCGGTGCGGGCCTCTTCG

CTATTACGCCA

M13-forward:

(SEQ ID NO: 31)
TGTAAAACGACGGCCAGT.

A transgene with the albumin promoter operably linked to a fusion protein including FKBP12 and Casp9 is referred to herein as "ALB-iCasp9." Without being bound by theory, the albumin promoter provides expression in liver cells only. The FKBP12 component provides conditional dimerization, specifically upon treatment of the transgenic animal with a small molecule chemical induce of dimerization, namely AP1903 or AP20187. The chemical formula of AP1903 is C78H98N4O20. The chemical formula of AP20187 is C82H107N5O20. The molecules are shown below.

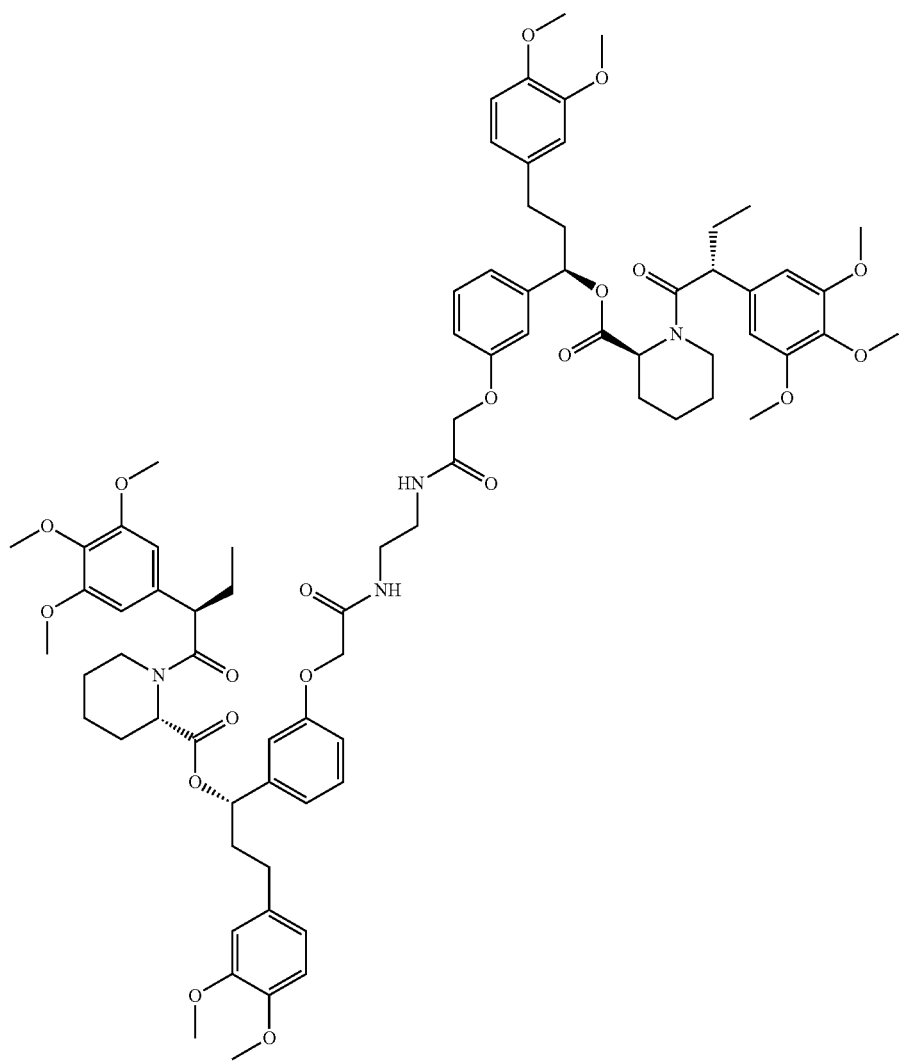

AP20187

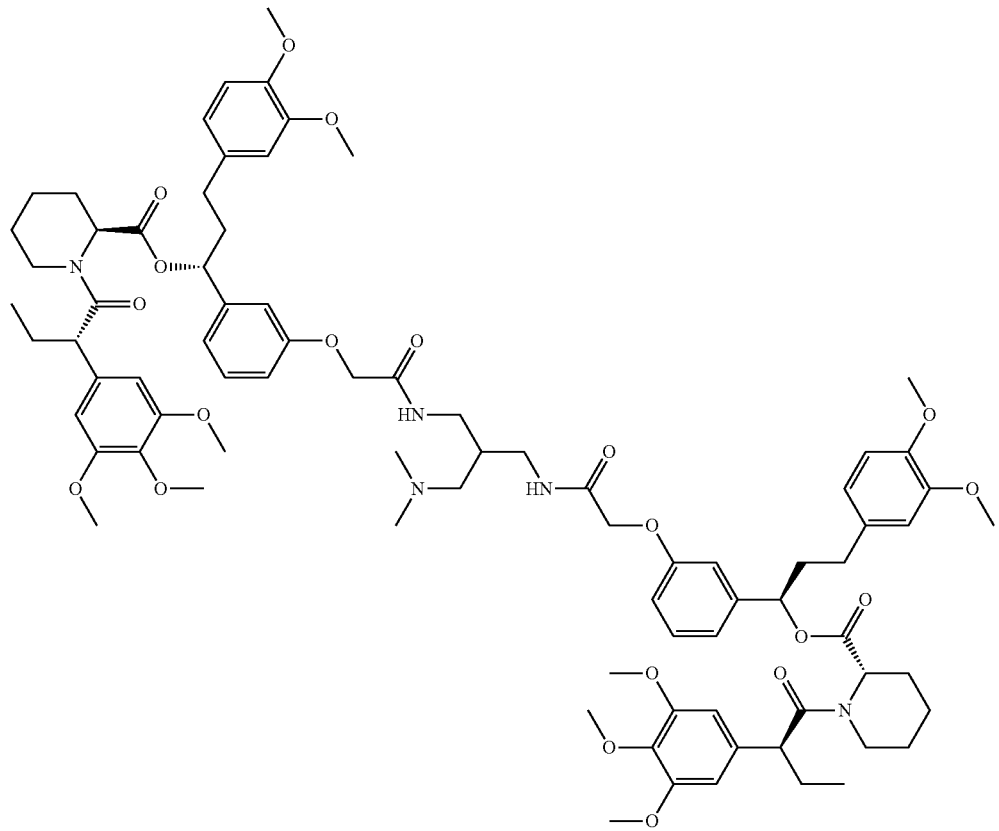

Thus, in some embodiments, a rat that includes a transgene including ALB-iCasp9 is utilized in the disclosed methods. The rat can be, for example, as a Rag2$^{-/-}$/Il2rg$^{-/-}$ rat. In some embodiments, the rat is treated with an effective amount of a chemical inducer of dimerization (AP1903 and/or AP20187), which activates intracytoplasmic caspase-3, directly triggering apoptosis in the recipient rat hepatocytes. The chemical inducer of dimerization (AP1903) can be given by several routes (intraperitoneal, intravenous, intramuscular, subcutaneous and orally). The dose can be, for example, about 0.01 to about 10 mg/kg, such as about 0.1 to about 10 mg/kg, or about 1 to about 10 mg/kg, which can inhibit the growth of rat hepatocytes. Administration and the effects of these compounds is disclosed, for example, in PCT Publication No. WO 2011/146862, incorporated herein by reference)

Figure 13A:
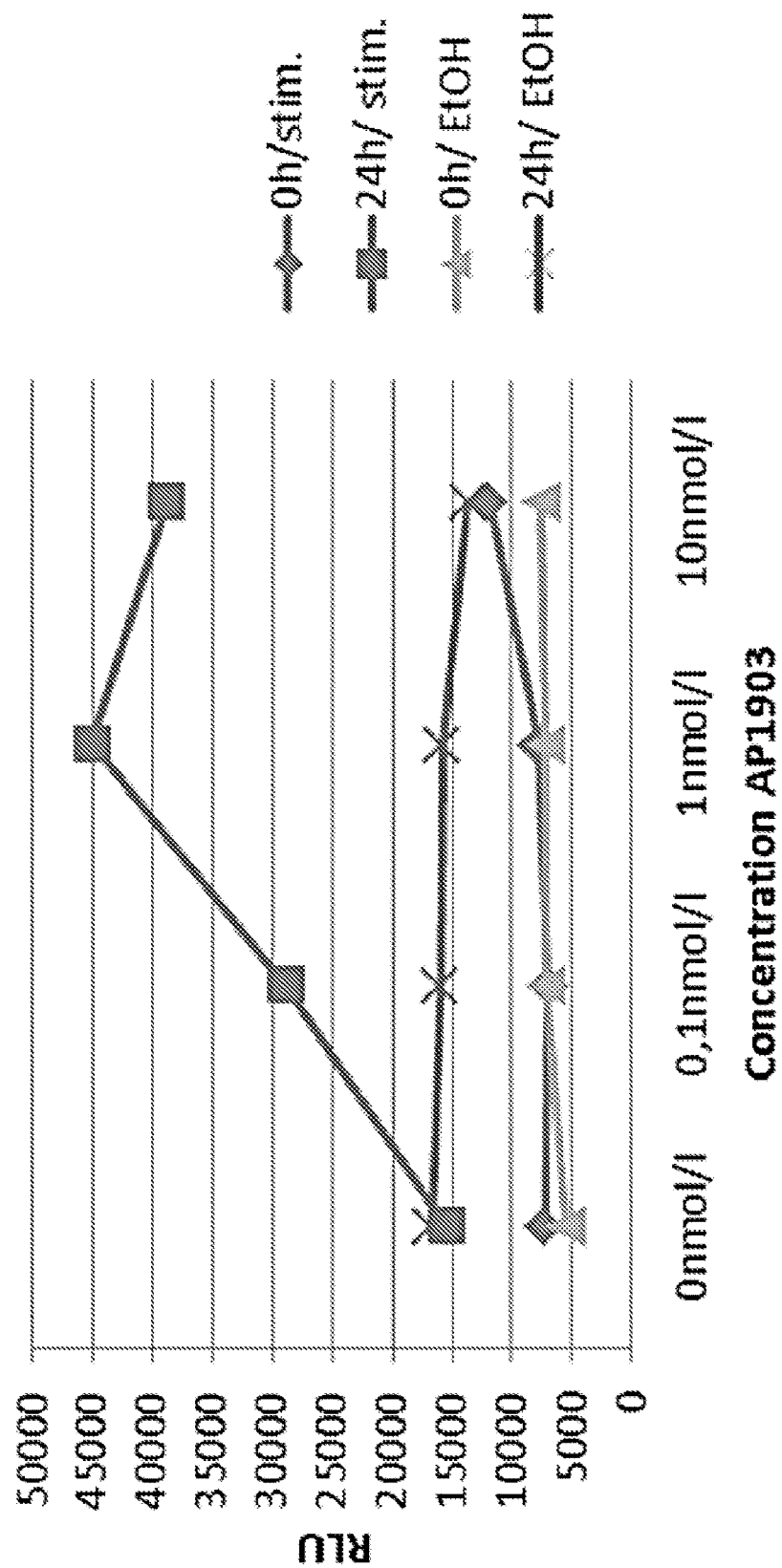
FIGS. 13A-13B (A) In HEK293 cells, the functionality of the Construct could be proven. Compared to Ethanol stimulated Cells, there was an effect of AP1903 in pMSCV-F-del Casp9-IRES-GFP transfected HEK293 cells with a maximum at 1 nmol/l. Untransfected cells but treated with AP1903 did not show any effect, as well as Ethanol treated cells. (B) Then a plasmid has been generated for Casp9-IRES-GFP under the control of the albumin promoter for liver specific expression.
Figure 13B:
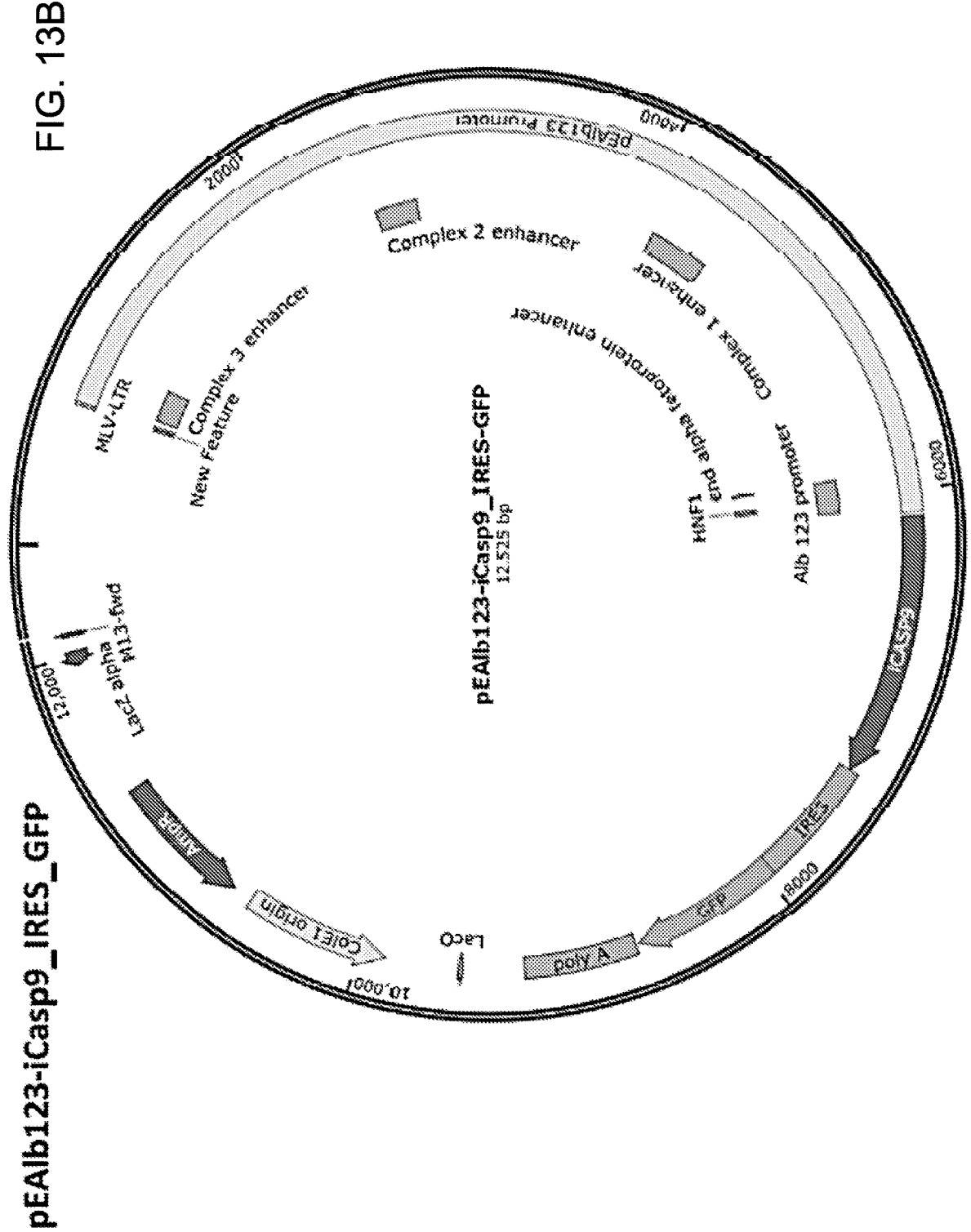
Figure 21:
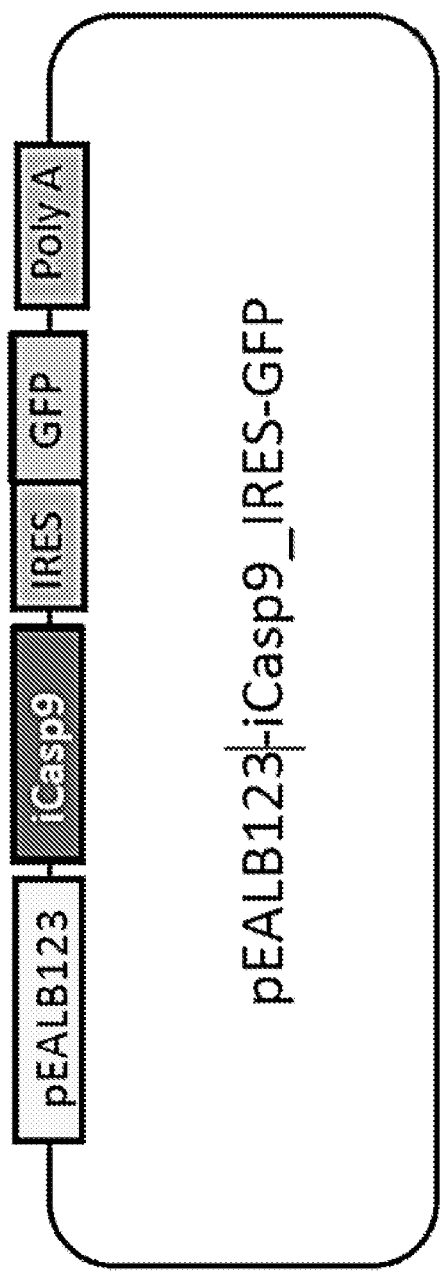
FIG. 21 Schematic diagram of a pEALB123-iCasp9_IRES-GFP plasmid.

FIG. 13B and FIG. 21 show exemplary constructs of use. An exemplary complete nucleic acid sequence is provided below:

(SEQ ID NO: 7)
TGAAAGACCCCACCTGTAGGTTTGGCAAGCTAGCTTAAGTAACGCCATTTTGCAAGGC

ATGGAAAATACATAACTGAGAATAGAGAAGTTCAGATCAAGGTTAGGAACAGAGAGA

CAGCAGAATATGGGCCAAACAGGATATCTGTGGTAAGCAGTTCCTGCCCCGGCTCAGG

GCCAAGAACAGATGGTCCCCAGATGCGGTCCCGCCCTCAGCAGTTTCTAGAGAACCAT

CAGATGTTTCCAGGGTGCCCCAAGGACCTGAAAATGACCCTGTGCCTTATTTGAACTA

ACCAATCAGTTCGCTTCTCGCTTCTGTTCGCGCGCTTCTGCTCCCGAGCTCAATAAAA

GAGCCCACAACCCCTCACTCGGCGCGCCAGTCCTCCGATAGACTGCGTCGCCCGGGTA

CCCGTATTCCCAATAAAGCCTCTTGCTGTTTGCATCCGAATCGTGGACTCGCTGATCCT

TGGGAGGGTCTCCTCAGATTGATTGACTGCCCACCTCGGGGGTCTTTCATTTGGAGGTT

CCACCGAGATTTGGAGACCCCTGCCTAGGGACCACCGACCCCCCGCCGGGAGGTAAG

CTGGCCAGCGGTCGTTTCGTGTCTGTCTCTGTCTTTGTGCGTGTTTGTGCCGGCATCTAA

TGTTTGCGCCTGCGTCTGTACTAGTCCGCGGACACTGCTGTAACTCTCCTTGACCTATA

-continued

```
TCGATGTTCTAGTGTACCTTTATTGACTTTGACATATTTCTGTCCTTTTAAGTTCGGCGG

GCAGCTCGGTTGCTCAATTCGTCTCTGGACTCTTTTACTTTGTTCCTGTGTGGGGGAAG

AAAAAATATTTTCTCCTCTAAACACCAAAGATCCAAAGATAAAATTCCTTTGATGGAG

GGAAAACAGCCCCCCTTCCCCATTTTGATTTTCTTTCGAGCGAAACATGTTCACAGCCA

ACGGGGAGGGTAAAGGATTCCCCCCCCGCCCAGATAGGCTCGAATTAAACAAAGGA

GGGAGAGTTGACAGAAACCAACCAAGGGGAGGATTATGGTGACGTCTGGGGCTAGAT

GTGAAGAGATCAAGGAAGAAACCAGCAGAGAAGACATTGGTCAGGCTTGTCATGAGC

AGTGTGATGGTGCCTATACATTTTCATGCTGGGCAGAAACATCTTTCCACATTTGACCT

CCAGTTCCTTGATGTAATCATATGTTTGGGGTTCCTTGAGAAAGTGTGGGGAGAGTCTT

CATATATTAGCTCAAGGAACATGTATAGAATAGGTAGAGAGAATTTAGCAGCATTAGG

GAAACAGACAAAGAAAACGTCAGGCAAACTGTGGGCTGCCCTCTCAATCCTTGAGTTC

CCAGTAATTTAGAGACTATAACAGTCACGAGATCGTTCTCTGCTCACAGATAACAAGA

GCAGGGGGTAAGTGTAACAAAATCTTCAGAGTAAGGAGGGCCATAGTGGTCTAAAAC

ACTCCTTATAGTTGGAGTGCGTCGCTTTGCAGGGTTCATTTGAAAATCTGAAGGTTTCC

TTGCGAGACGCTAGATTCCATACCATTCTCACATATGCTTTTGTGCCTGTGGAGTTTCA

GACCTAGATAAGAGAATGATTGAATATTTCACTAACGTTCTGTTACCAGAAGAGCGTG

AGAGGCGTGTGATTCATTTGTGGGCGTAAATCGCTGACTACCATTTGATTCGATGACAT

TTGATTTCTGTTTGTAAAGATGATGCTGTGTTTCGGATGTTGTGCTAAGCACCATGGTA

AATGCAAGAAGTTAATCATCTGGGAAAGGGCCAGATTGCCTCCCAGAAGACTGGGACT

TAAGGGCACACATGAAGTTCCCTGAGAAGTCAATCTAGAGAGTGTTAGAAGTTGTCAG

AGAGGGACCTTCTCTAGTGAGTGCTAAACACCCACAGACAATTATATGATCGATGCCT

TGAGAACTGGTGGTAAGTTATTATAAGCATTGAAGGGCAAGGCACTAGAAATGTAAG

AACTATGCTTTCATGGAACACACACACAGACACACACACAGATACCCACATGCACACA

CACACACATGCACACGCACACAGACACACACATACACACAGACATACATACACACAC

AGCACATACACACATACATACATGCACACACAGAGAGCAAGCACACACAGAGAGAGT

CATACACACACACACAAACACACAAACACACAAACACACAAGCAGACACAAACAG

ACACAGCAAAAAGGATCCTGAAGGAGTGAAAGTCATTTTCTGCCAACTCACATGTGCA

GTCTAACTGTGCATTCTAGAAGTGCCAGTCCTAAGAATGGTGATATTTACTCACACCTT

TTTAGAAATATTTGTAGCTGTCCAGCATTAGGACACACCACTCCGCCTCCACACATGA

AAGTATACTTTCAGAGAAGTATTATTTTGTGAGATGAATCATAAGACTCAGAATCAGT

CATGTTAAATTATTCACCGAATGTCATAGGACTGATAACTGGCACACACACGATTAGC

ATCTTCTGATGGCGGGGTTCAGTTTACCGGGTCACGCTGCACTGGGGAAGATTCGAGG

ATTTATGGAAAAAGTCAACAGAACAAGAATTGGAGCAGCCGGAAAGTATTTGCTGCG

AACTCTGTACTTAGGACTTAGCTTTGAGCAATAGCCCCGAAAGGTTTTAGCACTGTTTG

CGGTCAGCACACAAACCGTGGTTCAAAGCTCCTCCTTATCTCTTCCTGCGGCATTTGCC

GTCTCTGGTTCTGCACACGGTTTCTCACCCGCTCCCACACACCTACACTAAGCCCTGTA

AGCTGGAGCTATTCCAGTATCCATCCCCTCTGTGTGATTCTGGAGATAGGAAGCAATA

CACCAGTGCCTGTCAACTTCTTCGATCTGCAAATCAGGGTGTTTGGCCCACAACATTCC

TGGGAGTAAAAAGCAAGCTTGGATTACATTAACTCACCACATACTAAACCAGAACCAG

TAGGGTAAACCAATCTCTGTCTCTGTCTCTCTGTCTCTCTCCCTCACTCCCTCTTGCTTT
```

-continued
```
CTCTCTAGGAGTCAGTATGTGTGAACTTAGCTTTTAAAGCATTTTTTCTTTAATTTTAC
TTCATCCACATTACGAAATTTTATGTGGATTTCTCACTTCCTGTCAGCGATGCCTTCACC
CACGTGGCTTTGTTAGATTACACATTGCAGTAGTTTAATTGGTCTCATCTCTTTTTGACA
GCAGCAGAGACATTTTCAAAGGACAGAGATGATTTTTTTTTTTACCAGCTCCTCTTTG
AGGTCCTTCATGAAGCGGGAACACGAGGTCCTTAAGAGACAGCCTGTGCCAGCCTCAT
CAAAAACACTGCCCCCATTAGGTTGCCAGTAGGTAAAGCCCTTAGCATCATAGTCTTA
GCCACCTGAGTTCCATCTCTGGAGCTCTCAGAAGAGCGGAGAGAGAGATCAGACTCTA
CAGGGTTGCCTCTGACTGCCACTGAGGGTCTGCCAACTTTTTGTGTCATGGGGAGTTGA
ACCCAGAGCCTCACACAAACTCGGCGAGCCACGATCCGCTGAGTCCTGCCATTTCTGA
ACACTGTGTCTCACATATTGCCTTTCTTCTCATTCCTGAACTACGCTGTTCTCTCCATTA
ATGGGTCTCTCGCTGTCTTTTACAATTCCTCGAGGTAAAAGGCAAGCCTTGCTATTCGG
CCTACCTACCAACTTTTCTTTGGGTCTCTTGGAAATGTGACTTCCTCTAAAAATACCTC
ACCGGTAGAAAGACACTAGGAGCTGTTTTCCTTCCACATAGCAGGACATCCATCAGAG
AACTTGGATACAGTGGATGCAGTCATTTTTCCACCAGATGAGATGTGGTCTCAGTCAGT
AATGCTGACACTCATTGCTGACACTTCCCTTCAGTGAACAACATCTCATATGCGGACTT
CACACTTTTTGTTGAATGAATCATGGAACCCCCAACTGTTGAGTTCTACTTGGTGGCGG
CCCTATTCTGAGTGACCCTCTTACTAGTTTATCTAACCCTCGTTTATTAAAAAGGATATT
AATTTTCGTAACTATAATTTTTATATGTTGGGAGTAAAACCATTTTGAGTGTTTTGTCCA
ATGTCACCTGACCGACAGTTTGAATAGTCGGGGGTAGAGCCTTTCGTATACTAAAGTC
CAGTTTGTTTAACCATATTGCTTCAGTGGGGTTTCATGGGCTCAGGAAGTAACGAATGA
ACCAGACATAGAGCTATGAAAGGTATGTGGTGCGAGCTCAGCCCTTGCGACAAAGCTT
TGAGCAACAGCCCGCGTGGGCTTAGGGTTGTTTGCAGTTGGTGTTAGAGACCTCACAC
AAAGTCATGTGGCAGATAACCCGGAGGCAAAATTCAAACCCAGTCGCCATATGCTCAT
GTTTAACGGTGACCCTGTGCACCTTTCTGATCACATGCTTTGGAATTGCAAAGATCTCC
CCACAAGGCAGAGTGCAGAGAGAATTAAGGATGACATAACCCTGTGGGCTGGGCTGA
TCTGGGCTGCTCCTCTTGGCTTAGGTGTAGAAGCATAGCAGTGAATTGGTGACTGATAT
AACGTGTATTTATTATCTATAGTTTTGTGTGTGTGTGTGTGTGTGTGTGTGTGTGT
GTGTGTGTGTGTATGATCATATTTACACATGATTCATCTAGCCTTTATGAAAGGATGAT
GAAACCAGACATTTAGCCTTGCGGTTACATGCATACTAGCAAGAAACTCGATATAGGA
TCTTTAAAGGTAGGAAGATCTCAGAGTGGTCAAGGAGAGGTGTAGCACACCTGTAATC
CAGGACCCAGGAGATAGGAAAATCAGGAACTCAAAGCCAACTGCTCACAAACCGACC
ATGCAAACGATTGACCAAACTAAAATGGAGACTCTTATTTCACTTTAAACCCTTGTCAC
TGGATAAATACATTCATTATCTACTCAGCAAGTGTTGGGTCCTGTCTCAACACTTGACG
TGCTATGCATAGTGTAAAACGTACTCAGTGTACTTAGACCATTTATTGTTATTTTATCC
AATGAGTAGGGATGAGAGGAGAGGGAGACAGAGACAGAGACAGAGACAGAGACAGA
GAGAGACAGAGACAGAGAGACAGAGAGACAGAGAGACAGAGAGAGAC
AGAGAGGAGAGAGAGGAGAGAGATAGAGAGGACAGAGAAGACAGAGAGAAGAGCA
GTAGACAGACACACAGAGAGAGAGAGAGAGAGAGAGAGAGAGAGAGAGAGAGA
GAGAGAGAGAGAGACAGAGAGACAGAGAGAGACAGATAGACACACAGAGA
GAGAAAGAGAGGGAGAGAGAGACACAGAGAGAGAGGTAGACAGACAGACACACATA
CACACAGACAGACAGACAGACAGACACACACACAGAGAGAGAGAGAGAGAGA
```

-continued

```
GAGAGAGAGAGAGAGAGAGAGAGAGAGAGAGAGAGAGAGAGGTCTGATTTCCCT

TGCAATCTAGAAAGTTAACGTTAAACTCTGGCCTGTCATTGCTTTGTTCTATTTTGAGA

ACAGGAAGAAGTGCAGGTATGGTCTGATAATAAGGCCTTATTGTGTGTGTTTCTTGGTT

TCTATTATTAATATGTTATGAAAATCTTTCCATTACATCAACTATTAATCTACAAAATC

GGTTTGATAGCGGCATTGCTCTCCATTTAATGAATACACTATATTTATTTCTGGTGTAA

GTCATTTTGTTTTTATAATCACATCTTTAAAGTAGCTACTCACAGGCTATGCAGATGAC

TCAGCTGTTAAGGGCCCTTTCTGCTCTTCTAGAGGCCCTAGGTTCAATTCCCAGCCCAC

AGGGCAGCTCATAACCACCTGTGACTCCAGTTCCGAGGGATCCAATGCCCTCTTCTGA

CCTCTGCAGCTTCAGATGGCAAACATACTTAAGGGATTTAGTTAAACAACTTTTTTTTT

TCGAATTGGCAAGGATCATATGATTTTGTAATGGCGCCGGAACCAATGAAATGCTAGC

TTAGTGTGGTTAATGATCTACCGGTATTGGTTAGAGAAGTATATTATCGCGAGTTTCTC

TGCACACAGACCACCTTTCCTGTCCAGATCTGAGCTTGGCGAGATTTTCAGGAGCTAA

ATTACGCCACCATGCTCGAGGGAGTGCAGGTGGAGACTATCTCCCCAGGAGACGGGCG

CACCTTCCCCAAGCGCGGCCAGACCTGCGTGGTGCACTACACCGGGATGCTTGAAGAT

GGAAAGAAAGTTGATTCCTCCCGGGACAGAAACAAGCCCTTTAAGTTTATGCTAGGCA

AGCAGGAGGTGATCCGAGGCTGGGAAGAAGGGGTTGCCCAGATGAGTGTGGGTCAGA

GAGCCAAACTGACTATATCTCCAGATTATGCCTATGGTGCCACTGGGCACCCAGGCAT

CATCCCACCACATGCCACTCTCGTCTTCGATGTGGAGCTTCTAAAACTGGAATCTGGCG

GTGGATCCGGAGTCGACGGATTTGGTGATGTCGGTGCTCTTGAGAGTTTGAGGGGAAA

TGCAGATTTGGCTTACATCCTGAGCATGGAGCCCTGTGGCCACTGCCTCATTATCAACA

ATGTGAACTTCTGCCGTGAGTCCGGGCTCCGCACCCGCACTGGCTCCAACATCGACTGT

GAGAAGTTGCGGCGTCGCTTCTCCTCGCTGCATTTCATGGTGGAGGTGAAGGGCGACC

TGACTGCCAAGAAAATGGTGCTGGCTTTGCTGGAGCTGGCGCGGCAGGACCACGGTGC

TCTGGACTGCTGCGTGGTGGTCATTCTCTCTCACGGCTGTCAGGCCAGCCACCTGCAGT

TCCCAGGGGCTGTCTACGGCACAGATGGATGCCCTGTGTCGGTCGAGAAGATTGTGAA

CATCTTCAATGGGACCAGCTGCCCCAGCCTGGGAGGGAAGCCCAAGCTCTTTTTCATC

CAGGCCTGTGGTGGGGAGCAGAAAGACCATGGGTTTGAGGTGGCCTCCACTTCCCCTG

AAGACGAGTCCCCTGGCAGTAACCCCGAGCCAGATGCCACCCCGTTCCAGGAAGGTTT

GAGGACCTTCGACCAGCTGGACGCCATATCTAGTTTGCCCACACCCAGTGACATCTTTG

TGTCCTACTCTACTTTCCCAGGTTTTGTTTCCTGGAGGGACCCCAAGAGTGGCTCCTGG

TACGTTGAGACCCTGGACGACATCTTTGAGCAGTGGGCTCACTCTGAAGACCTGCAGT

CCCTCCTGCTTAGGGTCGCTAATGCTGTTTCGGTGAAAGGGATTTATAAACAGATGCCT

GGTTGCTTTAATTTCCTCCGGAAAAAACTTTTCTTTAAAACATCAGTCGACTATCCGTA

CGACGTACCAGACTACGCACTCGACTAAGAATTCATCGAGCGGGATCAATTCCGCCCC

CCCCCTAACGTTACTGGCCGAAGCCGCTTGGAATAAGGCCGGTGTGCGTTTGTCTATAT

GTTATTTTCCACCATATTGCCGTCTTTTGGCAATGTGAGGGCCCGGAAACCTGGCCCTG

TCTTCTTGACGAGCATTCCTAGGGGTCTTTCCCCTCTCGCCAAAGGAATGCAAGGTCTG

TTGAATGTCGTGAAGGAAGCAGTTCCTCTGGAAGCTTCTTGAAGACAAACAACGTCTG

TAGCGACCCTTTGCAGGCAGCGGAACCCCCCACCTGGCGACAGGTGCCTCTGCGGCCA

AAAGCCACGTGTATAAGATACACCTGCAAAGGCGGCACAACCCCAGTGCCACGTTGTG
```

-continued

```
AGTTGGATAGTTGTGGAAAGAGTCAAATGGCTCTCCTCAAGCGTATTCAACAAGGGGC
TGAAGGATGCCCAGAAGGTACCCCATTGTATGGGATCTGATCTGGGGCCTCGGTGCAC
ATGCTTTACATGTGTTTAGTCGAGGTTAAAAAACGTCTAGGCCCCCCGAACCACGGGG
ACGTGGTTTTCCTTTGAAAAACACGATAATACCATGGTGAGCAAGGGCGAGGAGCTGT
TCACCGGGGTGGTGCCCATCCTGGTCGAGCTGGACGGCGACGTAAACGGCCACAAGTT
CAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCT
ACGGCGTGCAGTGCTTCAGCCGCTACCCCGACCACATGAAGCAGCACGACTTCTTCAA
GTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAG
TACAACTACAACAGCCACAACGTCTATATCATGGCCGACAAGCAGAAGAACGGCATC
AAGGTGAACTTCAAGATCCGCCACAACATCGAGGACGGCAGCGTGCAGCTCGCCGAC
CACTACCAGCAGAACACCCCCATCGGCGACGGCCCCGTGCTGCTGCCCGACAACCACT
ACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAA
GTAAAGCGGCCGCGACTCTAGAGTCGACCTGCAGGCATGCAAGCTTCAGGTAGCCGGC
TAACGTTAACAACCGGTACCTCTAGAACTATAGCTAGCATGCGCAAATTTAAAGCGCT
GATATCGATAAAATAAAAGATTTTATTTAGTCTCCAGAAAAAGGGGGGAATGAAAGA
CCCCACCTGTAGGTTTGGCAAGCTAGCTTAAGTAACGCCATTTTGCAAGGCATGGAAA
ATACATAACTGAGAATAGAGAAGTTCAGATCAAGGTTAGGAACAGAGAGACAGCAGA
ATATGGGCCAAACAGGATATCTGTGGTAAGCAGTTCCTGCCCCGGCTCAGGGCCAAGA
ACAGATGGTCCCCAGATGCGGTCCCGCCCTCAGCAGTTTCTAGAGAACCATCAGATGT
TTCCAGGGTGCCCCAAGGACCTGAAAATGACCCTGTGCCTTATTTGAACTAACCAATC
AGTTCGCTTCTCGCTTCTGTTCGCGCGCTTCTGCTCCCCGAGCTCAATAAAAGAGCCCA
CAACCCCTCACTCGGCGCGCCAGTCCTCCGATAGACTGCGTCGCCCGGGTACCCGTGT
ATCCAATAAACCCTCTTGCAGTTGCATCCGACTTGTGGTCTCGCTGTTCCTTGGGAGGG
TCTCCTCTGAGTGATTGACTACCCGTCAGCGGGGGTCTTTCATGGGTAACAGTTTCTTG
AAGTTGGAGAACAACATTCTGAGGGTAGGAGTCGAATATTAAGTAATCCTGACTCAAT
TAGCCACTGTTTTGAATCCACATACTCCAATACTCCGTAAATAGTTCATTATGGACAGC
GCAGAAAGAGCTGGGGAGAATTGTGAAATTGTTATCCGCTCACAATTCCACACAACAT
ACGAGCCGGAAGCATAAAGTGTAAAGCCTGGGGTGCCTAATGAGTGAGCTAACTCAC
ATTAATTGCGTTGCGCTCACTGCCCGCTTTCCAGTCGGGAAACCTGTCGTGCCAGCTGC
ATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAACA
TGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGT
```

-continued

```
TCGCTCCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGCAGC

AGCCACTGGTAACAGGATTAGCAGAGCGAGGTATGTAGGCGGTGCTACAGAGTTCTTG

AAGTGGTGGCCTAACTACGGCTACACTAGAAGGACAGTATTTGGTATCTGCGCTCTGC

TGAAGCCAGTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTTTTAA

ATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCA

TAGTTGCCTGACTCCCCGTCGTGTAGATAACTACGATACGGGAGGGCTTACCATCTGG

CCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCT

CCATCCAGTCTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTCGTTTGGTAT

GGCTTCATTCAGCTCCGGTTCCCAACGATCAAGGCGAGTTACATGATCCCCCATGTTGT

GCAAAAAAGCGGTTAGCTCCTTCGGTCCTCCGATCGTTGTCAGAAGTAAGTTGGCCGC

AGTGTTATCACTCATGGTTATGGCAGCACTGCATAATTCTCTTACTGTCATGCCATCCG

TAAGATGCTTTTCTGTGACTGGTGAGTACTCAACCAAGTCATTCTGAGAATAGTGTATG

CGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGAT

CTTACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCGC

AAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTAT

TTAGAAAAATAAACAAATAGGGGTTCCGCGCACATTTCCCCGAAAAGTGCCACCTGAC

GTCTAAGAAACCATTATTATCATGACATTAACCTATAAAAATAGGCGTATCACGAGGC

CCTTTCGTCTCGCGCGTTTCGGTGATGACGGTGAAAACCTCTGACACATGCAGCTCCCG

GAGACGGTCACAGCTTGTCTGTAAGCGGATGCCGGGAGCAGACAAGCCCGTCAGGGC

GCGTCAGCGGGTGTTGGCGGGTGTCGGGGCTGGCTTAACTATGCGGCATCAGAGCAGA

TTGTACTGAGAGTGCACCATATGCGGTGTGAAATACCGCACAGATGCGTAAGGAGAAA

ATACCGCATCAGGCGCCATTCGCCATTCAGGCTGCGCAACTGTTGGGAAGGGCGATCG

GTGCGGGCCTCTTCGCTATTACGCCAGCTGGCGAAAGGGGGATGTGCTGCAAGGCGAT

TAAGTTGGGTAACGCCAGGGTTTTCCCAGTCACGACGTTGTAAAACGACGGCCAGTGC

CANNNNCGCTCTCCCTTATGCGACTCCTGCATTAGGAAGCAGCCCAGTAGTAGGTTGA

GGCCGTTGAGCACCGCCGCCGCAAGGAATGGTGCATGCAAGGAGATGGCGCCCAACA

GTCCCCCGGCCACGGGCCTGCCACCATACCCACGCCGAAACAAGCGCTCATGAGCCC

GAAGTGGCGAGCCCGATCTTCCCCATCGGTGATGTCGGCGATATAGGCGCCAGCAACC
```

-continued

```
GCACCTGTGGCGCCGGTGATGCCGGCCACGATGCGTCCGGCGTAGAGGCGATTAGTCC

AATTTGTTAAAGACAGGATATCAGTGGTCCAGGCTCTAGTTTTGACTCAACAATATCAC

CAGCTGAAGCCTATAGAGTACGAGCCATAGATAAAATAAAAGATTTTATTTAGTCTCC

AGAAAA
```

Engraftment and expansion of human hepatic-specified cells and/or human iHeps and/or human mature iHepatocytes and/or human fetal hepatocytes and/or human adult hepatocytes is surprisingly highly efficient in immunocompromised rats, such as Rag2$^{-/-}$/Il2rg$^{-/-}$ rats including the ALB-iCas9 transgene. For example, a rat can be injected with one to ten million, such as 2, 3, 4, 5, 6, 7, 8 or 9 million human hepatic-specified cells and/or human iHeps and/or human mature iHepatocytes and/or human fetal hepatocytes and/or human adult hepatocytes. Assuming 10% efficiency, 100,000-1'000,000 human hepatic-specified cells and/or human iHeps and/or human mature iHepatocytes and/or human fetal hepatocytes and/or human adult hepatocytes engraft in the recipient rat. An average yield from following expansion is then about 100 million to about 1 billion human hepatic-specified cells and/or human iHeps and/or human mature iHepatocytes and/or human fetal hepatocytes and/or human adult hepatocytes which equates to a 100- to 1000-fold increase in cell number. The disclosed rats can also be used for serial transplantation of human hepatic-specified cells and/or human iHeps and/or human mature iHepatocytes and/or human fetal hepatocytes and/or human adult hepatocytes. Serial transplantation can involve multiple rats and can result in further expansion of human hepatic-specified cells and/or human iHeps and/or human mature iHepatocytes and/or human fetal hepatocytes and/or human adult hepatocytes.

Disclosed herein is a method of expanding human hepatocytes in vivo comprising transplanting isolated human hepatocytes, such as by injection, into an immunocompromised non-human animal, such as (but not limited to) an immunocompromised rat, and allowing the human hepatocytes to expand, and collecting the expanded human hepatocytes from the non-human immunocompromised animal.

Exemplary Uses

Reconstitution of liver tissue in a patient by the introduction of hepatocytes is a potential therapeutic option for patients with acute liver failure, either as a temporary treatment in anticipation of liver transplant or as a definitive treatment for patients with isolated metabolic deficiencies (Bumgardner et al. *Transplantation* 65: 53-61, 1998). Hepatocyte reconstitution may be used, for example, to introduce genetically modified hepatocytes for gene therapy or to replace hepatocytes lost as a result of disease, physical or chemical injury, or malignancy (U.S. Pat. No. 6,995,299). For example, use of transfected hepatocytes in gene therapy of a patient suffering from familial hypercholesterolemia has been reported (Grossman et al. *Nat. Genet.* 6: 335, 1994). In addition, expanded human hepatocytes can be used to populate artificial liver assist devices (see U.S. Pat. No. 9,485,971, incorporated herein by reference). Exemplary uses for cells produced by the disclosed methods are provided, for example, in U.S. Pat. No. 9,090,878. Some exemplary uses are listed below.

The disclosed methods can be produce hepatocytes to reconstitute the liver of a subject. Reconstitution of liver tissue in a patient by the introduction of hepatocytes (also referred to as "hepatocyte transplantation") is a potential therapeutic option for patients with acute liver failure, either as a temporary treatment in anticipation of liver transplant or as a definitive treatment for patients with isolated metabolic deficiencies (Bumgardner et al., *Transplantation* 65: 53-61, 1998) or cirrhosis. The liver failure can also be caused by an infection, such as hepatitis.

A major obstacle to achieving therapeutic liver reconstitution is immune rejection of transplanted hepatocytes by the host, a phenomenon referred to (where the host and donor cells are genetically and phenotypically different) as "allograft rejection." Immunosuppressive agents have been only partially successful in preventing allograft rejection (Javregui et al., *Cell Transplantation* 5: 353-367, 1996; Makowka et al., *Transplantation* 42: 537-541, 1986)

Human hepatocytes produced herein can be matched to the MHC of the subject, and/or can be produced from the subject's own cells, so they are autologous. In some embodiments, the hepatocytes include an exogenous gene. In other embodiments, the hepatocytes are transplanted into a human host to correct a genetic defect. Exemplary uses are disclosed below.

(1) Therapy of Liver Dysfunction and/or Failure:

Disclosed are methods of treating liver deficiencies by administering cells produced by the methods disclosed herein. These cells can be administered to any subject with the liver deficiency, such as, but not limited to, toxic liver disease, metabolic liver disease, acute liver necrosis, effects of acetaninophen, hemochromatosis, Wilson's Disease, Crigler Najar, hereditary tyrosinemia, familial intrahepatic cholestatis type 3, ornithine transcarbarylase (OTC) deficiency, and urea cycle disorder. Cells produced by the disclosed methods can also be used to treat hepatitis, such as chronic viral hepatitis A, B, C, and acute hepatitis A, B, C, D, E, or infections with cytomegalovirus and herpes simplex virus. Cells produced by the disclosed methods can also be used to treat liver dysfunction caused by toxoplasmosis, hepatosplenic schistosomiasis, liver dysfunction associated with syphilis, leptospirosis and amoebiasis. Cells produced by the disclosed methods can also be used to treat a metabolic disease such as, but not limited to, haemochromatosis, Gilbert's syndrome, Dubin-Johnson syndrome and Rotor's syndrome. Cells produced by the disclosed methods can also be used to treat alcoholic liver disease such as, but not limited to, conditions such as fatty liver, fibrosis, sclerosis, cirrhosis, and toxic liver disease.

(2) Bioartificial Liver (BAL) Devices

In patients with terminal liver failure, the use of a BAL device can bridge the time to liver transplantation. A BAL device is designed to support the detoxification functions performed by the liver, hence decreasing the risk and severity of CNS complications associated with acute liver failure. BAL devices could benefit three groups of patients; those with fulminant hepatic failure, those waiting for an imminent transplant, and those with early failure of a liver transplant. Although some positive results have been seen in patients with liver failure, further exploration of the usefulness of BAL devices has been hampered by lack of suitable cells. Currently, tumor-derived cell lines or animal cells, which might be associated with possible tumor cell seeding, immune responses, and xeno-zoonoses, are used. The availability of large quanitites of human hepatocytes, would enables the production of optimized BAL devices to bridge patients till the liver spontaneously regenerates or a donor-liver is available.

(3) Pharmaceutical Testing

Drug discovery involves screening one or more compounds for the ability to modulate the function or phenotype of the hepatocytes. Accordingly, cells produced by the disclosed methods can utilized in assays to determine the effect of pharmacologic agents. These assay can conducted in vitro, on cells produced by the disclosed methods or in vivo, in animals transplanted with hepatocytes produced by the disclosed methods.

In these assays, protein or RNA can be evaluated. This can be done through any of the well-known techniques available in the art, such as by FACS and other antibody-based detection methods and PCR and other hybridization-based detection methods. One could also perform biological assays for one or more biological effects of the agent to be tested. Assays for expression/secretion include, but are not limited to, ELISA, qRT-PCR, Western blots, Northern blots, dot blots, and immunohistochemistry.

Agents can be identified through screening the cells with large combinatorial libraries. These compound libraries may be libraries of agents that include, but are not limited to, small organic molecules, antisense nucleic acids, siRNA DNA aptamers, peptides, antibodies, non-antibody proteins, cytokines, chemokines, and chemo-attractants.

In some embodiments, transgenic animals, such as rats, transplanted with human hepatocytes (or human hepatocytes expanded in and collected from these animals) are used to evaluate any one of a number of parameters of drug metabolism and pharmacokinetics. For example, studies can be carried out to evaluate drug metabolism, drug/drug interactions in vivo, drug half-life, routes of excretion/elimination, metabolites in the urine, feces, bile, blood or other bodily fluid, cytochrome p450 induction, enterohepatic recirculation, and enzyme/transporter induction.

In some embodiments, transgenic animals, such as transgenic rats, transplanted with human hepatocytes (or human hepatocytes expanded in and collected from these animals) are used to evaluate toxicology and safety of a compound, including therapeutic agents or candidate agents (such as small molecules or biologicals), environmental or biological toxins, or gene delivery systems. For example, cell cycle proliferation in human hepatocytes can be evaluated, such as to determine the risk of cancer following exposure to the compound. Toxicity to hepatocytes can also be assessed, such as by histology, apoptosis index, liver function tests and the like. Analysis of hepatocyte metabolism can also be performed, such as analysis of metabolites after infection of stable isotope precursors.

The efficacy of particular drugs can also be evaluated in transgenic animals, such as rats, transplanted with human hepatocytes. Such drugs include, for example, drugs to treat hyperlipidemia/atherosclerosis, hepatitis and malaria.

In some embodiments, the disclosed transgenic rats including the human hepatocytes (or human hepatocytes expanded in and collected from these rats) are used to study gene therapy protocols and vectors. For example, the following parameters can be evaluated: transduction efficiency of gene delivery vehicles including viral and non-viral vectors; integration frequency and location of genetic payloads (integration site analysis); functionality of genetic payloads (gene expression levels, gene knockdown efficiency); and side effects of genetic payloads (analysis of gene expression or proteomics in human hepatocytes in vivo).

The sorted fresh human hepatocytes can be used for clinical autologous-cell transplantation. If patient-derived iPS cells have a single mutation that cause a metabolic genetic liver disease (e.g. but not limited to urea cycle disorders, branched-chain amino acids disorders, crigler-najjar syndrome, primary hyperoxaluria, familial hypercholesterolemia, niemann-pick type c, cholesteryl ester storage disease, Wilson disease, neonatal hemochromatosis, tyrosinemia, glycogen storage disease, alpha-1-antitrypsin deficiency, mitochondria defects, Phenylketonuria), these patient-derived iPS-hepatocytes can be gene edited and transplanted back into the patient by cell infusion directly into the patients liver using the portal vein route. These patient-derived iPS-hepatocytes also can be used for bioengineering liver grafts for autologous-transplantation. For example, Patent METHOD OF PREPARING ARTIFICIAL ORGANS, AND RELATED COMPOSITIONS. Publication number: WO2015168254, incorporated herein by reference.

The disclosure is illustrated by the following non-limiting Examples.

EXAMPLES

Example 1

Exemplary Methods

A schematic diagram of a method for generating human iPSC is shown in FIG. 2.

A—Initiation of Differentiation Through Single Cell Passage
  Prior to starting differentiation, differentiating hiPS colonies are marked and aspirated
  When hiPS colonies reach 60% confluence, they are carefully washed with PBS and detached in single cells by Accutase treatment
  hiPS cells are centrifuged at 300 G and resuspended in mTeSR
  Between 0.5 to 2 million hiPS cells are plated in GFR coated 6-well plate and kept in a low oxygen incubator overnight.

Figure 4B:
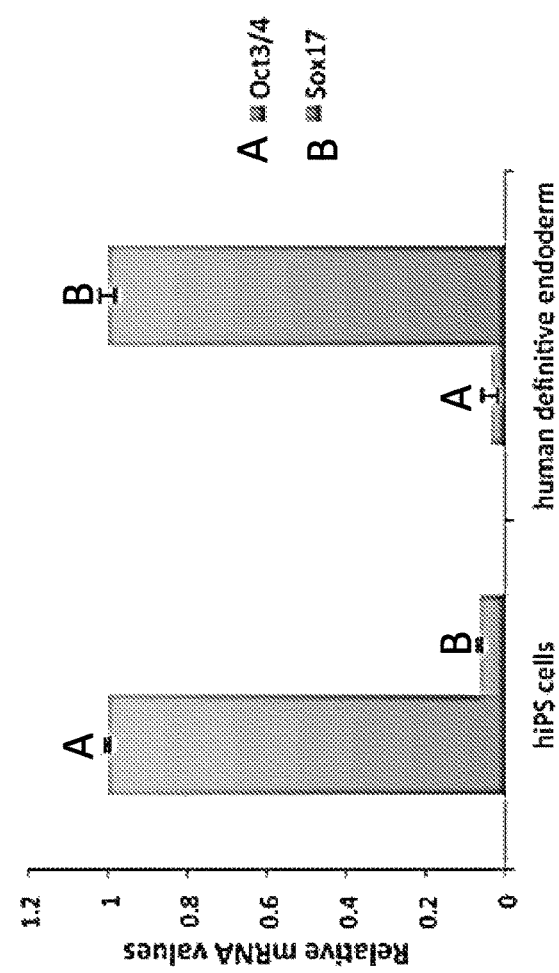
FIGS. 4A-4B Definitive endoderm characterization of hIPSC after Stage 2 (see FIG. 2). A) Immunofluorescence of SOX17 on cells after definitive endoderm induction. Nuclei were counterstained with DAPI. B) Oct3/4 and SOX17 expression in pluripotent and definitive endoderm cells assessed by means of RTqPCR.
Figure 4A:
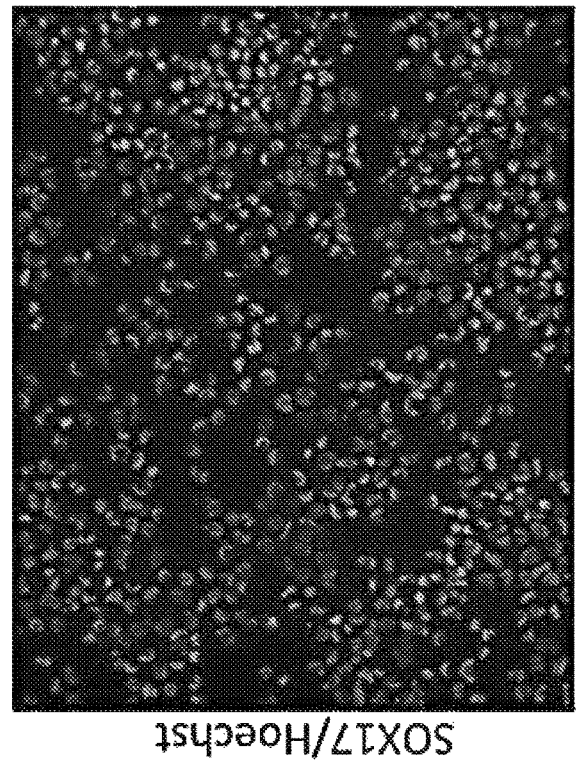

B—Differentiation of Definitive Endoderm (Stage 1 and 2)
  When cells reach 20-30% of confluence (FIG. 3), a defined medium containing RPMI, B27 minus insulin supplements, 1% of Non-Essential Amino Acids, 100 ng/ml Activin A, 20 ng/ml BMP4 and 10 ng/ml FGF2 is added to the cells every day for two days and cells are placed in a normal $O_2$ incubator (Stage 1).
  A defined medium containing RPMI, B27 minus insulin supplements, 1% of Non-Essential Amino Acids, 100 ng/ml Activin A is added to the cells every day for two days and cells are placed in a normal $O_2$ incubator.
  After 4 days of differentiation, a subset of cells is tested definitive endoderm differentiation (Stage 2).
  Endodermic cells are tested for SOX17 expression using immunofluorescence (red). All nuclei are counterstained with DAPI (blue) (FIG. 4A). More than 80% of cells should express SOX17 to proceed with hepatic specification (Stage 3).
  Other endodermic cells are subsequently verified through RNA analysis. Total RNA is isolated from one well. 1

μg is reverse transcribed using a mixture of Random Hexamer and Oligo-dT primer. A qRT-PCR for SOX17, Oct3/4 is performed (FIG. 4B).

C—Hepatic Specification and Maturation Formula Methods

Figure 5:
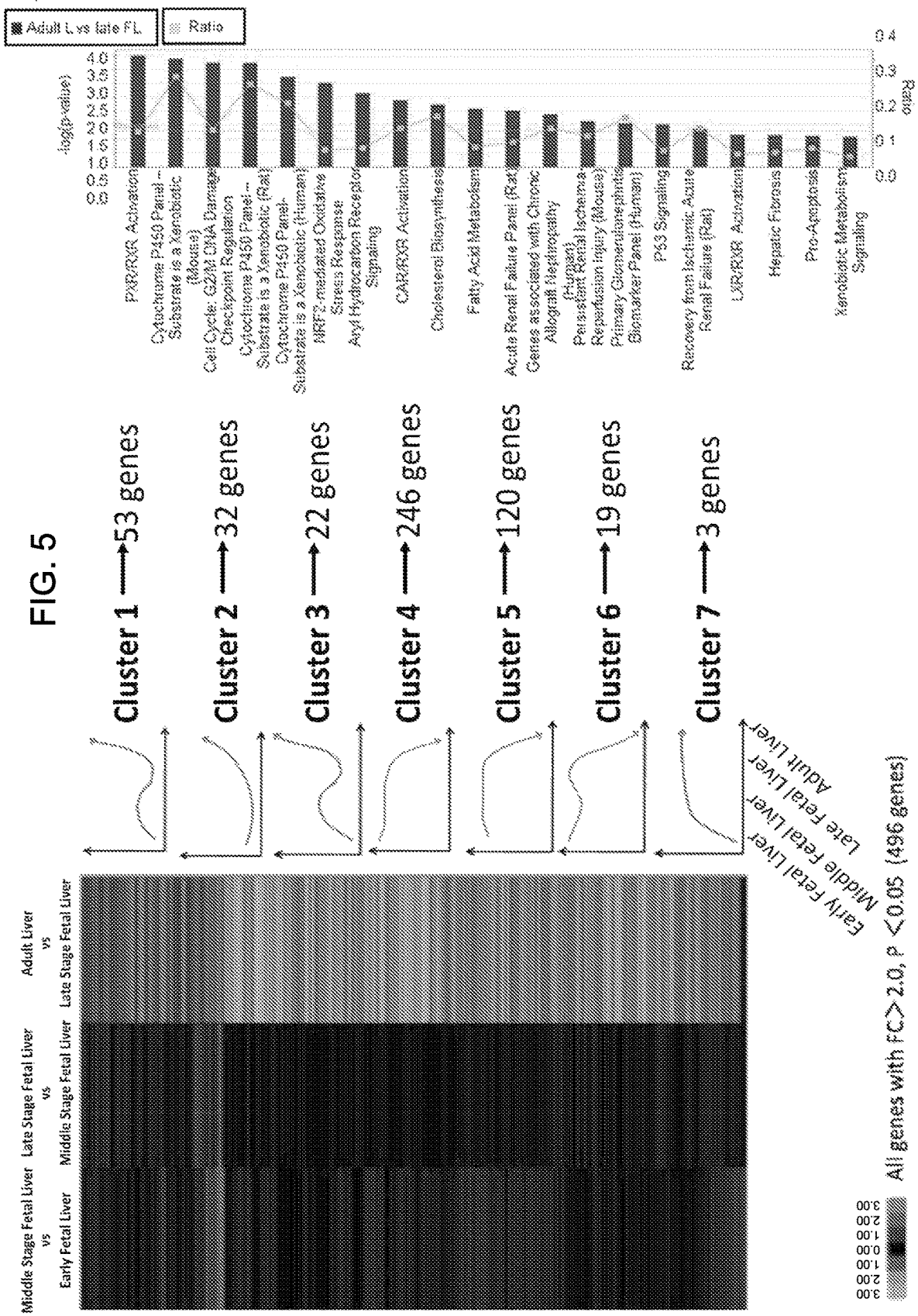
FIG. 5 Gene array of human hepatic genes. Hepatic genes were clustered according to their expression during development and associated with relative pathway expression. Pathways expressed during later stage of development were identified and classified according to their expression.

Early, Middle, Late stage fetal liver and Adult liver were hierarchically Clustered to determine differentially expressed genes from human livers during development (FIG. 5).

This analysis identified key developmental pathways linked to nutrition and metabolism during liver development. Glycolytic metabolism and bile acid production pathways were determined to be essential for hepatic development. As such, we developed our stage 3 formula (hepatic specification) with a low glucose medium and stage 4 formula (hepatic maturation) with bile acids and cholesterol agents.

D—Hepatic Specification (Stage 3)

A defined medium containing 45% DMEM low glucose 1 g/l, 45% F-12, 10% Knock-Out Serum, 1% Non-Essential Amino Acids, 0.5% L-glutamine, 1% 20 ug/ml HGF and 1% DMSO is added to the cells every other day for 10 days.

A subset of cells if tested for hepatic specification before proceeding to hepatic maturation (Stage 4).

Figure 6:
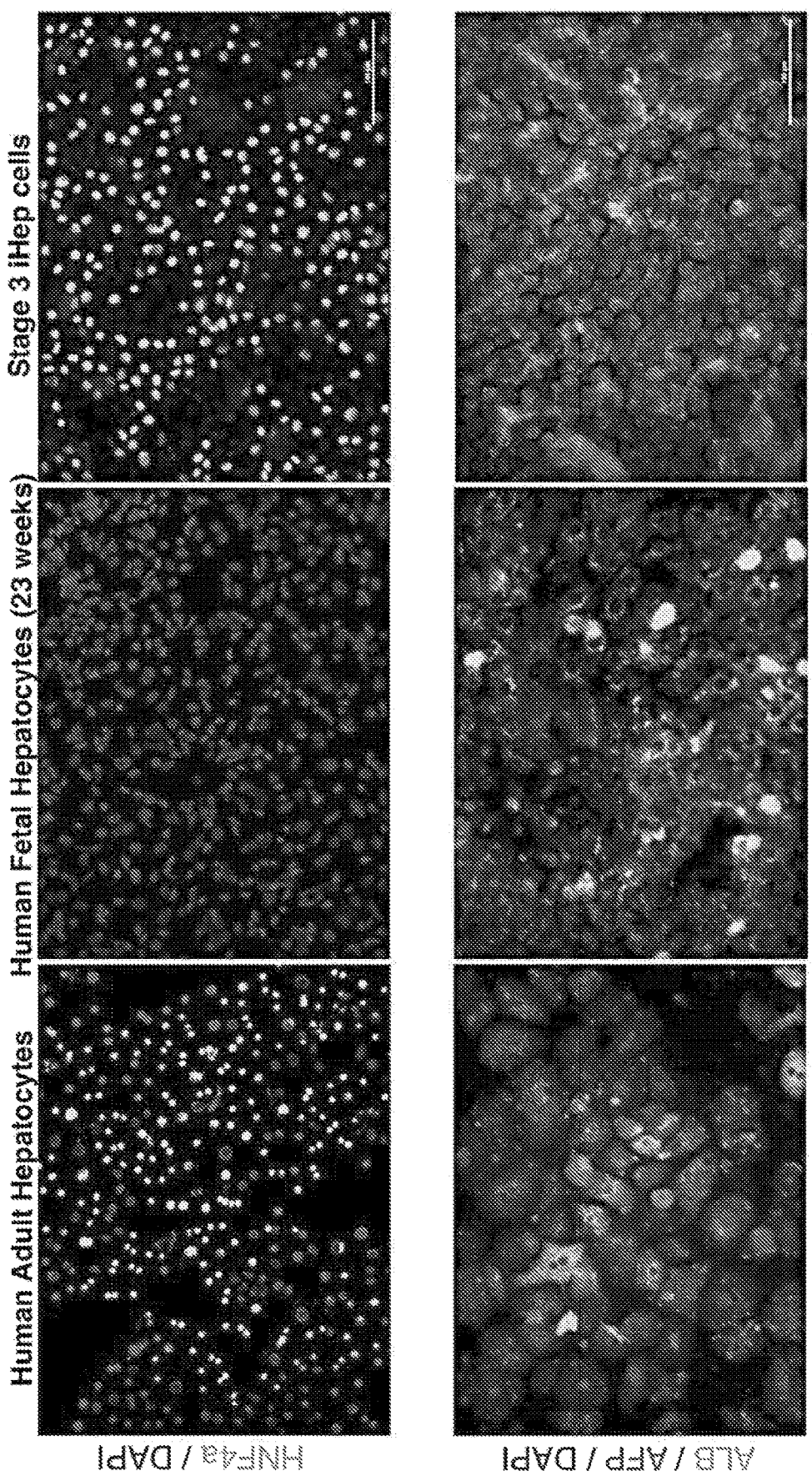
FIG. 6 Characterization of human iPS cells during hepatic specification (Stage 3) defined as hepatic-specified cells. Immunofluorescence of HNF4 (green), Albumin (green) and afetoprotein (red) on human adult hepatocytes, human fetal hepatocytes and Stage 3 iPSC derived hepatocyte (iHeps) cells. Nuclei were counterstained with DAPI.

Hepatic cells are tested for HNF4 (green), Albumin (green) and α-fetoprotein through immunofluorescence. All nuclei are counterstained with DAPI (blue). More than 80% of cells express HNF4 and Albumin and less than 10% of cells express α-fetoprotein (FIG. 6).

Figure 7:
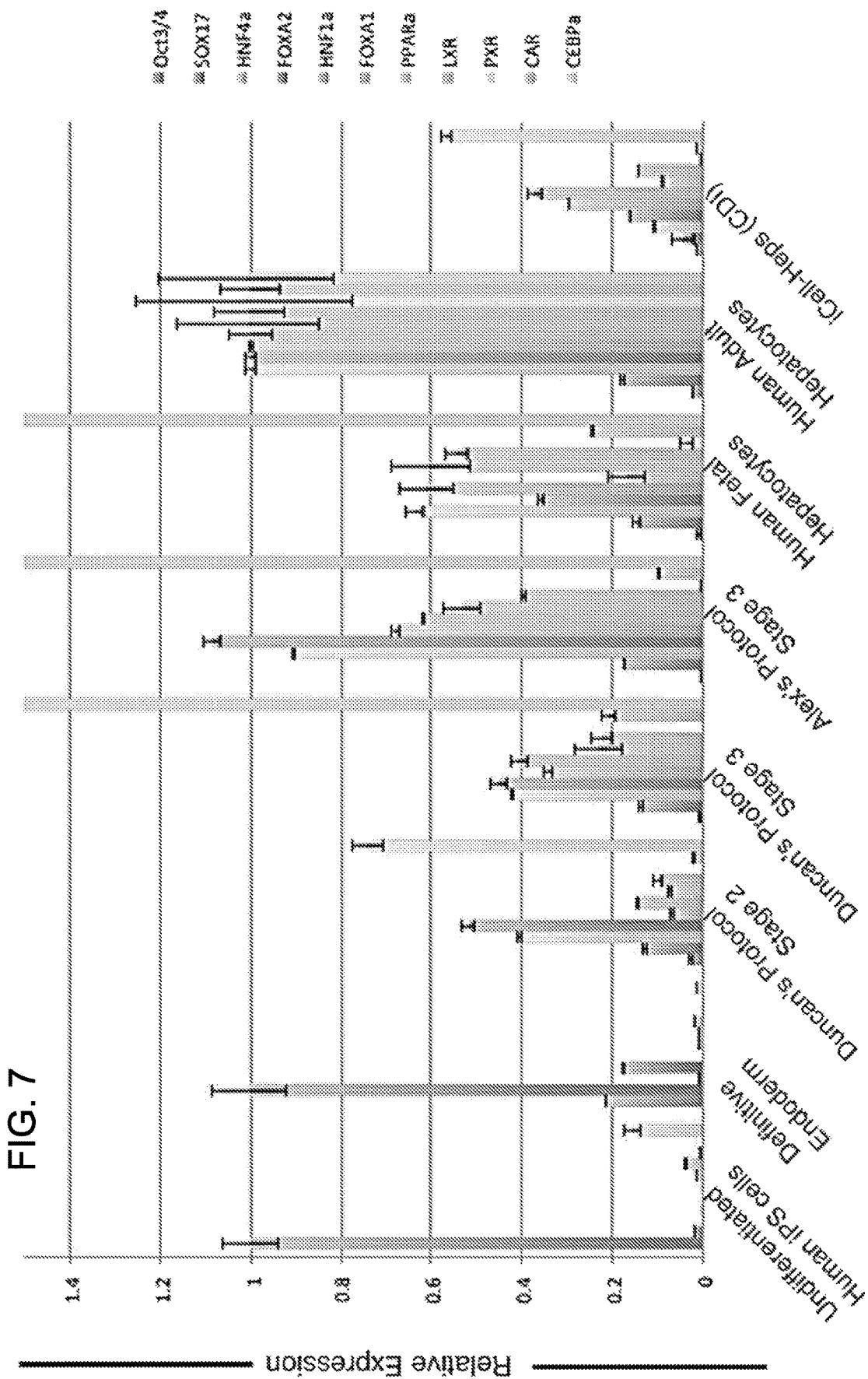
FIG. 7 Gene expression characterization of human iPS cells after hepatic specification (stage 3) defined as hepatic-specified cells. Developmental factors (Oct3.4, SOX17), Hepatic nuclear factors (HNF4, FOXA2, HNF1a, FOXA1) and liver-specific metabolic factors (PPARa, LXR, CAR, Cebpa) expression in undifferentiated human iPS cells, definitive endodermal cells and human iPS cells differentiated into hepatic cells using a known published protocol (at two different stages; 2 and 3), known as Duncan protocol (See Si-Tayeb et al., Hepatology 51(1):297-305, 2010), the presently disclosed protocol (stage 3), iCell-hep (CDI), human fetal hepatocytes and human adult hepatocytes assessed by means of RTqPCR.

Cells are subsequently verified through RNA analysis. Total RNA is isolated from one well. 1 μg is reverse transcribed using a mixture of Random Hexamer and Oligo-dT primer. A qRT-PCR for hepatic transcription factors and hepatic metabolic factors in comparison to hiPS, definitive endoderm, Duncan's protocol iCell-Heps (CDI), Fetal and Adult hepatocytes is performed (FIG. 7).

ES cells were previously used to produce hepatocytes (see Soto-Gutiérrez A, et al Reversal of mouse hepatic failure using an implanted liver-assist device containing ES cell-derived hepatocytes. Nat Biotechnol. 2006 November; 24(11):1412-9 and Soto-Gutiérrez A, et al. Differentiation of mouse embryonic stem cells to hepatocyte-like cells by co-culture with human liver nonparenchymal cell lines. Nat Protoc. 2007; 2(2):347-56, both incorporated herein by reference). It was determined that, using the disclosed protocols, there was high expression of several hepatocyte nuclear factors in the resulting hepatocyte-like-cells. This protocol involves two stages of definitive endoderm induction that produces 80-90% of cells expressing SOX17 (definitive endoderm marker), one stage of hepatic specification that produces 90% of cells expressing adult form of human HNF4α (the most important nuclear factor in hepatocytes). Additionally, transcription factors related to liver regeneration were expressed in the resulting cells (FOXA2, HNF1α, FOXA1, PPARα, LXR, PXR and CAR and CEBPa) at the levels between human adult and fetal hepatocytes.

Other human iPS-derived hepatocytes, such as those using the Duncan Protocol (Si-Tayeb K, and Duncan S A. Highly efficient generation of human hepatocyte-like cells from induced pluripotent stem cells. Hepatology. 2010 January; 51(1):297-305) or commercially available human iPS-derived hepatocytes (Cellular Dynamics International, CDI, a Fujifilm company) show significantly lower levels of these liver-specific transcription factors. Thus, a superior effect was documented of using the disclosed protocols.

E—Hepatic Cells Detachment

Cells are washed with PBS and detached either with Trypsin, Tryple or Accutase treatment.

Cells are centrifuged at 50 G for 2 min.

Pelleted cells (big population) and cells contained in the supernatant (small population) are replated separately at 1 million of cells per well. After Hepatic Specification (Stage 3) of human iPS cells, the resulting cells are harvested and separated by centrifugation based on their weight into big population (cell pellet) and small population (cells in the supernatant). Then both populations are subjected to Hepatic Maturation (Stage 4).

Cells are placed in a normal incubator overnight

F—Hepatic Maturation (Stage 4)

When cells reach 30-40% confluence, a defined medium containing 45% DMEM low glucose 1 g/l, 45% F-12, 10% Knock-Out Serum, 1% Non-Essential Amino Acids, 0.5% L-glutamine, 0.1% of Gentamicin/Amphotericin-B, 1% of Pennicillin/Streptomycin, 1% 50 ug/ml HGF, 1% DMSO, 0.5 uM Dexamethasone, 0.1% of Ascorbic Acid, 0.1% of Bovine Serum Albumin Free of Fatty Acids, 0.1% of Hydrocortisone, 0.1% of Transferrin, 0.1% of Insulin, 100 uM of Urso deoxycholic acid, 1× of Cholesterol, 20 uM of Palmitic Acid, 30 uM of Oleic Acid, 20 uM of Rifampicin is added to the cells every other day for 4 days.

Mature hepatic cells are tested for HNF4 (green), Albumin (green) and α-fetoprotein through immunofluorescence. All nuclei are counterstained with DAPI (blue). More than 90% of cells express HNF4 and Albumin and less than 5% of cells express α-fetoprotein (FIG. 8).

Figure 8:
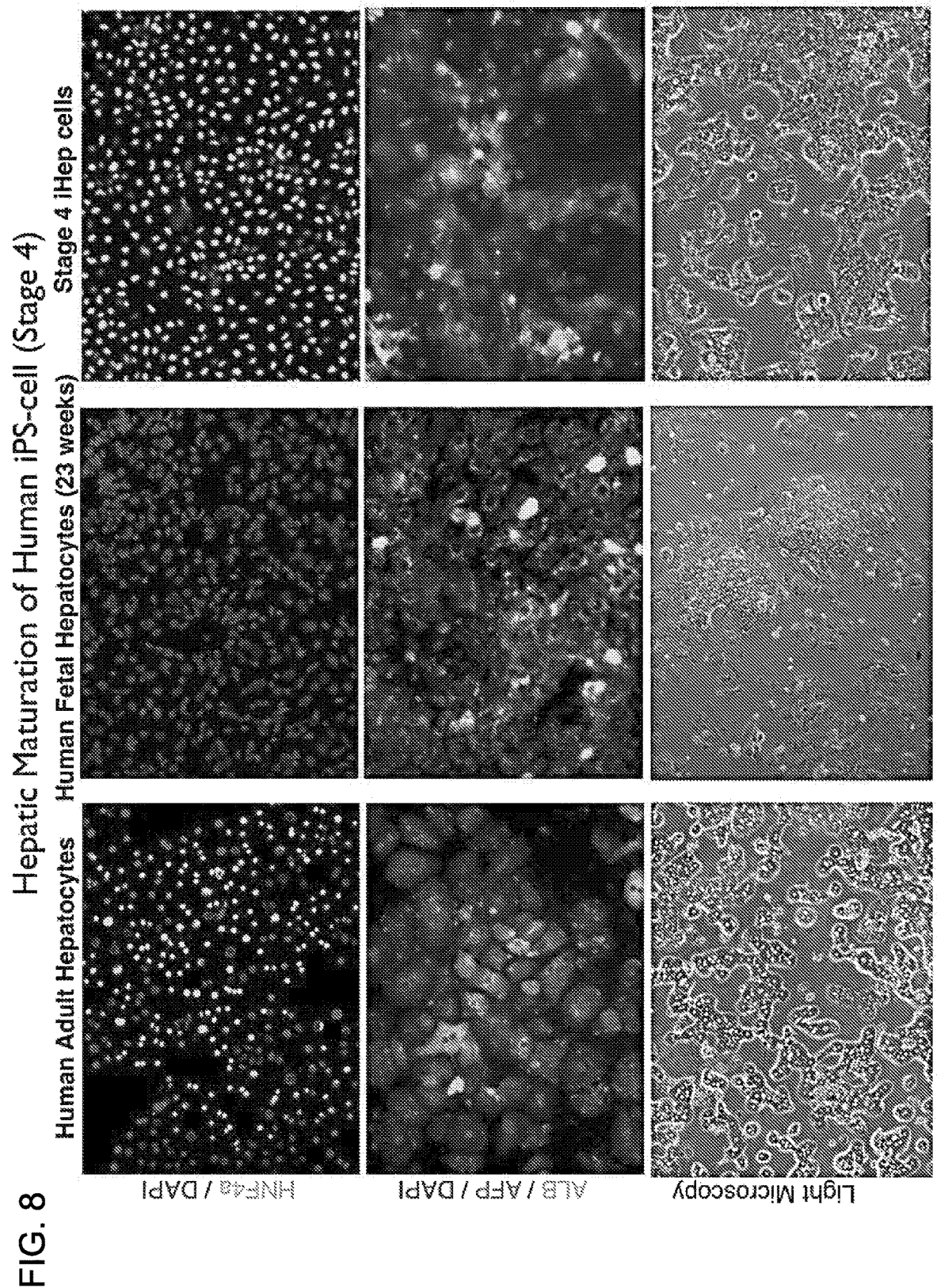
FIG. 8 Gene expression of human iPS cells after hepatic maturation (stage 4) defined as iHeps. Immunofluorescence of HNF4 (green), Albumin (green) and afetoprotein (red) on human adult hepatocytes, human fetal hepatocytes and Stage 4 iHeps cells. Nuclei were counterstained with DAPI.

A maturation step was incorporated, where the resulting liver cells are exposed to a combination of fatty and bile acids, xenobiotics and growth factors, producing a phenotype with nearly 100% of the cells express and secrete albumin with no detectable expression of Alpha Feto-Protein (an immature hepatic marker) (FIG. 8).

Figure 9:
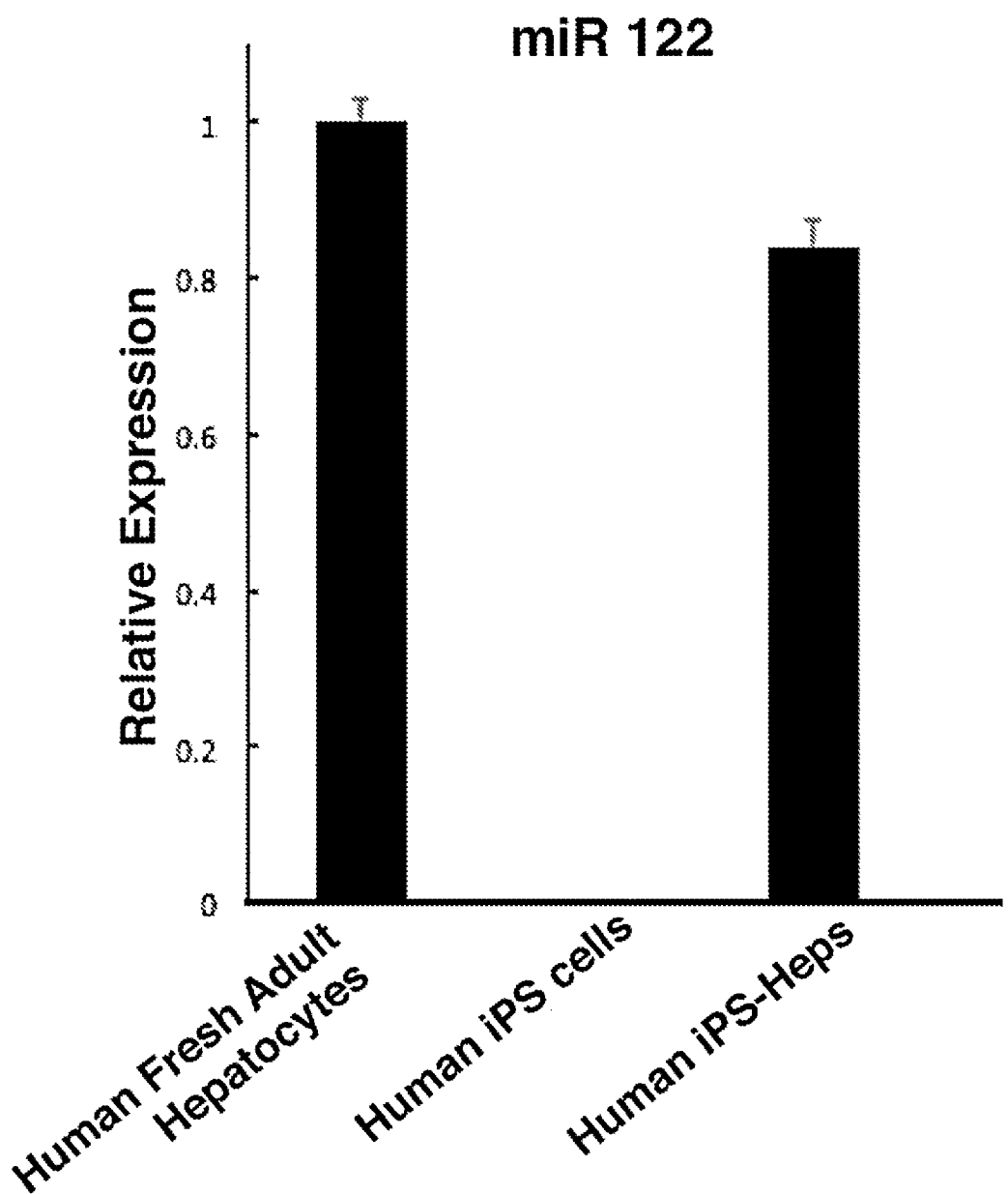
FIG. 9 mir-122 relative expression on human fresh Adult hepatocytes, human IPSC and human iHeps (Stage 4, presently disclosed methods) cells.

Mir-122 level, the most frequent miRNA in the adult liver and a key factor for liver homeostasis, is confirmed through micro RNA qPCR. Total micro RNA is isolated from one well. 1 μg is reverse transcribed using a mixture of Random Hexamer. A qRT-PCR for mir-122 is performed (FIG. 9).

G—Small Versus Big Population Characterization

At the end of differentiation (stage 4), both small and big populations of cells are characterized.

Cells are size sorted using FACS analysis. Big populations of cells determined to be more granular than small population of cells.

Figure 10:
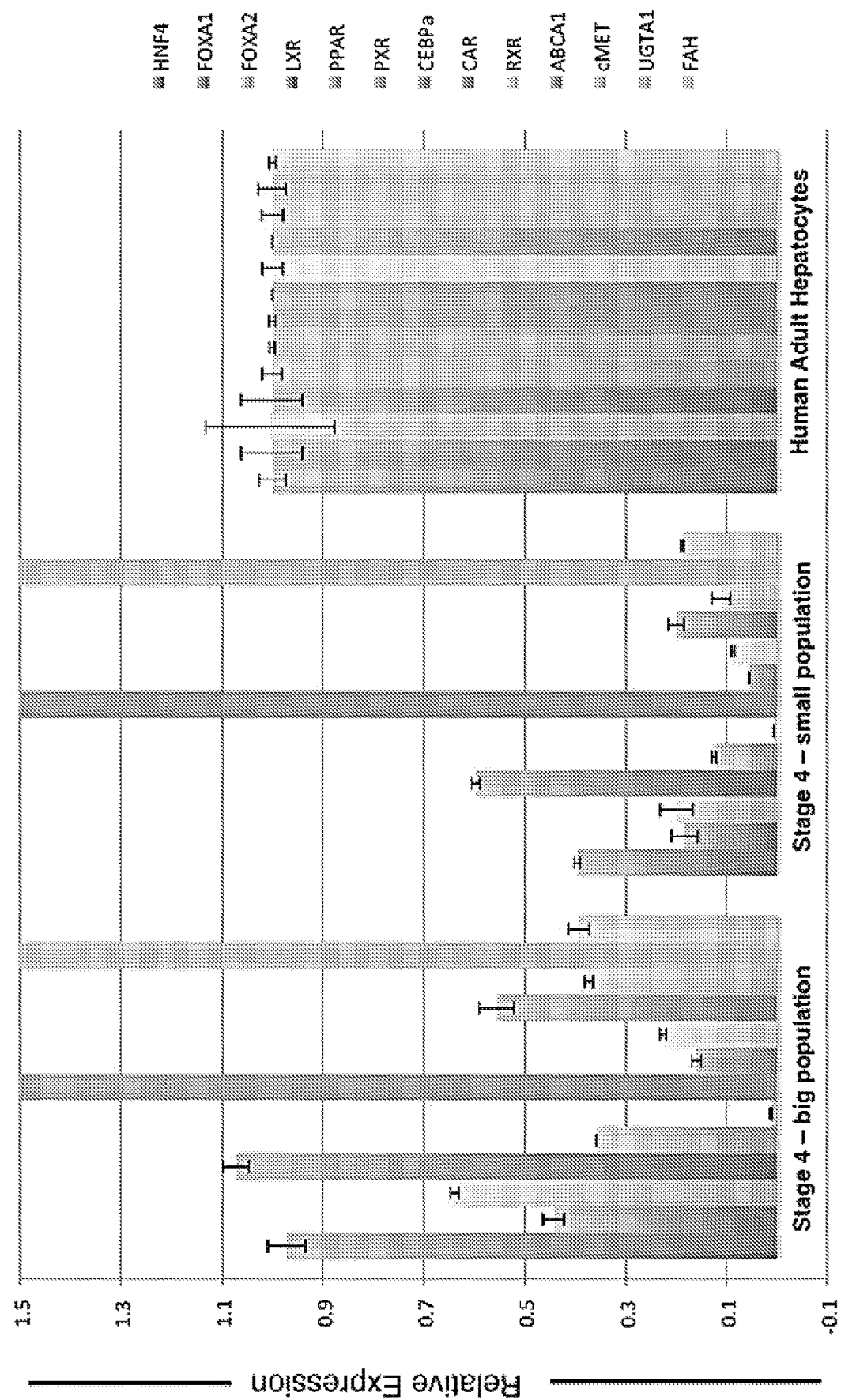
FIG. 10 Gene expression of iHeps (Stage 4) big and small populations after hepatic maturation. After Hepatic Specification (Stage 3) of human iPS cells, the resulting cells are harvested and separated by centrifugation based on their weight into big population (cell pellet) and small population (cells in the supernatant). Then both populations are subjected to Hepatic Maturation (Stage 4). Then, hepatic nuclear factors (HNF4, FOXA2, FOXA1) and metabolic factors (PPARa, PXR, LXR, CAR, RXR, ABCA1, cMET, UGTA1, FAH, Cebpa) expression in small population and big population of stage 4 cells compared to human adult hepatocytes were assessed by means of RTqPCR. The big and small populations are determined based on gene expression and the amount of mitochondria.

Cells are analyzed through RNA analysis. Total RNA of both populations is isolated from one well. 1 μg is reverse transcribed using a mixture of Random Hexamer and Oligo-dT primer. A qRT-PCR for hepatic transcription factors and hepatic metabolic factors in big and small population in comparison to Adult hepatocytes is performed. Big populations of cells have a closer profile to adult hepatocytes (FIG. 10).

Gene expression analysis of iHeps at Stage 4 from big and small populations after hepatic maturation show that big population of iHeps express higher levels of liver-specific nuclear factors (FOXA2, HNF1u, FOXA1, PPARα, LXR, PXR and CAR and CEBPa) and clinically relevant hepatic enzymes and membrane receptors (ABCA1, cMET, UGTA1, FAH).

Figure 11A:
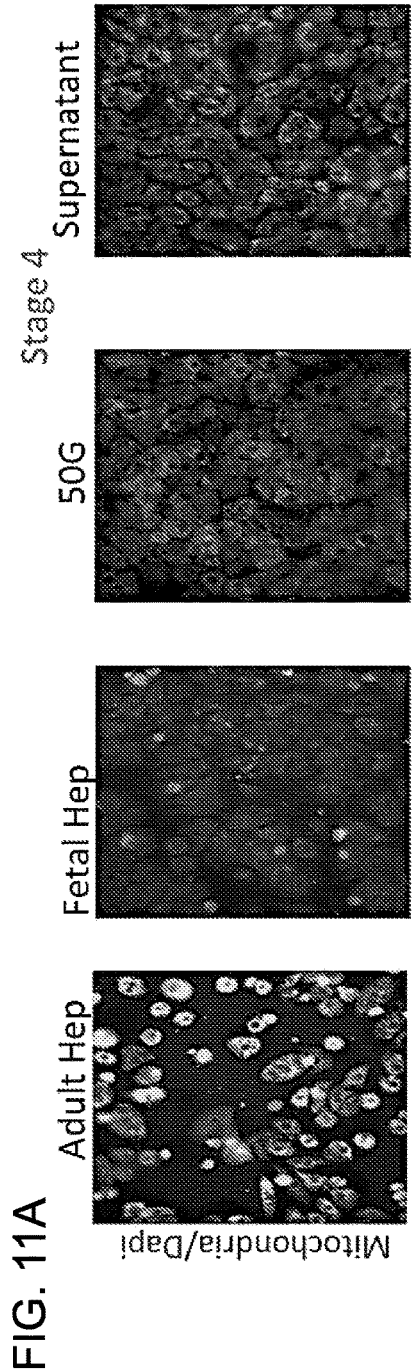
FIGS. 11A-11B Characterization of mitochondrial profile in small and big iHep populations (Stage 4). A) Fluorescence of mitochondria through MitoTracker Green FM dye. Nuclei were counterstained with DAPI. B) DNA mitochondrial relative expression assessed by means of qPCR.
Figure 11B:
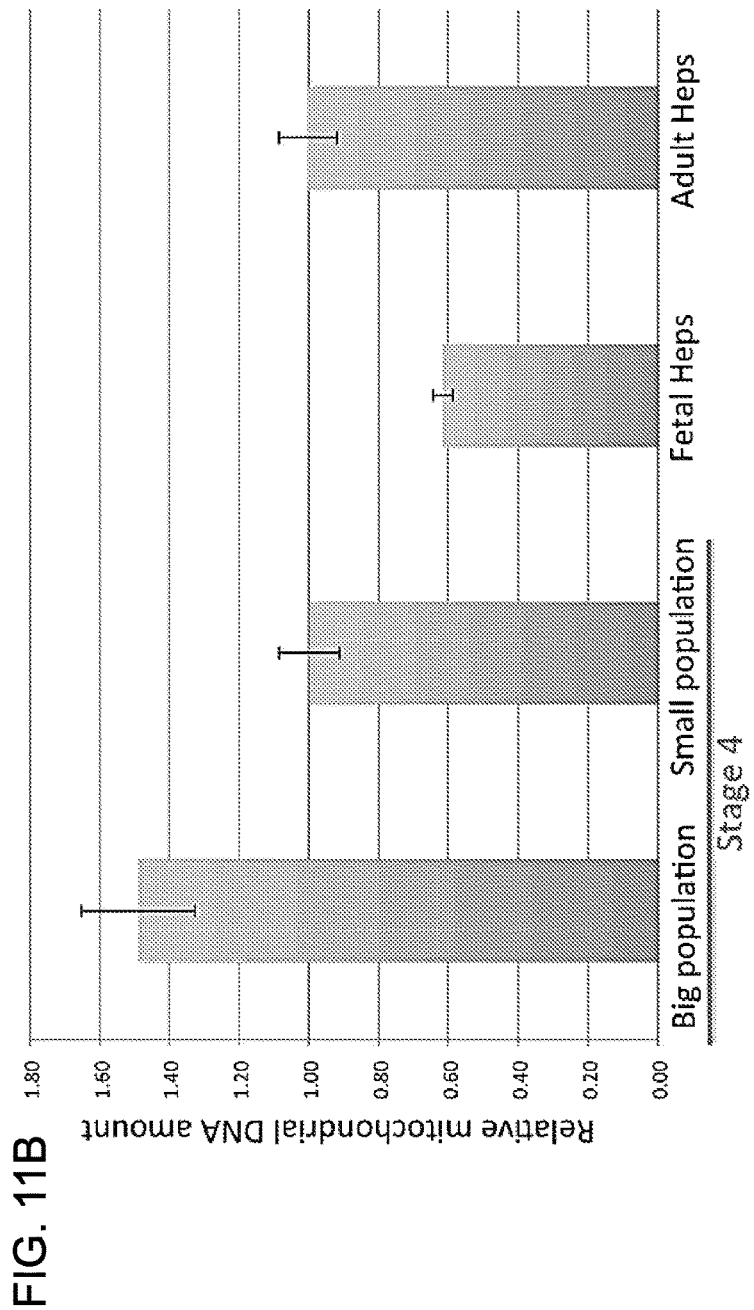

To assess their metabolic activity, small and big cell populations are tested for mitochondrial content through MitoTracker Green FM kit and by measuring mtDNA content. Big populations of cells have higher mtDNA content, similar to adult hepatocytes (FIGS. 11A and 11B).

Figure 12:
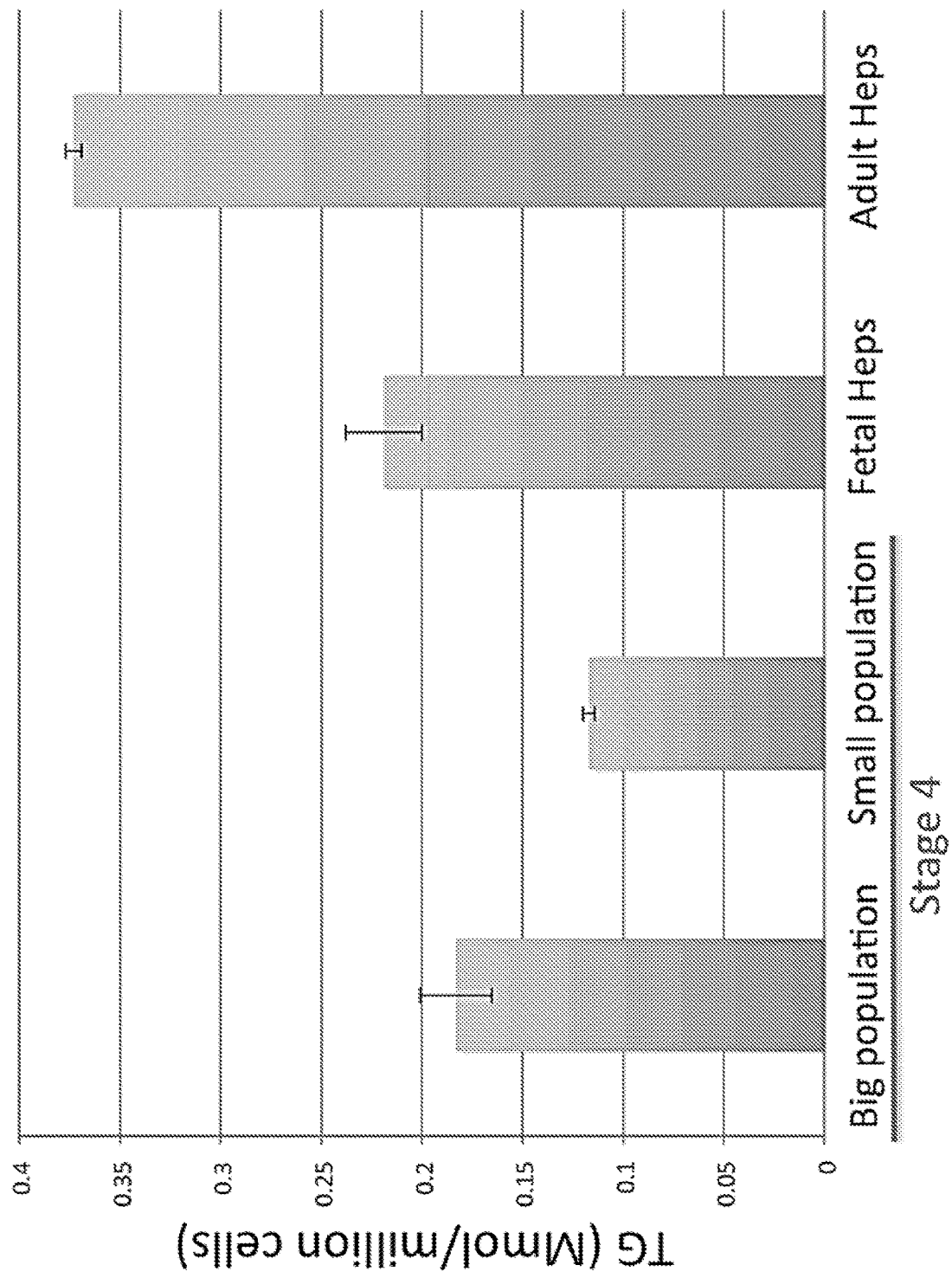
FIG. 12 Lipid profile characterization of small and big population of iHep (Stage 4). Intracellular lipid content by mmol/million cells.

Small and big cell populations are quantified for lipid content through Enzychrom™ Triglyceride Assay Kit. Big populations of cells have more intracellular triglycerides, a key feature of hepatocytes. (FIG. 12).

Big populations of cells at stage 4 are mature and defined iHeps used for repopulation studies.

Example 2

Engineering of Rag2$^{-/-}$ Il2rg$^{-/-}$ ALB-iCasp9 Rats

A—Functional Testing of iCasp9 Suicide Plasmid and Cloning of iCasp9 Plasmid for Liver Specific Expression.

Because repopulated rat livers with human iPS-Heps can be reconstituted with both rodent cells and human cells, systems to maximize the human component to 100% of the livers and to purify human cells after perfusion/isolation of livers are beneficial. Suicide systems can be designed to potentiate these processes by efficiently inducing apoptosis in transduce cells. An inducible caspase-9 (iCasp9), encoded by a suicide gene engineered from human caspase-9, was incorporated. This system is not immunogenic and can kill transduce cells in a cell-cycle-independent manner. iCasp9 is a fusion protein engineered by replacing the caspase recruitment domain with a mutated FK506-binding protein to allow conditional dimerization. Thus in the presence of a chemical inducer of dimerization (AP1903), dimerized iCasp9 directly activates intracytoplasmic caspase-3, directly triggering apoptosis in transduced cells. Thus, we decided to generate an iCasp9 suicide system that can be expressed specifically in liver cells by encoding the rat albumin promoter (see FIG. 13).

HEK293 cells are transfected with pMSCV-F-del-Casp9_IRES-GFP (Addgene).

To assess transfection efficiency, cells are co-transfected with a TagRFP control plasmid (1/10 of total amount of DNA).

On day 3 transfected cells and negative control are monitored, counted and seeded (1E04 cells/96-well) for Caspase 3/7 Assay (Promega; G8091) Per Transfection/Negative Control cells were seeded as follows:

Per concentration small molecule (chemical inducer of dimerization) AP1903 (ApexBio) two wells, the same amount for negative control. For shuttle control, also wells per concentration are seeded.

On day 4, stimulation with AP1903 starts (0; 0,1; 1; 10 nmol/1). Shuttle control includes cells treated with ethanol only. T=0 h was measured immediately and T=24 h is measured as end point. (FIG. 13)

iCasp9-IRES-GFP construct is cloned with the rat albumin promoter pEAlb123.

iCasp9 expression (mRNA) is quantified in H4-II-E-C3 by qRT-PCR. Cells are transfected with plasmids pEAlb123-iCasp9-IRES-GFP and pcDNA3-CMV-eGFP (positive control).

Cells are harvested and RNA is isolated. iCASP9 and eGFP-specific PCR primers are used to measure expression (FIG. 14).

Example 3

Engineering of Rag2$^{-/-}$ Il2$^{-/-}$ (FRG) Rat

SCID mice are widely used in biomedical research as hosts for allogeneic and xenogeneic tissue grafts. However, the laboratory rat is an ideal model for physiological, pharmacological, toxicological, and transplantation studies, and recently, the CRISPR/Cas9 system has been proven to be an efficient genome engineering tool in rats. We therefore use this technologies to generate double-knockout Rag2 and Il2rg (F344-Rag2$^{-/-}$ Il2rg$^{-/-}$ [FRG]) rats (see FIGS. 15A and 15B).

The design of gRNAs targeting on the exon 2 of Il2rg gene and on the exon 3 of Rag2 gene are gRNA-Il2rg, CCTATAGTGCATAGTGAGGT and gRNA-Rag2, TAGCTGGGTAACGAAGAGGT.

The designed gRNA and Cas9 mRNA are microinjected into fertilized F344 oocytes using micromanipulator (Narishige, Tokyo Japan).

The two-cell embryos cultured overnight are transferred into the oviducts of pseudopregnant Wistar female rats.

Genotyping of 8 newborn animals revealed that all of them carried mutations, comprising deletions from 4 bp to 27 bp and a 1-bp insertion at the targeted sequences of Il2rg gene.

Genotyping of 25 newborn animals revealed that two of them carried mutations, comprising a 18 bp-deletion and a 2-bp insertion at the targeted sequences of Rag2 gene.

Example 4

Incorporation of the Suicide System ALB-iCasp9 into the Rag2$^{-/-}$ Il2rg$^{-/-}$ Rat To replace recipient rat liver to donor human iPS-derived hepatocytes, the iCasp9 suicide system is incorporated into the SCID (Rag2$^{-/-}$ Il2rg$^{-/-}$) rat by CRISPR-mediated knock-in methods.

The 'safe harbor' integration site of rat Rosa26 locus is targeted with ALB-iCasp9 plasmids by CRISPR/Cas9 system.

Two gRNAs are constructed: one targeting the rat Rosa26 locus to cleave genomic DNA and the other targeting 5' of the ALB promoter sequence for concurrent cleavage of the plasmid DNA. Two 80-bp single-stranded oligodeoxynucleotides (ssODNs) are designed to ligate the two cut ends.

A mix of 100 ng μl$^{-1}$ of the Cas9 mRNA, 50 ng μl$^{-1}$ of each of the two gRNAs, 50 ng μl$^{-1}$ of each of the two ssODNs and 5 ng μl$^{-1}$ of the ALB-iCasp9 plasmid will be microinjected into F344 rat embryos.

The two-cell embryos will be transferred into pseudopregnant Wistar rats to obtain ALB-iCasp9 knock-in (KI) rats.

Crossing the ALB-iCasp9 KI rat with the FRG (Rag2$^{-/-}$ Il2rg$^{-/-}$) rat will provide the incorporation of the suicide system ALB-iCasp9 into the liver of the recipient FRG rat.

Treatment of the chemical inducer of dimerization (AP1903) activates intracytoplasmic caspase-3, directly triggering apoptosis in the recipient FRG rat hepatocytes.

The chemical inducer of dimerization (AP1903) can be given by several routes (intraperitoneal, intravenous, intramuscular, subcutaneous and orally) at different doses (0.01-10 mg/kg).

Example 5

Liver Repopulation of XSCID (Il2rg$^{-/-}$) Rats Using Human iPS-Derived Hepatocytes A—Liver Preconditioning for Hepatocyte Transplantation The injury caused by severe cases of acute liver failure and certain inherited metabolic liver diseases (e.g., Type 1 Tyrosinemia, alpha-1 antitrypsin deficiency) could result in complete arrest of regeneration capacity of the native liver creating a growth advantage for transplanted normal hepatocytes or auxiliary liver grafts. Based on this knowledge, animal models of liver repopulation using hepatocyte transplantation have been created. Similarly, a model of liver repopulation after hepatocyte transplantation was developed whereby selective growth of donor-derived cells is achieved in the liver of animals previously treated with pyrrolizidine alkaloids (retrorsine). Retrorsine causes mitosis-inhibition of resident hepatocytes and senescence, resulting in the selective proliferation of the donor-derived cells transplanted after exposure to the alkaloid. In this model, near-complete replacement of the recipient liver is observed within 2 to 3 months post-transplantation when isolated hepatocytes are delivered in conjunction with ⅔ partial hepatectomy. Therefore, this regeneration-preconditioning regimen is employed.

- Rats weighing 100 to 140 g are given two injections of retrorsine (Sigma) (30 mg/kg) each, intraperitoneally, 2 weeks apart.
- Dilute retrorsine for stock solution (10 mg/mL) in 100% Ethanol. Before injections, the stock solution is diluted in sterile saline solution to adjust the correct dose per animal (30 mg/kg). Normally, final ethanol concentration should be 10% or less. Retrorsine can be given using different routes (intraperitoneal, intravenous, subcutaneous and intramuscular).
- For intraperitoneal injections, the point of entry for the needle is located.
- An imaginary line is drawn across the abdomen just above the knees. The needle is inserted along this line on the animal's right side and close to the midline.
- Rats usually are used for experiments four weeks after the last injection of retrorsine.
- The liver preconditioning effect of retrorsine administration also is substituted by hepatic irradiation. Administration of 50 Gy selectively to the liver using small animal radiation research platforms. Cell transplantation are performed twenty-four hours after preconditioning irradiation.

B—Protocol for Transplantation of Human iPS-Derived Hepatocytes

- Place the rat in a chamber for induction of anesthesia with a mix of 2% isoflurane and oxygen (1-2 liters/min).
- After induction of anesthesia, shave the abdominal wall with electronic hair clipper. Place the animal on the surgical table made of a Styrofoam pad and fix all four limbs to the table using rubber bands and pushpins with its face in the anesthesia system's nozzle on the far side.
- Start isoflurane inhalation with oxygen flow at 3-4% for the induction of anesthesia during laparotomy.
- Disinfect the abdominal wall with disinfectants (betadine followed by 70% ethanol). Wipe excess disinfectant with sterile gauze to avoid exposing internal organs to these disinfectants.
- Make a long midline abdominal skin and muscle incision from the xiphoid process down to the pubis. Expose the abdominal cavity by retracting the lower abdominal walls bilaterally using forceps. Use pushpins or 18 G needles to fix forceps in appropriate places on the table to achieve sufficient exposure and to provide good visualization.
- After making the abdominal incision, lower the isoflurane flow to 1-2% for the maintenance of anesthesia.
- After laparotomy, place sterile gauze moistened with saline solution under small intestine. Use moisten cotton swab to gently align small intestine on the sterile gauze without any twist. Wrap small intestine with moisten gauze and position small intestine on the left side of the abdominal cavity to expose the abdominal aorta.
- For ⅔ hepatectomy, a 2-0 silk suture is placed on the base of the left lateral lobe (close to the liver hilum) using the forceps. With a cotton tip, rotate the left lateral lobe to its original position, while holding the right end of the suture with the forceps, to make the suture go around the lobe. Then, tie the two ends of the suture over the top of the left lateral lobe, placing the knot as close to the base of the lobe as possible. Cut the tied lobe just above the suture.
- The median lobe is identified and suture is placed between the stump and the median lobe. Pull the median lobe down over the suture. Tie the two ends of the suture following the knot line. Cut the tied median lobe above the suture, leaving an ischemic base above the knot and a small part of still perfused median lobe below.
- After ⅔ hepatectomy, 5 million cells suspended in 300-500 microliters of DMEM culture medium are injected intrasplinecally.
- Then, Irrigate the abdomen with warm saline, and close the muscle and skin in two layers with 4-0 Vicryl. Additional saline can be administered to compensate for blood loss. All procedures are performed with sterility and inside a sterile laboratory hood.

C—Characterization of Liver Repopulation Over Time Using Human iPS-Derived Hepatocytes.

The ability to functionally repopulate immune-deficient mice has become the benchmark for having generated a true hepatocyte vs a hepatocyte-like facsimile, incapable of liver repopulation. Interestingly, only limited engraftment of stem cell-derived human hepatocyte-like cells has been reported using other protocols. Ultimately, clinical transplantation of autologous liver cells requires the generation of great numbers of liver cells. Thus, in order to establish an animal model for liver repopulation to be used for liver repopulation and generate sufficient number of highly functional iPSC-Heps, five million iPSC-Heps or human fetal isolated hepatocytes (Fetal-Heps) were transplanted into the spleen of XSCID rats. Prior to transplantation, the recipient animals were pretreated with retrorsine (a drug that inhibits the cell cycle of specifically hepatocytes) and underwent a 70% partial hepatectomy at the time of transplantation, to create an environment where there was a selective growth advantage to the transplanted cells as indicated below in the section for liver preconditioning.

- As control group, human fetal hepatocytes were used for transplantation.

Human fetal hepatocytes were isolated from fetal livers obtained after the termination of pregnancy performed at 20-23 weeks of gestation.

Primary human fetal hepatocytes were isolated by digesting the tissue in EMEM (Lonza, Walkersville, Md.), which contains 0.5 mg/ml of collagenase (Type XI, Sigma-Aldrich, Saint-Louis Mo., Cat. #C7657), on a lab shaker for 40 minutes.

Viability was assessed by trypan blue exclusion test and was routinely >85%.

Fetal hepatocytes were prepared after isolation procedure for transplantation as indicated below.

Human iPS-hepatocytes (prepared using the methods disclosed herein) are differentiated as disclosed herein.

Human iPS-hepatocytes (Duncan Protocol) are differentiated as indicated in the following publication. (Si-Tayeb K, Noto F K, Nagaoka M, Li J, Battle M A, Duris C, North P E, Dalton S, Duncan S A. Highly efficient generation of human hepatocyte-like cells from induced pluripotent stem cells. Hepatology. 2010 January; 51(1):297-305, incorporated herein by reference)

Human CDI (Fujifilm) iPS-Hepatocytes were purchased from CDI (https://cellulardynamics.com).

Figure 16:
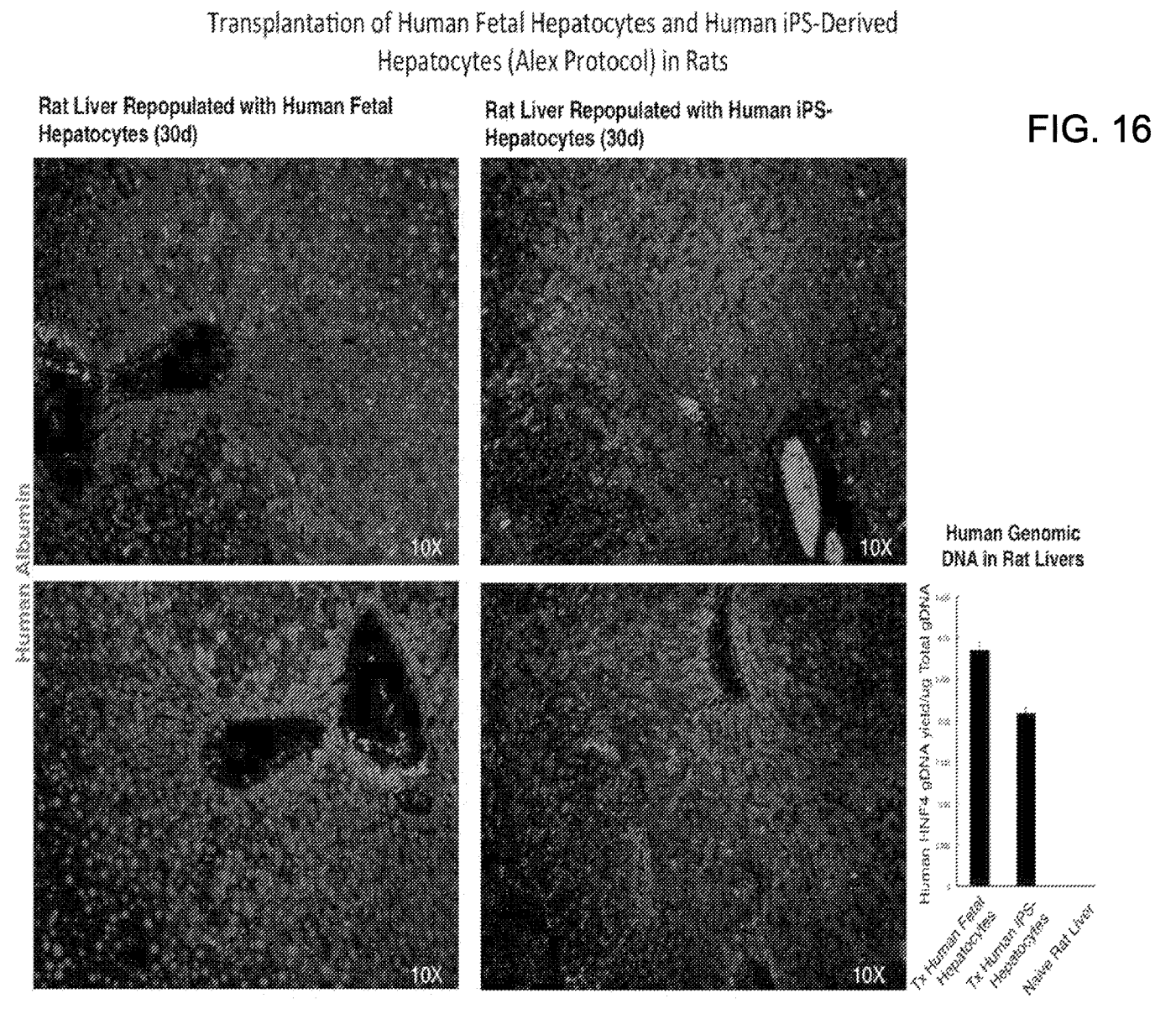

The livers from transplanted XSCID rats from all experimental groups were harvest at 30 d and 60 d after hepatocyte transplantation. The liver tissue is fixed in 4% PFA and embedded in Paraffin. Histological sections from each lobe of the liver were subjected to immune-histochemistry for human specific-albumin (Bethyl) at 30 d (FIG. 16) and for human specific-mitochondria (millipore) and for CYP3A4 (Abcam) (FIG. 16).

Figure 17:
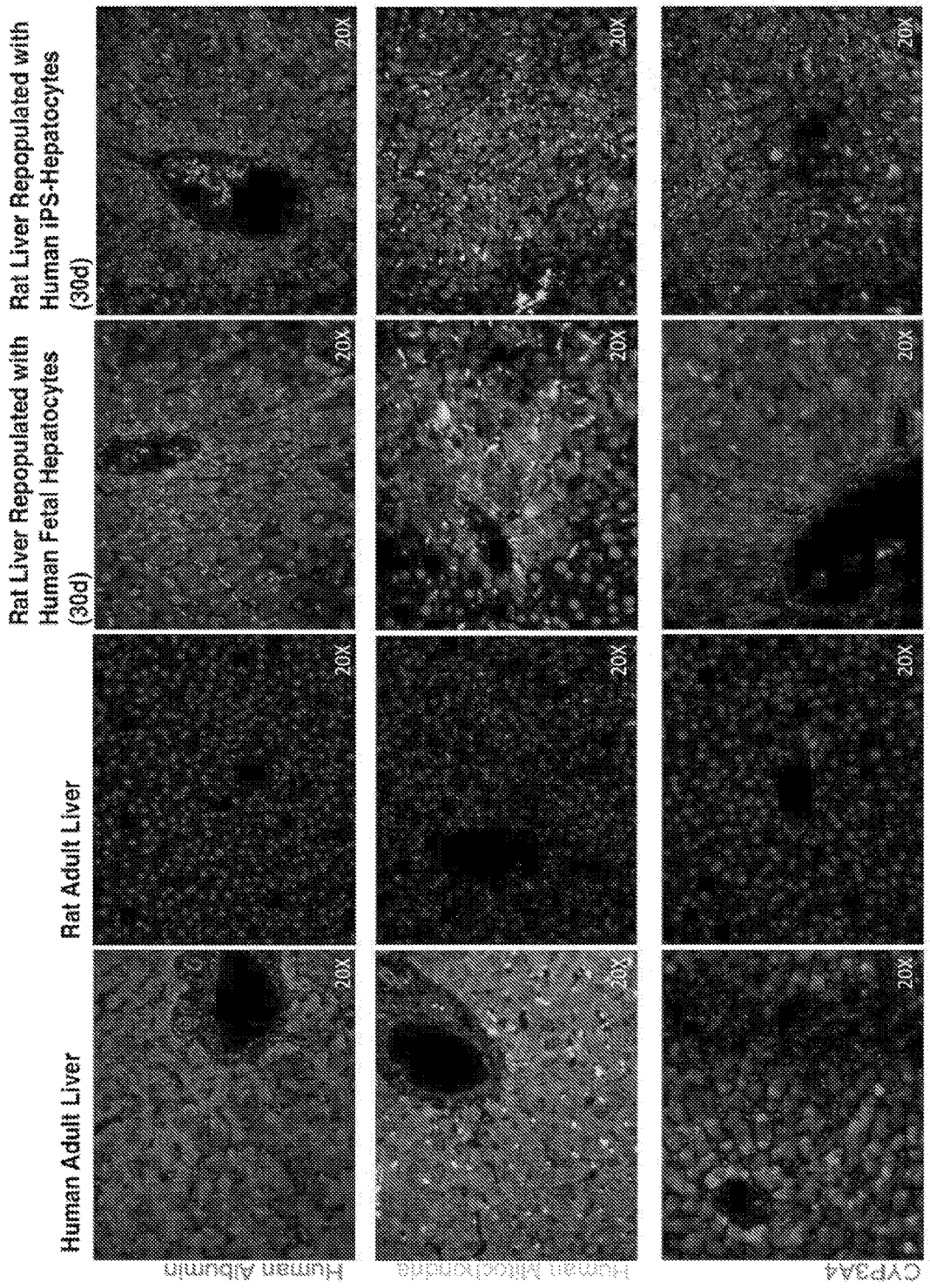
FIG. 17 In order to corroborate the presence of human specific markers in the livers of XSCID transplanted rats, human specific-mitochondria and the specific human cytochrome CYP3A4 are also used. The expression of three human specific markers follow similar pattern of repopulation colonies.

Additionally, to determine the presence of human cells, homogenates of the rat livers were prepared at 30 d and genomic DNA was extracted. The human HNF4 gene was quantified by DNA PCR using taqman primers (Thermo Fisher, RPLP0_CCKAK1K, Cat #4400294 and Hs07218401_cn HNF4 copy Cat #4400291 for detection of both species). (FIG. 17).

In order to compare the repopulation ability of other human iPS-hepatocytes and other standard protocols; commercially available human iPS-hepatocytes (Cellular Dynamics International, CDI, a Fujifilm company) were transplanted in XSCID rats retrorsine-treated and hepatectomized. Also, iPS-hepatocytes were differentiated using Duncan Protocol previously reported in literature (Si-Tayeb K, Noto F K, Nagaoka M, Li J, Battle M A, Duris C, North P E, Dalton S, Duncan S A. Highly efficient generation of human hepatocyte-like cells from induced pluripotent stem cells. Hepatology. 2010 January; 51(1):297-305, incorporated herein by reference).

Sixty days after transplantation, treated livers were harvested and analyzed for the presence of human hepatocytes within the rat liver. Commercially available human iPS-hepatocytes (Cellular Dynamics International, CDI, a Fujifilm company) and human iPS-hepatocytes produced using the Duncan protocol show only engraftment of the cells around the portal vein with no evidence of repopulation. In contrast, human iPS-hepatocytes produced by the disclosed methods (also called an "Alex protocol") show the presence of large colonies of human hepatocytes repopulating the rat liver (FIG. 18).

The table below lists the components that were tested.

| Stage | Conditions | Reagents | Dose range | Time range |
|---|---|---|---|---|
| 1 | O2 21%, 37 C. Everyday medium change | Activin A<br>FGF2<br>BMP4 | 50-200 ng/mL<br>10-50 ng/mL<br>20-100 ng/mL | 2-3 days |
| 2 | O2 21%, 37 C. Everyday medium change | Activin A | 50-200 ng/mL | 2-3 days |
| 3 | O2 21%, 37 C. Every-other-day medium change | L-Glu<br>DMSO<br>HGF<br>Low Glucose culture medium | 0.5-2%<br>1-3%<br>20-150 ug/mL<br>0.2-2 g/L | 8 to 14 days |
| 4 | O2 21%, 37 C. Every-other-day medium change | L-Glu<br>DMSO<br>HGF<br>Dexamethasone<br>Urso deoxycolic acid<br>Cholesterol<br>Palmitic Acid<br>Oleic Acid<br>Rifampicin<br>Low Glucose culture medium | 0.5-2%<br>1-3%<br>20-150 ug/mL<br>0.5-2 mM<br>50-150 mM<br>0.5-1x<br>10-50 uM<br>10-50 uM<br>10-50 uM<br>0.2-2 g/L | 4-6 days |
| 5 | Sterile conditions | Transplantation time | N/A | Human iPS-Derived Heps can be transplanted at the end of stage 3 and/or at the end of Stage 4 |
|  |  | Repopulation time | N/A | 3 days to 24 months |
|  |  | trasplanted cell number | 0.5-10 × 10$^6$ | 4 weeks after last Retrorsine pre-treatment |
|  |  | Retrorsine pretreatment | 5-50 mg/kg | 2-6 week |
|  |  | hepatectomy percentage | 0-90% |  |
|  |  | Small molecule (AP1903) | 0.01-10 mg/kg | Every week for 3 to 12 months |

Example 6

Generation of Human Livers in the Rat for Functional Genome Editing and Screening with hiPS-Tet-On-Cas9 with CRISPR/Cas9 Technology A—Generation of Human iPS-Tet-On-Cas9
- hiPS-Tet-On-Cas9 were engineered using methods disclosed in U.S. Provisional Application No. 62/369,698, incorporated herein by reference.
- To test for Cas9 efficiency, doxycycline was added to a final concentration of 0.5 µg/ml and cells were cultivated for 48 h.
- The presence of GFP reporter proteins was monitored by fluorescence microscopy (FIG. 19A).
- Total RNA was isolated from each well and 1 µg was reverse transcribed using a mixture of Random Hexamer and Oligo-dT primer. The expression of each Cas9/GFP system was determined by quantification of the target cDNA expression levels relative non-induced cells and a reference gene (FIG. 19B).

B—In Vivo Assay of hiPS-Tet-On-Cas9 Genome Edition and Screening

Viral Production of sgRNA
- Pooled plasmid library of single sgRNA (Addgene) was transfected into HEK-293T cells with lentiviral packaging plasmids (Addgene).
- After transfection, the culture medium was harvested and the vector stock concentrated.

hiHeps-Tet-On-Cas9 Transduction with Single or Polled sgRNA
- hiPS-Tet-On-Cas9 cells were differentiated into iHeps using methods developed in "1-Differentiation of hiPS cells into hepatocytes".
- Two days before transduction, doxycycline was added to the medium of hiHeps-Tet-On-Cas9 cells.
- hiHeps-Tet-On-Cas9 cells were then transduced with sgRNA lentivirus. The day after, positively transduced cells are selected by adding an antibiotic selection.

In Vivo Screening
- Positively transduced hiHeps-Tet-On-Cas9 cells can repopulate immunodeficient rat livers (Il2rg$^{-/-}$ or Rag2/−, Il2rg$^{-/-}$, ALB-iCasp9 models) using the disclosed methods, see "Generation of patient-specific iPS-derived hepatocytes for cell therapy".
- The functional assay evaluation depends on the screening test characteristic (ex: proliferation; tumor formation; cell response to hibernation etc.).
- In vivo screening will include dissection by laser capture and further analysis through next generation sequencing.

C—Generation of Human Livers in the Rat for Gene Function with hiPS-Tet-On-shRNA Technology.

Figure 20A:
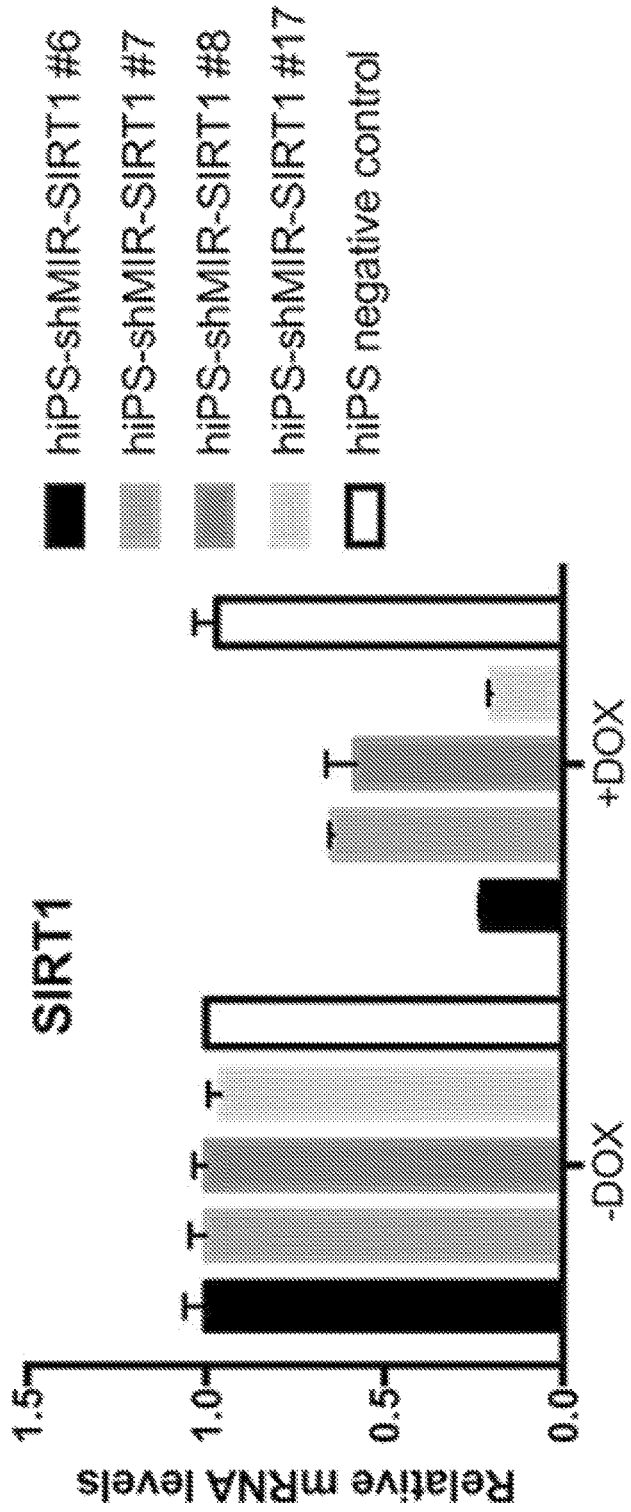
FIGS. 20A-20B SIRT1 knockdown characterization in hiPS-shMIR-SIRT1 cells. A) SIRT1 expression on hiPS-shMIR-SIRT1 clones with and without doxycycline assessed by means of RTqPCR. B) Western blot analysis of SIRT1 expression on hFF-shMIR-SIRT1, hiPS-shMIR-SIRT1 and hiPS-TagRFP with and without doxycycline. GADPH was used as a loading control.
Figure 20B:
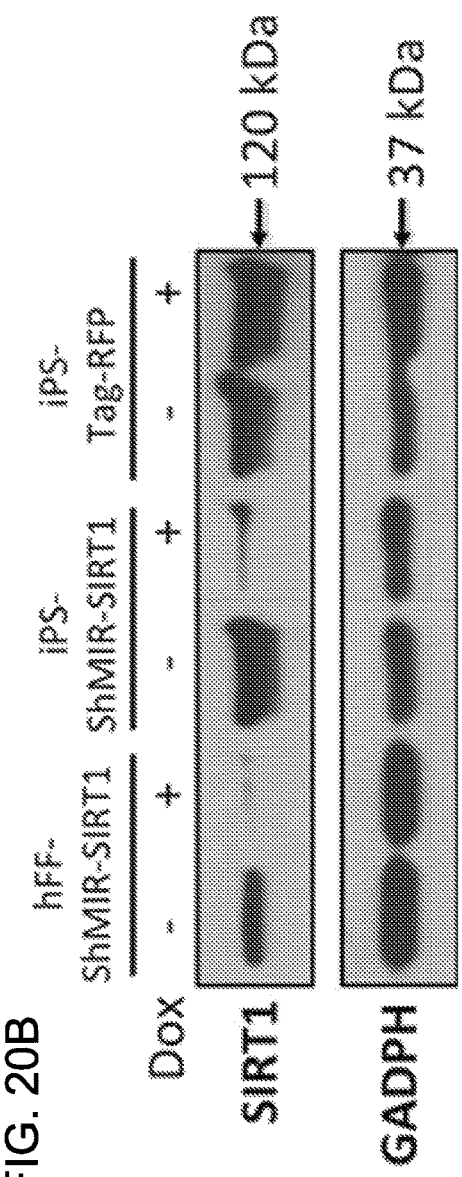

1. Gene Knockdown Systems
- hiPS-Tet-On-shMIR-SIRT1 were engineered, see U.S. Provisional Application No. 62/369,698, incorporated herein by reference.
- To test for SIRT1 knockdown efficiency, doxycycline was added to a final concentration of 0.5 µg/ml and cells were cultivated for 48 h.
- Total RNA was isolated from each well and 1 µg was reverse transcribed using a mixture of Random Hexamer and Oligo-dT primer. The expression of each SIRT1 was determined by quantification of the target cDNA expression levels relative non-induced cells and a reference gene (FIG. 20A).
- Protein was extracted and analyzed for SIRT1 expression (FIG. 20B).

2. Generation of Human Livers in the Rat with hiPS-Tet-On-shRNA-SIRT1
- hiPS-Tet-On-ShRNA-SIRT1 cells can be differentiated into iHeps using methods developed in "1—Differentiation of hiPS cells into hepatocytes" and repopulate immunodeficient rat livers (Il2rg$^{-/-}$ or Rag2/−, Il2rg$^{-/-}$, ALB-iCasp9 models) using methods developed, see "Generation of patient-specific iPS-derived hepatocytes for cell therapy".
- After complete repopulation, addition of doxycycline (2 mg/mL in sucrose water) provides a humanized rat liver model with a specific and conditional knockdown against SIRT1.

Example 7

Generation of Patient-Specific iPS-Derived Hepatocytes for Cell Therapy iPSC cells can be indefinitely maintained in vitro in an undifferentiated state and yet are capable of differentiating into virtually any cell type. Methods are provided herein wherein somatic cells are used to prepare induced pluripotent stem cells that are highly efficient for knock-in and/or knock out of one or more genes of interest.

A—Mass Production of Human iPS-Derived Hepatocytes in the Rat for Transplantation.
- iPS cells are derived from a patient's blood or skin biopsy using Yamanka's protocol, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.
- The iPS cells can be differentiated into hepatocytes as described herein and transplanted in immunocompromised animals, such as liver preconditioned Rag2$^{-/-}$ Il2rg$^{-/-}$ ALB-iCasp9 or XSCID rats, for production of fully functional, fully mature autologous hepatocytes.
- These patient-derived iPS-hepatocytes can be used for clinical autologous-cell transplantation. If patients derived iPS cells have a single mutation that cause a metabolic genetic liver disease (e.g. but not limited to urea cycle disorders, branched-chain amino acids disorders, crigler-najjar syndrome, primary hyperoxaluria, familial hypercholesterolemia, niemann-pick type c, cholesteryl ester storage disease, Wilson disease, neonatal hemochromatosis, tyrosinemia, glycogenstorage disease, alpha-1-antitrypsisn deficiency, mitochondria defects, Phenylketonuria). These patient-derived iPS-hepatocytes can be gene edited and transplanted back into the patient by cell infusion directly into the patients liver using the portal vein route.
- These patient-derived iPS-hepatocytes can be used for bioengineering liver grafts for autologous-transplantation. For example, see PCT Publication No. WO 2015/168254, entitled METHOD OF PREPARING ARTIFI- CIAL ORGANS, AND RELATED COMPOSITIONS, incorporated herein by reference.

Robust Expansion of Human Primary Hepatocytes and iPSC-Heps-Rat Livers

The disclosed animal model generated human iPSCs-Heps that proliferate in a rat model that can deliver an effective regenerative stimulus were evaluated. It was determined that nearly 70-80% of the rat liver can be repopulated 90 days after transplantation of human primary adult or fetal hepatocytes (>5 different human adult or fetal cell donors tested) or human iPSCs-Heps (>3 different human iPS cell lines tested) (FIG. 24A) produced using the presently disclosed protocols. 90 days after transplant, animals were sacrificed and the liver tissue was fixed in 4% PFA and embedded in Paraffin. Histological sections from each lobe of the liver were subjected to immunohistochemistry for human specific-albumin. Quantification of albumin-positive cells was performed by counting approximately 500-800 hepatocytes on 10 images per animal at ×20 magnification using ImageJ software. In addition, blood samples were taken through the lateral tail vein of the rats every month after transplantation to extract serum. Serum human alpha-1-antitrypsin was examined with Human Alpha-1-Antitrypsin ELISA Kit (Bethyl Laboratories) and compared to human serum. The extent of regeneration using the human iPSCs-Heps was comparable to that of freshly isolated human adult and fetal hepatocytes (FIG. 24A). These experiments demonstrate that rat livers can be profusely repopulated with primary human adult hepatocytes, primatery, fetal hepatocytes or human iPSCs-Heps. Thus, the derived human hepatocytes can be enriched and used for different purposes.

Example 8

Plasmid for the Production of Transgenic Rats

The pEALB123-iCasp9_IRES-GFP plasmid was constructed by cloning the rat promoter/enhancer sequence of albumin/a fetoprotein from the plasmid pEALB123CAT (Wen and Locker, Blood 2005, 105:4247-54, incorporated herein by reference) with the FKBP12(V36)-p30Caspase9 sequence from the plasmid pMSCV-F-del Casp9.IRES.GFPz9 (Straathof et al., Blood 2005, 105:4247-54, incorporated herein by reference) (Addgene Plasmid #15567). The rat albumin promoter used in this plasmid is only expressed in rat hepatocytes, ensuring that only rat hepatocytes can express FKBP12(V36)-p30Caspase9 sequence. This modified Caspase 9 system is fused to a modified FK-binding protein, allowing conditional dimerization. Upon addition of a small molecule (Chemical Inducer of Dimerization, e.g. AP1903 or AP20187), the system dimerizes and caspase 9 becomes activated, resulting in rapid apoptosis of the cells expressing the modified Caspase 9. See FIGS. 13A-B and 21.

Example 9

Hepatic Maturation of Human iPSC-Heps in Regenerating Livers

Figure 22A:
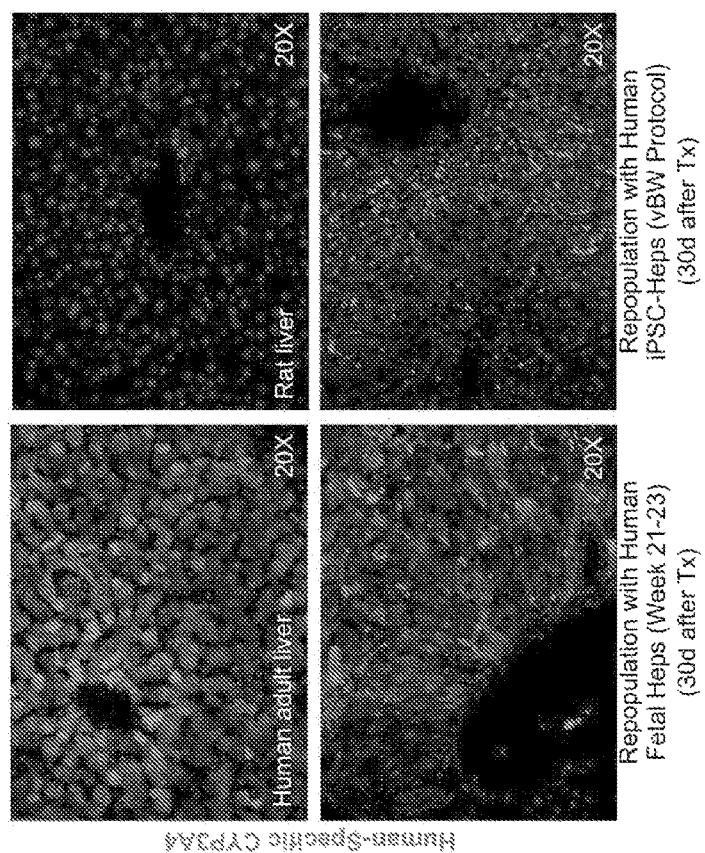
FIGS. 22A-22B. Functional hepatic maturation of human iPSC-Heps (presently disclosed methods) before and after liver repopulation. (A) At the end the hepatic-directed differentiation protocol, human iPSC-Heps did not express the mature human-specific Cytochrome P450 3A4 (CYP3A4) and produce alpha-1-anti-trypsin (A1AT) and urea at the level of freshly isolated human fetal hepatocytes (gestational age 22 weeks) (n=3 each group). (B) After just 30 days (d) in the regenerating rat livers, the colonies of human iPSC-Heps expressed the mature enzyme CYP3A4.
Figure 22B:
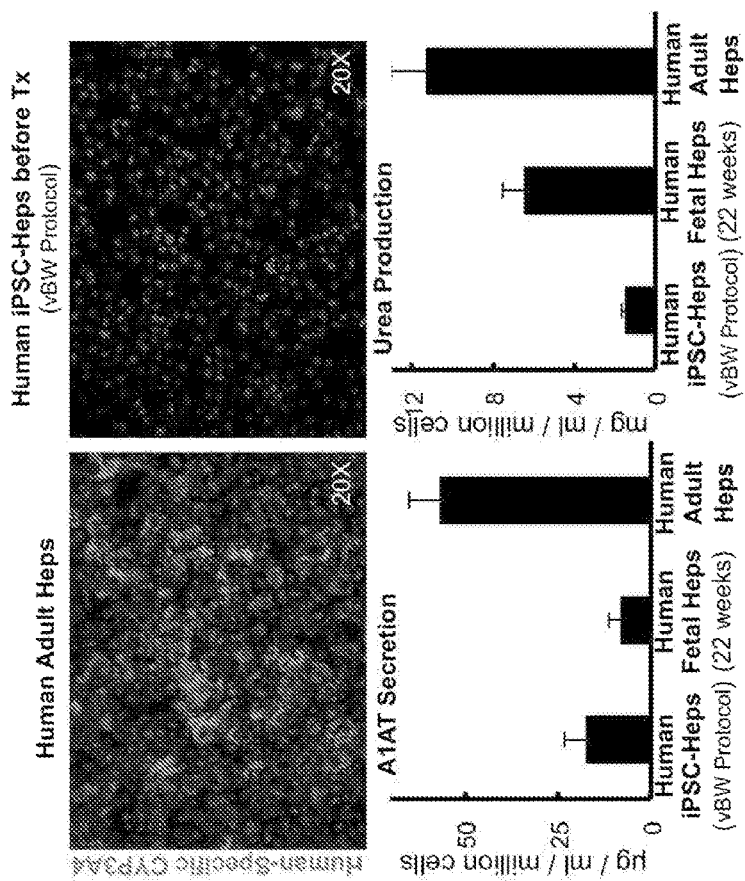

To determine the capacity of differentiated human iPSCs to function as primary hepatocytes, expression of mature human-specific Cytochrome P450 3A4 (CYP3A4) was examined by immunofluorescence of cultured cells. Human iPSC-Heps produced using the methods disclosed herein did not express mature CYP3A4 as compared to freshly isolated normal human adult hepatocytes. In addition, the ability to produce human alpha-1-antitrypsin (A1AT) and urea in culture was examined (FIG. 22A). The culture medium was tested with Human Alpha-1-Antitrypsin ELISA Kit (Bethyl Laboratories) and ABNOVA™ Urea Assay Kit. ABNOVA™ Corporation KA1652 (Thermofisher) according to the manufacturer's instructions and compared to controls. Human iPSC-Heps produced 30% of A1AT and 20% of urea compared to freshly isolated primary human hepatocytes (FIG. 22A). The expression of CYP3A4 after cell transplantation in repopulated immunosuppressed-rats was examined through immunofluorescence and found to appear at 30 days (d). These results show that human iPSCs-Heps possess the ability to mature in situ, and hence can demonstrate hepatic adult functionality after transplantation in in vivo bioreactors.

Example 10

Human iPSC-Heps Proliferate In Vitro

Figure 23B:
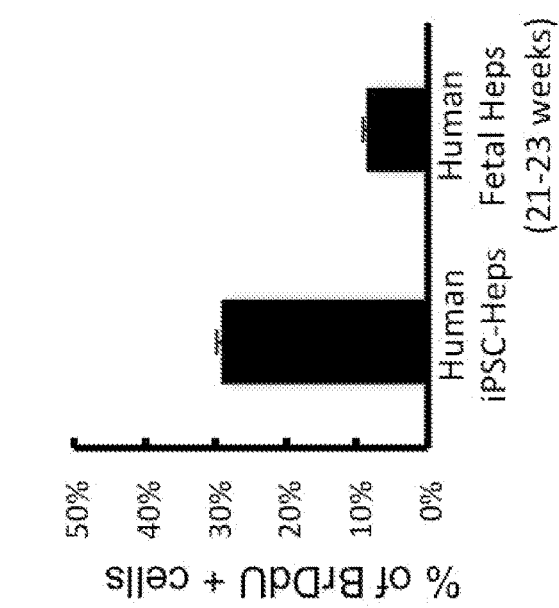
FIGS. 23A-23B. Proliferation of human iPSC-Heps and human primary fetal heps. (A) Primary human fetal hepatocytes are in constant replication. Proliferation capacity in culture of either human iPSC-Heps and human primary fetal heps (n=3 for each group) was measured for 12 hours (h) by bromodeoxyuridine (BrdU) immunofluorescence (bright dots)-labeling and quantified. Human iPSC-Heps showed constant proliferation after hepatic differentiation. Scale bar.
Figure 23A:
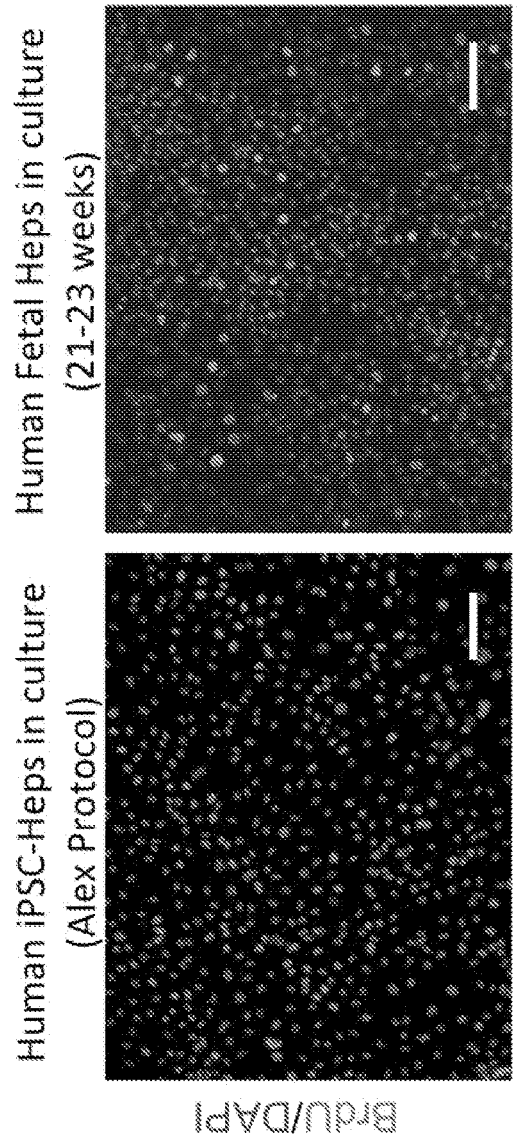

The proliferation capacity of HiPSCs-Heps was evaluated via BrdU incorporation. Bromodeoxyuridine (BrdU) (Invitrogen) was administered to the medium at a concentration of 10 uL/mL for 12 hours (h). Proliferation was analyzed by immunofluorescence of BrdU counterstained with DAPI. Three different areas and at least 100 nuclei per area positive for BrdU immunofluorescence were quantified. Normal fetal liver cells are in continuous growth and when experimentally infused into rat livers are able to selectively proliferate in response to a regenerative stimulus (or hepatic parenchymal loss) (Dabeva et al., Am J Pathol 2000; 156:2017-31). Approximately 30% of human iPSCs-Heps and 10% of freshly isolated human fetal Heps were positive for BrdU (FIG. 23A). These data demonstrate that human iPSCs-Heps have an active cell cycle and proliferate after hepatic differentiation in vitro.

Example 11

High Enrichment of Human Liver Cells

To isolate human cells and eliminate the presence of rat cells, cell suspensions were prepared containing 25% human liver cells and 75% rat liver cells. The human/rat cell suspensions were immunomagnetically labeled with rat MHC class 1 (RT1A) and sorted by magnetic-activated cell sorting (MACS). Several protocols were tested to optimize antibody concentrations and the time of incubation were tested. Groups A to F were tested using different concentrations of anti-phycoerythrin (PE) MicroBeads UltraPure and MACS Columns types. Cell fractions were analyzed by flow cytometry for expression of Human leukocyte antigen (HLA-1 ABC) and (RT1A). (Groups A to F, FIG. 26B). High purity isolation was achieved.

A—Isolation of Livers (FIG. 25)
Primary hepatocytes from humanized livers rats were isolated by liver perfusion under isoflurane anesthesia. Briefly, the liver was initially perfused through the inferior vena cava (IVC) with EGTA, followed by L-Buffer and finally with LIBERASE™ (Roche Applied Science, Branford, Conn.) for 10 to 15 min.
Within the cell culture hood, cell a cell scraper was used to gently disperse the cells with shaking.

After isolation, cells are collected in PBE Buffer (Human hepatocyte medium +0.5% BSA+0.2 mM EDTA), centrifuged, washed and counted using a hemocytometer.

B—Sorting Human Cells with MACS® Separator Technology

Cells were incubated with an anti-rat antibody (i.e. anti-RT1A, or any rat specific marker, labeled with PE) diluted from 1:100 to 1:5 and at a concentration of 1 mL/10×10$^6$ cells for 30 min at 4° C.

Cells were washed with 1 mL of PBE Buffer (Human hepatocytes medium +0.5% BSA +0.2 mM EDTA) for 5×10$^6$ cells and centrifuged at 50 G for 5 min.

Cells were incubated with anti PE microbeads (MACS Miltenyi Biotec, Auburn, Calif.) diluted from 1:10 to 1:2.5 and at a concentration of 1 mL/100×10$^6$ cells for 14 min at 4 C.

Cells were washed with 1 mL of PBE Buffer (Human hepatocytes medium +0.5% BSA +0.2 mM EDTA) for 5×10$^6$ cells and centrifuged at 50 G for 5 min.

Cells were re-suspended in PBE buffer and sorted through a magnetic field of a MACS separator using a CS column (MACS Miltenyi Biotec, Auburn, Calif.) according to the manufacturer's instructions.

Cell purity was evaluated by flow cytometry analysis for human (HLA-1) and rat (RT1A) membrane markers. Different protocols were tested (Group A-F) (FIG. 26B) with various RT1A antibody concentrations and two different magnetic columns. The best protocol enriched human liver cells to approximately 99.9% (FIG. 26B), indicating that rat cells were depleted completely from the cell suspension. This protocol can be used for sorting up to 1 billion liver cells per sorting (sufficient capacity for sorting a cell suspension from a whole rat liver) with almost complete enrichment of human cells. These results show that magnetic cell sorting based on the surface marker RT1A is effective to enrich the human population. These studies demonstrate that human cells can be highly enriched using magnetic-based sorting.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for producing human hepatocytes, comprising:
   a) culturing human induced pluripotent stem cells (iPSC) in a first medium comprising activin A, fibroblast growth factor (FGF)-2 and bone morphogenic protein (BMP)-4 for about 2 to about 3 days, such that mesendoderm cells are obtained;
   b) culturing the mesendoderm cells in a second medium comprising activin A, and in absence of FGF-2 and BMP-4, for about 2 to about 3 days, such that definitive endoderm cells are obtained;
   c) culturing the definitive endoderm cells in a third medium comprising dimethyl sulfoxide (DMSO), and hepatocyte growth factor (HGF), wherein the third medium is a low glucose medium, for about eight to about 14 days, such that hepatic progenitors are obtained; and
   d) culturing the hepatic progenitors in a fourth medium comprising HGF, urso deoxycholic acid, cholesterol, palmitic acid, oleic acid, and rifampicin, wherein the fourth medium is a low glucose medium such that human hepatocytes are obtained.

2. The method of claim 1, wherein the first medium comprises about 50 to about 200 ng/ML of activin A, about 10 to about 50 ng/mL of FGF-2, and about 20 to about 100 ng/mL of BMP-4.

3. The method of claim 1, wherein the second medium comprises about 50 to about 200 ng/mL of activin A.

4. The method of claim 3, wherein the second medium further comprises an effective amount of L-glutamine.

5. The method of claim 1, wherein the first medium and the second medium are replenished daily.

6. The method of claim 1, wherein the third medium comprises about 1 to about 3 percent volume/volume (v/v) DMSO and about 20 to about 150 µg/mL of HGF.

7. The method of claim 6, wherein the third medium further comprises about 0.5 to about 2% v/v L-glutamine.

8. The method of claim 1, wherein the fourth medium comprises about 20 to about 150 µg/mL HGF, about 50 mM to about 150 mM urso deoxycholic acid, about 10 µM to about 50 µM palmitic acid, about 10 µM to about 50 µM about oleic acid, and about 10 µM to about 50 µM rifampicin.

9. The method of claim 8, wherein the fourth medium further comprises an effective amount of L-glutamine, DMSO, and/or dexamethasone.

10. The method of claim 9, wherein the fourth medium comprises about 0.5 to about 2% v/v L-glutamine.

11. The method of claim 9, wherein the fourth medium comprises about 1 to about 3% v/v DMSO.

12. The method of claim 9, wherein the fourth medium comprises about 0.5 to about 2 mM dexamethasone.

13. The method of any one of claim 1, wherein the third medium and the fourth medium are replenished every other day.

14. The method of claim 1, further comprising:
   e) transplanting the hepatic progenitors and/or the human hepatocytes into a liver of an immunocompromised non-human animal, thereby expanding the hepatic progenitors and/or the human hepatocytes and producing human hepatocytes; and
   f) harvesting the expanded hepatic progenitors and/or the human hepatocytes.

15. The method of claim 14, wherein the immunocompromised non-human animal is a transgenic rat.

16. The method of claim 15, wherein the transgenic rat is a transgenic Rag2$^{-/-}$ Il2rg$^{-/-}$ rat whose genome comprises a nucleic acid molecule encoding a fusion protein operably linked to a liver-specific promoter, wherein the fusion protein comprises FKBP12 and caspase 9, and the rat is capable of expanding human hepatocytes in its liver.

17. The method of claim 16, wherein the promoter is an albumin promoter.

18. The method of claim 16, wherein the hepatic progenitors and/or the human hepatocytes are expanded in the transgenic Rag2$^{-/-}$ Il2rg$^{-/-}$ rat for about 3 days to about 24 months.

19. The method of claim 14, further comprising inhibiting growth of non-human hepatocytes of the immunocompromised non-human animal prior to transplanting the hepatic progenitors and/or the human hepatocytes into the liver.

20. The method of claim 19, wherein inhibiting growth of the non-human hepatocytes comprises administering an effective amount of radiation or retrorsine to the immunocompromised non-human animal.

21. The method of claim 14, wherein about $0.5 \times 10^6$ to about $10 \times 10^6$ human hepatocytes are transplanted into the immunocompromised non-human transgenic animal.

22. The method of claim 14, wherein about $0.5 \times 10^6$ to about $10 \times 10^6$ human hepatocytes are transplanted into the immunocompromised non-human transgenic animal.

23. A method for producing human hepatocytes, comprising
   a) culturing human induced pluripotent stem cells (iPSC) in a first medium comprising activin A, fibroblast growth factor (FGF)-2 and bone morphogenic protein (BMP)-4 for about 2 to about 3 days, such that mesendoderm cells are obtained;

b) culturing the mesendoderm cells in a second medium comprising activin A, and in absence of FGF-2 and BMP-4, for about 2 to about 3 days, such that definitive endoderm cells are obtained;

c) culturing the definitive endoderm cells in a third medium comprising dimethyl sulfoxide (DMSO), and hepatocyte growth factor (HGF), wherein the third medium is a low glucose medium for about eight to about 14 days, such that hepatic progenitors are obtained;

d) transplanting the hepatic progenitors into a liver of a transgenic Rag2$^{-/-}$ Il2rg$^{-/-}$ rat whose genome comprises a nucleic acid molecule encoding a fusion protein operably linked to a liver-specific promoter, wherein the fusion protein comprises FKBP12 and caspase 9, and the transgenic Rag2$^{-/-}$ Il2rg$^{-/-}$ rat is capable of expanding human hepatocytes in its liver; and e) harvesting human hepatocytes from the liver of the transgenic Rag2$^{-/-}$ Il2rg$^{-/-}$ rat.

24. The method of claim 23, wherein the first medium comprises about 50 to about 200 ng/ML of activin A, about 10 to about 50 ng of FGF-2, and about 20 to about 100 ng/mL of BMP-4.

25. The method of claim 23, wherein the second medium comprises about 50 to about 200 ng/mL of activin A.

26. The method of claim 25, wherein the second medium further comprises an effective amount of L-glutamine.

27. The method of claim 23, wherein the first medium and the second medium are replenished daily.

28. The method of claim 23, wherein the third medium comprises about 1 to about 3 percent v/v DMSO and about 20 to about 150 μg/mL of HGF.

29. The method of claim 28, wherein the third medium further comprises about 0.5 to about 2% v/v L-glutamine.

30. The method of claim 23, wherein the third medium and the fourth medium are replenished every other day.

31. The method of claim 23, further comprising inhibiting growth of endogenous hepatocytes of the transgenic Rag2$^{-/-}$ Il2rg$^{-/-}$ rat prior to transplanting the hepatic progenitors into the liver of the immunocompromised transgenic Rag2$^{-/-}$ Il2rg$^{-/-}$ rat.

32. The method of claim 31, wherein inhibiting growth of the endogenous hepatocytes comprises administering an effective amount of radiation or retrorsine to the transgenic Rag2$^{-/-}$ Il2rg$^{-/-}$ rat.

33. The method of claim 23, wherein the liver specific promoter is an albumin promoter.

34. The method of claim 23, wherein inhibiting growth of the non-human hepatocytes comprises administering an effective amount of AP1903 or AP20187 to the transgenic Rag2$^{-/-}$ Il2rg$^{-/-}$ rat.

35. The method of claim 23, wherein the hepatic progenitors are expanded in the transgenic Rag2$^{-/-}$ Il2rg$^{-/-}$ rat for about 3 days to about 24 months.

36. The method of claim 23, wherein the iPSC is transformed with a heterologous nucleic acid molecule operably linked to a promoter.

37. The method of claim 23, wherein the human hepatocytes comprise a heterologous nucleic acid operably linked to a promoter.

38. The method of claim 37, wherein the heterologous nucleic acid is a shRNA or encodes Cas9.

39. A transgenic Rag2$^{-/-}$ Il2rg$^{-/-}$ rat whose genome comprises a nucleic acid molecule encoding a fusion protein operably linked to a liver-specific promoter, wherein the fusion protein comprises FKBP12 and caspase 9, and the rat is capable of expanding human hepatocytes in its liver.

40. The transgenic Rag2$^{-/-}$ Il2rg$^{-/-}$ rat of claim 39, wherein the promoter is an albumin promoter or a transthyretin promoter.

* * * * *

SEQUENCE LISTING

```
<160> NUMBER OF SEQ ID NOS: 48

<210> SEQ ID NO 1
<211> LENGTH: 334
<212> TYPE: DNA
<213> ORGANISM: Artificial Sequence
<220> FEATURE:
<223> OTHER INFORMATION: deoxycycline promoter

<400> SEQUENCE: 1
atcgatacta gactcgagtt tactccctat cagtgataga gaacgtatga agagtttact      60
ccctatcagt gatagagaac gtatgcagac tttactccct atcagtgata gagaacgtat     120
aaggagttta ctccctatca gtgatagaga acgtatgacc agtttactcc ctatcagtga     180
tagagaacgt atctacagtt tactccctat cagtgataga gaacgtatat ccagtttact     240
ccctatcagt gatagagaac gtataagctt taggcgtgta cggtgggcgc ctataaaagc     300
agagctcgtt tagtgaaccg tcagatcgcc tgga                                  334

<210> SEQ ID NO 2
<211> LENGTH: 1368
<212> TYPE: PRT
<213> ORGANISM: Streptococcus pyogenes

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510
```

```
Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
```

```
                 930             935             940
Glu Asn Asp Lys Leu Ile Arg Glu Val Lys Val Ile Thr Leu Lys Ser
945                 950             955                 960

Lys Leu Val Ser Asp Phe Arg Lys Asp Phe Gln Phe Tyr Lys Val Arg
                965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335
```

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 3
<211> LENGTH: 83
<212> TYPE: DNA
<213> ORGANISM: Artificial Sequence
<220> FEATURE:
<223> OTHER INFORMATION: tracrRNA

<400> SEQUENCE: 3
gttttagagc tagaaatagc aagttaaaat aaggctagtc cgttatcaac ttgaaaaagt    60
ggcaccgagt cggtgctttt ttt                                           83

<210> SEQ ID NO 4
<211> LENGTH: 249
<212> TYPE: DNA
<213> ORGANISM: Artificial Sequence
<220> FEATURE:
<223> OTHER INFORMATION: U6 promoter

<400> SEQUENCE: 4
gagggcctat ttcccatgat tccttcatat ttgcatatac gatacaaggc tgttagagag    60
ataattggaa ttaatttgac tgtaaacaca agatattag tacaaaatac gtgacgtaga   120
aagtaataat tcttgggta gtttgcagtt taaaattat gttttaaaat ggactatcat    180
atgcttaccg taacttgaaa gtatttcgat ttcttggctt tatatatctt gtggaaagga   240
cgaaacacc                                                          249

<210> SEQ ID NO 5
<211> LENGTH: 378
<212> TYPE: DNA
<213> ORGANISM: Artificial Sequence
<220> FEATURE:
<223> OTHER INFORMATION: DNA encoding U6 sgRNA

<400> SEQUENCE: 5
ggcgcgccgg atccgagggc ctatttccca tgattccttc atatttgcat atacgataca    60
aggctgttag agataatt ggaattaatt tgactgtaaa cacaaagata ttagtacaaa   120
atacgtgacg tagaaagtaa taatttcttg ggtagtttgc agttttaaaa ttatgtttta   180
aaatggacta tcatatgctt accgtaactt gaaagtattt cgatttcttg ctttatata   240 tcttgtggaa aggacgaaac accggaagag cgagctcttc ggttttagag ctagaaatag   300
caagttaaaa taaggctagt ccgttatcaa cttgaaaaag tggcaccgag tcggtgcttt   360
ttttggtacc ggcgcgcc                                                378

<210> SEQ ID NO 6
<211> LENGTH: 966
<212> TYPE: DNA
<213> ORGANISM: Artificial Sequence
<220> FEATURE:
<223> OTHER INFORMATION: U6 promoter

<400> SEQUENCE: 6
cgatacaagg ctgttagaga gataattaga attaatttga ctgtaaacac aaagatatta    60
gtacaaaata cgtgacgtag aaagtaataa tttcttgggt agtttgcagt tttaaaatta   120

```
tgttttaaaa tggactatca tatgcttacc gtaacttgaa agtatttcga tttcttggct    180
ttatatatct tgtggaaagg acgaaacacc ggagacggtt gtaaatgagc acacaaaata    240
cacatgctaa atattatat tctatgacct ttataaaatc aaccaaaatc ttctttttaa     300
taactttagt atcaataatt agaatttta tgttccttt tgcaaacttt taataaaaat     360
gagcaaaata aaaaaacgct agttttagta actcgcgttg ttttcttcac ctttaataat    420
agctactcca ccacttgttc ctaagcggtc agctcctgct tcaatcattt tttgagcatc    480
ttcaaatgtt ctaactccac cagctgcttt aactaaagca ttgtctttaa caactgactt    540
cattagttta acatcttcaa atgttgcacc tgattttgaa atcctgttg atgttttaac     600 aaattctaat ccagcttcaa cagctatttc acaagctttc atgatttctt cttttgttaa    660
taaacaattt tccataatac atttaacaac atgtgatcca gctgcttttt ttacagcttt    720
catgtcttct aaaactaatt cataattttt gtcttttaat gcaccaatat ttaataccat    780
atcaatttct gttgcaccat ctttaattgc ttcagaaact tcgaatgctt ttgtagctgt    840
tgtgcatgca cctagaggaa aacctacaac atttgttatt cctacatttg tgccttttaa    900
taattcttta caatagcttg ttcaatatga attaacacaa actgttgcaa aatcaaattc    960
aattgc                                                              966

<210> SEQ ID NO 7
<211> LENGTH: 12525
<212> TYPE: DNA
<213> ORGANISM: Artificial Sequence
<220> FEATURE:
<223> OTHER INFORMATION: Plasmind construct
<220> FEATURE:
<221> NAME/KEY: misc_feature
<222> LOCATION: (12116)..(12119)
<223> OTHER INFORMATION: n is a, c, g, or t

<400> SEQUENCE: 7
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540 accctgcct agggaccacc gacccccccg ccgggaggta agctggccag cggtcgtttc    600
gtgtctgtct ctgtctttgt gcgtgtttgt gccggcatct aatgtttgcg cctgcgtctg    660
tactagtccg cggacactgc tgtaactctc cttgacctat atcgatgttc tagtgtacct    720
ttattgactt tgacatattt ctgtcctttt aagttcggcg ggcagctcgg ttgctcaatt    780
cgtctctgga ctcttttact ttgttcctgt gtggggaag aaaaaatatt ttctcctcta    840
aacaccaaag atccaaagat aaaattcctt tgatggaggg aaaacagccc ccttccccca    900
ttttgatttt ctttcgagcg aaacatgttc acagccaacg gggagggtaa aggattcccc    960 ccccccgccca gataggctcg aattaaacaa aggagggaga gttgacagaa accaaccaag   1020
gggaggatta tggtgacgtc tggggctaga tgtgaagaga tcaaggaaga aaccagcaga   1080
```

-continued

```
gaagacattg gtcaggcttg tcatgagcag tgtgatggtg cctatacatt ttcatgctgg    1140
gcagaaacat cttttccacat ttgacctcca gttccttgat gtaatcatat gtttggggtt   1200
ccttgagaaa gtgtggggag agtcttcata tattagctca aggaacatgt atagaatagg    1260
tagagagaat ttagcagcat tagggaaaca gacaaagaaa acgtcaggca aactgtgggc    1320
tgccctctca atccttgagt tcccagtaat ttagagacta taacagtcac gagatcgttc    1380
tctgctcaca gataacaaga gcaggggta agtgtaacaa atcttcaga gtaaggaggg      1440 ccatagtggt ctaaaacact ccttatagtt ggagtgcgtc gctttgcagg gttcatttga    1500
aaatctgaag gtttccttgc gagacgctag attccatacc attctcacat atgcttttgt    1560
gcctgtggag tttcagacct agataagaga atgattgaat atttcactaa cgttctgtta    1620
ccagaagagc gtgagaggcg tgtgattcat ttgtgggcgt aaatcgctga ctaccatttg    1680
attcgatgac atttgatttc tgtttgtaaa gatgatgctg tgtttcggat gttgtgctaa    1740
gcaccatggt aaatgcaaga agttaatcat ctgggaaagg gccagattgc ctcccagaag    1800
actgggactt aagggcacac atgaagttcc ctgagaagtc aatctagaga gtgttagaag    1860
ttgtcagaga gggaccttct ctagtgagtg ctaaacaccc acagacaatt atatgatcga    1920
tgccttgaga actggtggta agttattata agcattgaag ggcaaggcac tagaaatgta    1980
agaactatgc tttcatggaa cacacacaca gacacacaca cagatacccca catgcacaca   2040 cacacacatg cacacgcaca cagacacaca catacacaca gacatacata cacacacagc    2100
acatacacac atacatacat gcacacacag agagcaagca cacacagaga gagtcataca    2160
cacacacaca caaacacaca aacacacaaa cacacagca gacacaaaca gacacagcaa     2220
aaaggatcct gaaggagtga aagtcatttt ctgccaactc acatgtgcag tctaactgtg    2280
cattctagaa gtgccagtcc taagaatggt gatatttact cacaccttt tagaaatatt     2340 tgtagctgtc cagcatttag gacacaccac tccgcctcca cacatgaaag tatactttca    2400
gagaagtatt attttgtgag atgaatcata agactcagaa tcagtcatgt taaattattc    2460
accgaatgtc ataggactga taactggcac acacacgatt agcatcttct gatggcgggg    2520
ttcagtttac cgggtcacgc tgcactgggg aagattcgag gatttatgga aaaagtcaac    2580
agaacaagaa ttggagcagc cggaaagtat ttgctgcgaa ctctgtactt aggacttagc    2640
tttgagcaat agccccgaaa ggttttagca ctgtttgcgg tcagcacaca aaccgtggtt    2700
caaagctcct ccttatctct tcctgcggca tttgccgtct ctggttctgc acacggtttc    2760
tcacccgctc ccacacacct acactaagcc ctgtaagctg gagctattcc agtatccatc    2820
ccctctgtgt gattctggag ataggaagca atacaccagt gcctgtcaac ttcttcgatc    2880
tgcaaatcag ggtgtttggc ccacaacatt cctgggagta aaaagcaagc ttggattaca    2940
ttaactcacc acatactaaa ccagaaccag tagggtaaac caatctctgt ctctgtctct    3000
ctgtctctct ccctcactcc ctcttgcttt tctctctagga gtcagtatgt gtgaacttag   3060
cttttaaagc attttttttct ttaatttttac ttcatccaca ttacgaaatt ttatgtggat   3120
ttctcacttc ctgtcagcga tgccttcacc cacgtggctt tgttagatta cacattgcag    3180
tagtttaatt ggtctcatct cttttttgaca gcagcagaga cattttcaaa ggacagagat    3240
gatttttttt ttttaccagc tcctctttga ggtccttcat gaagcgggaa cacgaggtcc     3300
ttaagagaca gcctgtgcca gcctcatcaa aaacactgcc cccattaggt tgccagtagg     3360 taaagcccctt agcatcatag tcttagccac ctgagttcca tctctggagc tctcagaaga    3420
```

```
gcggagagag agatcagact ctacagggtt gcctctgact gccactgagg gtctgccaac    3480 ttttttgtgtc atggggagtt gaacccagag cctcacacaa actcggcgag ccacgatccg    3540
ctgagtcctg ccatttctga acactgtgtc tcacatattg cctttcttct cattcctgaa    3600
ctacgctgtt ctctccatta atgggtctct cgctgtcttt tacaattcct cgaggtaaaa    3660
ggcaagcctt gctattcggc ctacctacca acttttcttt gggtctcttg gaaatgtgac    3720
ttcctctaaa ataccctcac cggtagaaag acactaggag ctgttttcct tccacatagc    3780
aggacatcca tcagagaact tggatacagt ggatgcagtc attttccac cagatgagat    3840 gtggtctcag tcagtaatgc tgacactcat tgctgacact tcccttcagt gaacaacatc    3900
tcatatgcgg acttcacact ttttgttgaa tgaatcatgg aaccccaac tgttgagttc    3960 tacttggtgg cggccctatt ctgagtgacc ctcttactag tttatctaac cctcgtttat    4020
taaaaaggat attaattttc gtaactataa tttttatatg ttgggagtaa aaccattttg    4080
agtgttttgt ccaatgtcac ctgaccgaca gtttgaatag tcgggggtag agcctttcgt    4140
atactaaagt ccagtttgtt taaccatatt gcttcagtgg ggtttcatgg gctcaggaag    4200
taacgaatga accagacata gagctatgaa aggtatgtgg tgcgagctca gcccttgcga    4260
caaagctttg agcaacagcc cgcgtgggct tagggttgtt tgcagttggt gttagagacc    4320
tcacacaaag tcatgtggca gataacccgg aggcaaaatt caaacccagt cgccatatgc    4380
tcatgtttaa cggtgaccct gtgcaccttt ctgatcacat gctttggaat tgcaaagatc    4440
tccccacaag gcagagtgca gagagaatta aggatgacat aaccctgtgg gctgggctga    4500
tctgggctgc tcctcttggc ttaggtgtag aagcatagca gtgaattggt gactgatata    4560
acgtgtattt attatctata gttttgtgtg tgtgtgtgtg tgtgtgtgtg tgtgtgtgtg    4620
tgtgtgtgtg tatgatcata tttacacatg attcatctag cctttatgaa aggatgatga    4680
aaccagacat ttagccttgc ggttacatgc atactagcaa gaaactcgat ataggatctt    4740
taaaggtagg aagatctcag agtggtcaag gagaggtgta gcacacctgt aatccaggac    4800
ccaggagata ggaaaatcag gaactcaaag ccaactgctc acaaaccgac catgcaaacg    4860
attgaccaaa ctaaaatgga gactcttatt tcactttaaa cccttgtcac tggataaata    4920
cattcattat ctactcagca agtgttgggt cctgtctcaa cacttgacgt gctatgcata    4980
gtgtaaaacg tactcagtgt acttagacca tttattgtta ttttatccaa tgagtaggga    5040
tgagaggaga gggagacaga gacagagaca gagacagaga cagagagaga cagagacaga    5100
gagagacaga gagagacaga gagagacaga gagagagaca gagaggagag agaggagaga    5160
gatagagagg acagagaaga cagagagaag agcagtagac agacacacag agagagagag    5220
agagagagag agagagagag agagagagag agagagagag agagacagag agagacagag    5280
agagagacag atagacacac agagagagaa agagagggag agagagacac agagagagag    5340
gtagacagac agacacacat acacacagac agacagacag acagacacac acacacagag    5400
agagagagag agagagagag agagagagag agagagagag agagagagag agagagagag    5460
gtctgatttc ccttgcaatc tagaaagtta acgttaaact ctggcctgtc attgctttgt    5520
tctattttga gaacaggaag aagtgcaggt atggtctgat aataaggcct tattgtgtgt    5580
gtttcttggt ttctattatt aatatgttat gaaaatcttt ccattacatc aactattaat    5640
ctacaaaatc ggtttgatag cggcattgct ctccatttaa tgaatacact atatttattt    5700
ctggtgtaag tcattttgtt tttataatca catcttaaag gtagctactc acaggctatg    5760
cagatgactc agctgttaag ggcccttcct gctcttctag aggccctagg ttcaattccc    5820
```

```
agcccacagg gcagctcata accacctgtg actccagttc cgagggatcc aatgccctct   5880
tctgacctct gcagcttcag atggcaaaca tacttaaggg atttagttaa acaacttttt   5940
tttttcgaat tggcaaggat catatgattt tgtaatggcg ccggaaccaa tgaaatgcta   6000
gcttagtgtg gttaatgatc taccggtatt ggttagagaa gtatattatc gcgagtttct   6060
ctgcacacag accacctttc ctgtccagat ctgagcttgg cgagattttc aggagctaaa   6120
ttacgccacc atgctcgagg gagtgcaggt ggagactatc tccccaggag acgggcgcac   6180
cttccccaag cgcggccaga cctgcgtggt gcactacacc gggatgcttg aagatggaaa   6240
gaaagttgat tcctcccggg acagaaacaa gcccttaag tttatgctag caagcagga    6300
ggtgatccga ggctgggaag aaggggttgc ccagatgagt gtgggtcaga gagccaaact   6360
gactatatct ccagattatg cctatggtgc cactgggcac ccaggcatca tcccaccaca   6420
tgccactctc gtcttcgatg tggagcttct aaaactggaa tctggcggtg gatccggagt   6480
cgacggattt ggtgatgtcg gtgctcttga gagtttgagg ggaaatgcag atttggctta   6540
catcctgagc atggagccct gtggccactg cctcattatc aacaatgtga acttctgccg   6600
tgagtccggg ctccgcaccc gcactggctc caacatcgac tgtgagaagt tgcggcgtcg   6660
cttctcctcg ctgcatttca tggtggaggt gaagggcgac ctgactgcca agaaaatggt   6720
gctggctttg ctggagctgg cgcggcagga ccacggtgct ctggactgct gcgtggtggt   6780
cattctctct cacggctgtc aggccagcca cctgcagttc caggggctg tctacggcac   6840
agatggatgc cctgtgtcgg tcgagaagat tgtgaacatc ttcaatggga ccagctgccc   6900
cagcctggga gggaagccca agctctttt catccaggcc tgtggtgggg agcagaaaga   6960
ccatgggttt gaggtggcct ccacttcccc tgaagacgag tcccctggca gtaaccccga   7020
gccagatgcc accccgttcc aggaaggttt gaggaccttc gaccagctgg acgccatatc   7080
tagtttgccc acacccagtg acatctttgt gtcctactct actttcccag gttttgtttc   7140
ctggagggac cccaagagtg gctcctggta cgttgagacc ctggacgaca tctttgagca   7200
gtgggctcac tctgaagacc tgcagtccct cctgctagg gtcgctaatg ctgtttcggt   7260
gaaagggatt tataaacaga tgcctggttg ctttaatttc ctccggaaaa aacttttctt   7320
taaaacatca gtcgactatc cgtacgacgt accagactac gcactcgact aagaattcat   7380
cgagcgggat caattccgcc ccccccctaa cgttactggc cgaagccgct tggaataagg   7440
ccggtgtgcg tttgtctata tgttattttc caccatattg ccgtcttttg gcaatgtgag   7500
ggcccggaaa cctggccctg tcttcttgac gagcattcct aggggtcttt ccctctcgc    7560
caaaggaatg caaggtctgt tgaatgtcgt gaaggaagca gttcctctgg aagcttcttg   7620
aagacaaaca acgtctgtag cgacccttg caggcagcgg aacccccac ctggcgacag    7680
gtgcctctgc ggccaaaagc cacgtgtata agatacacct gcaaaggcgg cacaaccca    7740
gtgccacgtt gtgagttgga tagttgtgga aagagtcaaa tggctctcct caagcgtatt   7800
caacaagggg ctgaaggatg cccagaaggt acccccattgt atgggatctg atctggggcc   7860
tcggtgcaca tgctttacat gtgtttagtc gaggttaaaa aacgtctagg cccccccgaac  7920
cacgggacg tggttttcct ttgaaaaaca cgataatacc atggtgagca agggcgagga    7980
gctgttcacc ggggtggtgc ccatcctggt cgagctggac ggcgacgtaa acggccacaa   8040
gttcagcgtg tccggcgagg gcgagggcga tgccacctac ggcaagctga ccctgaagtt   8100
catctgcacc accggcaagc tgcccgtgcc ctggcccacc ctcgtgacca ccctgaccta   8160
```

```
cggcgtgcag tgcttcagcc gctaccccga ccacatgaag cagcacgact tcttcaagtc    8220
cgccatgccc gaaggctacg tccaggagcg caccatcttc ttcaaggacg acggcaacta    8280
caagacccgc gccgaggtga agttcgaggg cgacaccctg gtgaaccgca tcgagctgaa    8340
gggcatcgac ttcaaggagg acggcaacat cctggggcac aagctggagt acaactacaa    8400
cagccacaac gtctatatca tggccgacaa gcagaagaac ggcatcaagg tgaacttcaa    8460
gatccgccac aacatcgagg acggcagcgt gcagctcgcc gaccactacc agcagaacac    8520
ccccatcggc gacggccccg tgctgctgcc cgacaaccac tacctgagca cccagtccgc    8580
cctgagcaaa gaccccaacg agaagcgcga tcacatggtc ctgctggagt tcgtgaccgc    8640
cgccgggatc actctcggca tggacgagct gtacaagtaa agcggccgcg actctagagt    8700
cgacctgcag gcatgcaagc ttcaggtagc cggctaacgt taacaaccgg tacctctaga    8760
actatagcta gcatgcgcaa atttaaagcg ctgtatcga taaaataaaa gattttattt    8820
agtctccaga aaaggggggg aatgaaagac cccacctgta ggtttggcaa gctagcttaa    8880
gtaacgccat tttgcaaggc atggaaaata caactgag aatagagaag ttcagatcaa    8940
ggttaggaac agagagacag cagaatatgg gccaaacagg atatctgtgg taagcagttc    9000
ctgccccggc tcagggccaa gaacagatgg tcccagatg cggtcccgcc ctcagcagtt    9060
tctagagaac catcagatgt ttccagggtg ccccaaggac ctgaaaatga ccctgtgcct    9120
tatttgaact aaccaatcag ttcgcttctc gcttctgttc gcgcgcttct gctccccgag    9180
ctcaataaaa gagcccacaa ccctcactc ggcgcgccag tcctccgata gactgcgtcg    9240
cccgggtacc cgtgtatcca ataaaccctc ttgcagttgc atccgacttg tggtctcgct    9300
gttccttggg agggtctcct ctgagtgatt gactacccgt cagcggggt ctttcatggg    9360 taacagtttc ttgaagttgg agaacaacat tctgagggta ggagtcgaat attaagtaat    9420
cctgactcaa ttagccactg ttttgaatcc acatactcca atactccgta aatagttcat    9480 tatgacagc gcagaaagag ctggggagaa ttgtgaaatt gttatccgct cacaattcca    9540
cacaacatac gagccggaag cataaagtgt aaagcctggg gtgcctaatg agtgagctaa    9600
ctcacattaa ttgcgttgcg ctcactgccc gctttccagt cgggaaacct gtcgtgccag    9660
ctgcattaat gaatcggcca acgcgcgggg agaggcggtt tgcgtattgg gcgctcttcc    9720
gcttcctcgc tcactgactc gctgcgctcg gtcgttcggc tgcggcgagc ggtatcagct    9780
cactcaaagg cggtaatacg gttatccaca gaatcagggg ataacgcagg aaagaacatg    9840
tgagcaaaag gccagcaaaa ggccaggaac cgtaaaaagg ccgcgttgct ggcgtttttc    9900
cataggctcc gcccccctga cgagcatcac aaaaatcgac gctcaagtca gaggtggcga    9960
aacccgacag gactataaag ataccaggcg tttccccctg gaagctccct cgtgcgctct   10020
cctgttccga ccctgccgct taccggatac ctgtccgcct ttctcccttc gggaagcgtg   10080
gcgctttctc atagctcacg ctgtaggtat ctcagttcgg tgtaggtcgt tcgctccaag   10140
ctgggctgtg tgcacgaacc ccccgttcag cccgaccgct gcgccttatc cggtaactat   10200
cgtcttgagt ccaacccggt aagacacgac ttatcgccac tggcagcagc cactggtaac   10260
aggattagca gagcgaggta tgtaggcggt gctacagagt tcttgaagtg gtggcctaac   10320
tacggctaca ctagaaggac agtatttggt atctgcgctc tgctgaagcc agttaccttc   10380
ggaaaaagag ttggtagctc ttgatccggc aaacaaacca ccgctggtag cggtggtttt   10440
tttgtttgca agcagcagat tacgcgcaga aaaaaggat ctcaagaaga tcctttgatc   10500
ttttctacgg ggtctgacgc tcagtggaac gaaaactcac gttaagggat tttggtcatg   10560
```

-continued

```
agattatcaa aaaggatctt cacctagatc cttttaaatt aaaaatgaag ttttaaatca    10620
atctaaagta tatatgagta aacttggtct gacagttacc aatgcttaat cagtgaggca    10680
cctatctcag cgatctgtct atttcgttca tccatagttg cctgactccc cgtcgtgtag    10740
ataactacga tacgggaggg cttaccatct ggccccagtg ctgcaatgat accgcgagac    10800
ccacgctcac cggctccaga tttatcagca ataaaccagc cagccggaag ggccgagcgc    10860
agaagtggtc ctgcaacttt atccgcctcc atccagtcta ttaattgttg ccgggaagct    10920
agagtaagta gttcgccagt taatagtttg cgcaacgttg ttgccattgc tacaggcatc    10980
gtggtgtcac gctcgtcgtt tggtatggct tcattcagct ccggttccca acgatcaagg    11040
cgagttacat gatcccccat gttgtgcaaa aaagcggtta gctccttcgg tcctccgatc    11100
gttgtcagaa gtaagttggc cgcagtgtta tcactcatgg ttatggcagc actgcataat    11160
tctcttactg tcatgccatc cgtaagatgc ttttctgtga ctggtgagta ctcaaccaag    11220
tcattctgag aatagtgtat gcggcgaccg agttgctctt gcccggcgtc aatacgggat    11280
aataccgcgc cacatagcag aactttaaaa gtgctcatca ttggaaaacg ttcttcgggg    11340
cgaaaactct caaggatctt accgctgttg agatccagtt cgatgtaacc cactcgtgca    11400
cccaactgat cttcagcatc ttttactttc accagcgttt ctgggtgagc aaaaacagga    11460
aggcaaaatg ccgcaaaaaa gggaataagg gcgacacgga aatgttgaat actcatactc    11520
ttcctttttc aatattattg aagcatttat cagggttatt gtctcatgag cggatacata    11580
tttgaatgta tttagaaaaa taaacaaata ggggttccgc gcacatttcc ccgaaaagtg    11640
ccacctgacg tctaagaaac cattattatc atgacattaa cctataaaaa taggcgtatc    11700
acgaggccct ttcgtctcgc gcgtttcggt gatgacggtg aaaacctctg acacatgcag    11760
ctcccggaga cggtcacagc ttgtctgtaa gcggatgccg ggagcagaca gcccgtcag     11820
ggcgcgtcag cgggtgttgg cgggtgtcgg ggctggctta actatgcggc atcagagcag    11880
attgtactga gagtgcacca tatgcggtgt gaaataccgc acagatgcgt aaggagaaaa    11940
taccgcatca ggcgccattc gccattcagg ctgcgcaact gttgggaagg gcgatcggtg    12000
cgggcctctt cgctattacg ccagctggcg aaagggggat gtgctgcaag gcgattaagt    12060
tgggtaacgc cagggttttc ccagtcacga cgttgtaaaa cgacggccag tgccannnnc    12120
gctctcccct atgcgactcc tgcattagga agcagcccag tagtaggttg aggccgttga    12180
gcaccgccgc cgcaaggaat ggtgcatgca aggagatggc gcccaacagt ccccggcca    12240
cggggcctgc caccataccc acgccgaaac aagcgctcat gagcccgaag tggcgagccc    12300
gatcttcccc atcggtgatg tcggcgatat aggcgccagc aaccgcacct gtggcgccgg    12360
tgatgccggc cacgatgcgt ccggcgtaga ggcgattagt ccaatttgtt aaagacagga    12420
tatcagtggt ccaggctcta gttttgactc aacaatatca ccagctgaag cctatagagt    12480
acgagccata gataaaataa aagatttat ttagtctcca gaaaa               12525
```

<210> SEQ ID NO 8
<211> LENGTH: 6119
<212> TYPE: DNA
<213> ORGANISM: Artificial Sequence
<220> FEATURE:
<223> OTHER INFORMATION: pEALB123CAT

<400> SEQUENCE: 8

```
tgaaagaccc cacctgtagg tttggcaagc tagcttaagt aacgccattt tgcaaggcat    60
```

-continued

| | | | | | |
|---|---|---|---|---|---|
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcgg | cgcgccagtc | ctccgataga | ctgcgtcgcc | cgggtacccg | tattcccaat | 420 |
| aaagcctctt | gctgtttgca | tccgaatcgt | ggactcgctg | atccttggga | gggtctcctc | 480 |
| agattgattg | actgcccacc | tcggggtct | ttcatttgga | ggttccaccg | agatttggag | 540 |
| accccctgcct | agggaccacc | gaccccccg | ccgggaggta | agctggccag | cggtcgtttc | 600 |
| gtgtctgtct | ctgtctttgt | gcgtgtttgt | gccggcatct | aatgtttgcg | cctgcgtctg | 660 |
| tactagtccg | cggacactgc | tgtaactctc | cttgacctat | atcgatgttc | tagtgtacct | 720 |
| ttattgactt | tgacatattt | ctgtcctttt | aagttcggcg | gcagctcgg | ttgctcaatt | 780 |
| cgtctctgga | ctcttttact | ttgttcctgt | gtggggaag | aaaaaatatt | ttctcctcta | 840 |
| aacaccaaag | atccaaagat | aaaattcctt | tgatggaggg | aaaacagccc | ccttcccca | 900 |
| tttttgatttt | ctttcgagcg | aaacatgttc | acagccaacg | ggagggtaa | aggattcccc | 960 |
| cccccgccca | gataggctcg | aattaaacaa | aggagggaga | gttgacagaa | accaaccaag | 1020 |
| gggaggatta | tggtgacgtc | tggggctaga | tgtgaagaga | tcaaggaaga | aaccagcaga | 1080 |
| gaagacattg | gtcaggcttg | tcatgagcag | tgtgatggtg | cctatacatt | ttcatgctgg | 1140 |
| gcagaaacat | ctttccacat | ttgacctcca | gttccttgat | gtaatcatat | gtttggggtt | 1200 |
| ccttgagaaa | gtgtggggag | agtcttcata | tattagctca | aggaacatgt | atagaatagg | 1260 |
| tagagagaat | ttagcagcat | tagggaaaca | gacaaagaaa | acgtcaggca | aactgtgggc | 1320 |
| tgccctctca | atccttgagt | tcccagtaat | ttagagacta | taacagtcac | gagatcgttc | 1380 |
| tctgctcaca | gataacaaga | gcaggggta | agtgtaacaa | aatcttcaga | gtaaggaggg | 1440 |
| ccatagtggt | ctaaaacact | ccttatagtt | ggagtgcgtc | gctttgcagg | gttcatttga | 1500 |
| aaatctgaag | gtttccttgc | gagacgctag | attccatacc | attctcacat | atgcttttgt | 1560 |
| gcctgtggag | tttcagacct | agataagaga | atgattgaat | atttcactaa | cgttctgtta | 1620 |
| ccagaagagc | gtgagaggcg | tgtgattcat | ttgtgggcgt | aaatcgctga | ctaccatttg | 1680 |
| attcgatgac | atttgatttc | tgtttgtaaa | gatgatgctg | tgtttcggat | gttgtgctaa | 1740 |
| gcaccatggt | aaatgcaaga | agttaatcat | ctgggaaagg | gccagattgc | ctcccagaag | 1800 |
| actgggactt | aagggcacac | atgaagttcc | ctgagaagtc | aatctagaga | gtgttagaag | 1860 |
| ttgtcagaga | gggaccttct | ctagtgagtg | ctaaacaccc | acagacaatt | atatgatcga | 1920 |
| tgccttgaga | actggtggta | agttattata | agcattgaag | ggcaaggcac | tagaaatgta | 1980 |
| agaactatgc | tttcatggaa | cacacacaca | gacacacaca | cagatacccca | catgcacaca | 2040 |
| cacacacatg | cacacgcaca | cagacacaca | catacacaca | gacatacata | cacacacagc | 2100 |
| acatacacac | atacatacat | gcacacacag | agagcaagca | cacacagaga | gagtcataca | 2160 |
| cacacacaca | caaacacaca | aacacacaaa | cacacaagca | gacacaaaca | gacacagcaa | 2220 |
| aaaggatcct | gaaggagtga | aagtcatttt | ctgccaactc | acatgtgcag | tctaactgtg | 2280 |
| cattctagaa | gtgccagtcc | taagaatggt | gatatttact | cacacctttt | tagaaatatt | 2340 |
| tgtagctgtc | cagcatttag | gacacaccac | tccgcctcca | cacatgaaag | tatactttca | 2400 |
| gagaagtatt | attttgtgag | atgaatcata | agactcagaa | tcagtcatgt | taaattattc | 2460 |

```
accgaatgtc ataggactga taactggcac acacacgatt agcatcttct gatggcgggg    2520
ttcagtttac cgggtcacgc tgcactgggg aagattcgag gatttatgga aaaagtcaac    2580
agaacaagaa ttggagcagc cggaaagtat ttgctgcgaa ctctgtactt aggacttagc    2640
tttgagcaat agccccgaaa ggttttagca ctgtttgcgg tcagcacaca aaccgtggtt    2700
caaagctcct ccttatctct tcctgcggca tttgccgtct ctggttctgc acacggtttc    2760
tcacccgctc ccacacacct acactaagcc ctgtaagctg gagctattcc agtatccatc    2820
ccctctgtgt gattctggag ataggaagca atacaccagt gcctgtcaac ttcttcgatc    2880
tgcaaatcag ggtgtttggc ccacaacatt cctgggagta aaaagcaagc ttggattaca    2940
ttaactcacc acatactaaa ccagaaccag tagggtaaac caatctctgt ctctgtctct    3000
ctgtctctct ccctcactcc ctcttgcttt ctctctagga gtcagtatgt gtgaacttag    3060
cttttaaagc atttttttct ttaattttac ttcatccaca ttacgaaatt ttatgtggat    3120
ttctcacttc ctgtcagcga tgccttcacc cacgtggctt tgttagatta cacattgcag    3180
tagtttaatt ggtctcatct cttttttgaca gcagcagaga cattttcaaa ggacagagat    3240 gattttttt ttttaccagc tcctctttga ggtccttcat gaagcgggaa cacgaggtcc    3300
ttaagagaca gcctgtgcca gcctcatcaa aaacactgcc cccattaggt tgccagtagg    3360
taaagccctt agcatcatag tcttagccac ctgagttcca tctctggagc tctcagaaga    3420
gcggagagag agatcagact ctacagggtt gcctctgact gccactgagg gtctgccaac    3480
tttttgtgtc atggggagtt gaacccagag cctcacacaa actcggcgag ccacgatccg    3540
ctgagtcctg ccatttctga acactgtgtc tcacatattg cctttcttct cattcctgaa    3600
ctacgctgtt ctctccatta atgggtctct cgctgtcttt tacaattcct cgaggtaaaa    3660
ggcaagcctt gctattcggc ctacctacca acttttcttt gggtctcttg gaaatgtgac    3720
ttcctctaaa aataccctcac cggtagaaag acactaggag ctgttttcct tccacatagc    3780
aggacatcca tcagagaact tggatacagt ggatgcagtc atttttccac cagatgagat    3840
gtggtctcag tcagtaatgc tgacactcat tgctgacact tcccttcagt gaacaacatc    3900
tcatatgcgg acttcacact ttttgttgaa tgaatcatgg aaccccaac tgttgagttc    3960 tacttggtgg cggccctatt ctgagtgacc ctcttactag tttatctaac cctcgtttat    4020
taaaaaggat attaattttc gtaactataa ttttatatg ttgggagtaa aaccattttg    4080
agtgttttgt ccaatgtcac ctgaccgaca gtttgaatag tcggggtag agcctttcgt    4140 atactaaagt ccagtttgtt taaccatatt gcttcagtgg ggtttcatgg gctcaggaag    4200
taacgaatga accagacata gagctatgaa aggtatgtgg tgcgagctca gcccttgcga    4260
caaagctttg agcaacagcc cgcgtgggct tagggttgtt tgcagttggt gttagagacc    4320
tcacacaaag tcatgtggca gataacccgg aggcaaaatt caaacccagt cgccatatgc    4380
tcatgtttaa cggtgaccct gtgcaccttt ctgatcacat gctttggaat tgcaaagatc    4440
tccccacaag gcagagtgca gagagaatta aggatgacat aaccctgtgg gctgggctga    4500
tctgggctgc tcctcttggc ttaggtgtag aagcatagca gtgaattggt gactgatata    4560
acgtgtattt attatctata gttttgtgtg tgtgtgtgtg tgtgtgtgtg tgtgtgtgtg    4620
tgtgtgtgtg tatgatcata tttacacatg attcatctag cctttatgaa aggatgatga    4680
aaccagacat ttagccttgc ggttacatgc atactagcaa gaaactcgat ataggatctt    4740
taaaggtagg aagatctcag agtggtcaag gagaggtgta gcacacctgt aatccaggac    4800
```

```
ccaggagata ggaaaatcag gaactcaaag ccaactgctc acaaaccgac catgcaaacg     4860
attgaccaaa ctaaaatgga gactcttatt tcactttaaa cccttgtcac tggataaata     4920
cattcattat ctactcagca agtgttgggt cctgtctcaa cacttgacgt gctatgcata     4980
gtgtaaaacg tactcagtgt acttagacca tttattgtta ttttatccaa tgagtaggga     5040
tgagaggaga gggagacaga gacagagaca gagacagaga cagagagaga cagagacaga     5100
gagagacaga gagagacaga gagagacaga gagagagaca gagaggagag agaggagaga     5160
gatagagagg acagagaaga cagagagaag agcagtagac agacacacag agagagagag     5220
agagagagag agagagagag agagagagag agagagagag agagacagag agagacagag     5280
agagagacag atagacacac agagagagaa agagaggag agagagacac agagagagag      5340
gtagacagac agacacacat acacacagac agacagacag acagacacac acacacagag     5400
agagagagag agagagagag agagagagag agagagagag agagagagag agagagagag     5460
gtctgatttc ccttgcaatc tagaaagtta acgttaaact ctggcctgtc attgctttgt     5520
tctattttga gaacaggaag aagtgcaggt atggtctgat aataaggcct tattgtgtgt     5580
gtttcttggt ttctattatt aatatgttat gaaaatcttt ccattacatc aactattaat     5640
ctacaaaatc ggtttgatag cggcattgct ctccatttaa tgaatacact atatttattt     5700
ctggtgtaag tcattttgtt tttataatca catctttaaa gtagctactc acaggctatg     5760
cagatgactc agctgttaag ggccctttct gctcttctag aggccctagg ttcaattccc     5820
agcccacagg gcagctcata accacctgtg actccagttc cgagggatcc aatgccctct     5880
tctgacctct gcagcttcag atggcaaaca tacttaaggg attagttaa acaacttttt     5940 tttttcgaat tggcaaggat catatgattt tgtaatggcg ccggaaccaa tgaaatgcta     6000
gcttagtgtg gttaatgatc taccggtatt ggttagagaa gtatattatc gcagtttct     6060 ctgcacacag accacctttc ctgtccagat ctgagcttgg cgagattttc aggagctaa      6119
```

<210> SEQ ID NO 9  
<211> LENGTH: 6395  
<212> TYPE: DNA  
<213> ORGANISM: Artificial Sequence  
<220> FEATURE:  
<223> OTHER INFORMATION: plasmid pMSCV-F-del Casp9.IRES.GFP  
<220> FEATURE:  
<221> NAME/KEY: misc_feature  
<222> LOCATION: (5986)..(5989)  
<223> OTHER INFORMATION: n is a, c, g, or t

<400> SEQUENCE: 9

```
atgctcgagg gagtgcaggt ggagactatc tccccaggag acgggcgcac cttccccaag       60
cgcggccaga cctgcgtggt gcactacacc gggatgcttg aagatggaaa gaaagttgat      120
tcctcccggg acagaaacaa gcccttttaag tttatgctag gcaagcagga ggtgatccga     180
ggctgggaag aaggggttgc ccagatgagt gtgggtcaga gagccaaaact gactatatct     240 ccagattatg cctatggtgc cactgggcac ccaggcatca tcccaccaca tgccactctc     300
gtcttcgatg tggagcttct aaaactggaa tctggcggtg gatccggagt cgacggattt     360
ggtgatgtcg gtgctcttga gagtttgagg ggaaatgcag atttggctta catcctgagc     420
atggagccct gtggccactg cctcattatc aacaatgtga acttctgccg tgagtccggg     480
ctccgcaccc gcactggctc caacatcgac tgtgagaagt tgcggcgtcg cttctcctcg     540
ctgcatttca tggtggaggt gaagggcgac ctgactgcca gaaaatggt gctggctttg     600 ctggagctgg cgcggcagga ccacggtgct ctggactgct gcgtggtggt cattctctct     660
```

```
cacggctgtc aggccagcca cctgcagttc caggggctg tctacggcac agatggatgc    720
cctgtgtcgg tcgagaagat tgtgaacatc ttcaatggga ccagctgccc cagcctggga    780
gggaagccca agctcttttt catccaggcc tgtggtgggg agcagaaaga ccatgggttt    840
gaggtggcct ccacttcccc tgaagacgag tcccctggac gtaacccga gccagatgcc     900
accccgttcc aggaaggttt gaggaccttc gaccagctgg acgccatatc tagtttgccc    960
acacccagtg acatctttgt gtcctactct actttcccag ttttgtttc ctggagggac    1020
cccaagagtg gctcctggta cgttgagacc ctggacgaca tctttgagca gtgggctcac    1080
tctgaagacc tgcagtccct cctgcttagg gtcgctaatg ctgtttcggt gaaagggatt    1140
tataaacaga tgcctggttg ctttaatttc ctccggaaaa aacttttctt taaaacatca    1200
gtcgactatc cgtacgacgt accagactac gcactcgact aagaattcat cgagcgggat    1260
caattccgcc ccccctaa cgttactggc cgaagccgct tggaataagg ccggtgtgcg      1320
tttgtctata tgttatttc caccatattg ccgtcttttg caatgtgag ggcccggaaa     1380
cctggccctg tcttcttgac gagcattcct aggggtcttt cccctctcgc caaaggaatg   1440
caaggtctgt tgaatgtcgt gaaggaagca gttcctctgg aagcttcttg aagacaaaca   1500
acgtctgtag cgacccttg caggcagcgg aaccccccac ctggcgacag gtgcctctgc    1560
ggccaaaagc cacgtgtata agatacacct gcaaaggcgg cacaacccca gtgccacgtt   1620
gtgagttgga tagttgtgga aagagtcaaa tggctctcct caagcgtatt caacaagggg   1680
ctgaaggatg cccagaaggt acccattgt atgggatctg atctggggcc tcggtgcaca    1740
tgctttacat gtgtttagtc gaggttaaaa aacgtctagg ccccccgaac cacggggacg   1800
tggttttcct ttgaaaaaca cgataatacc atggtgagca agggcgagga gctgttcacc   1860
ggggtggtgc ccatcctggt cgagctggac ggcgacgtaa acggccacaa gttcagcgtg   1920
tccggcgagg gcgagggcga tgccacctac ggcaagctga ccctgaagtt catctgcacc   1980
accggcaagc tgcccgtgcc ctggcccacc ctcgtgacca ccctgaccta cggcgtgcag   2040
tgcttcagcc gctaccccga ccacatgaag cagcacgact tcttcaagtc cgccatgccc   2100
gaaggctacg tccaggagcg caccatcttc ttcaaggacg acggcaacta caagacccgc   2160
gccgaggtga agttcgaggg cgacaccctg gtgaaccgca tcgagctgaa gggcatcgac   2220
ttcaaggagg acggcaacat cctggggcac aagctggagt acaactacaa cagccacaac   2280
gtctatatca tggccgacaa gcagaagaac ggcatcaagg tgaacttcaa gatccgccac   2340
aacatcgagg acggcagcgt gcagctcgcc gaccactacc agcagaacac ccccatcggc   2400
gacggccccg tgctgctgcc cgacaaccac tacctgagca cccagtccgc cctgagcaaa   2460
gaccccaacg agaagcgcga tcacatggtc ctgctggagt tcgtgaccgc cgccgggatc   2520
actctcggca tggacgagct gtacaagtaa agcggccgcg actctagagt cgacctgcag   2580
gcatgcaagc ttcaggtagc cggctaacgt taacaaccgg tacctctaga actatagcta   2640
gcatgcgcaa atttaaagcg ctgatatcga taaaataaaa gattttattt agtctccaga   2700
aaaaggggg aatgaaagac cccacctgta ggtttggcaa gctagcttaa gtaacgccat    2760
tttgcaaggc atggaaaata cataactgag aatagagaag ttcagatcaa ggttaggaac   2820
agagagacag cagaatatgg gccaaacagg atatctgtgg taagcagttc ctgccccggc   2880
tcagggccaa gaacagatgg tccccagatg cggtcccgcc ctcagcagtt tctagagaac   2940
catcagatgt ttccagggtg ccccaaggac ctgaaaatga ccctgtgcct tatttgaact   3000
```

```
aaccaatcag ttcgcttctc gcttctgttc gcgcgcttct gctccccgag ctcaataaaa   3060
gagcccacaa cccctcactc ggcgcgccag tcctccgata gactgcgtcg cccgggtacc   3120
cgtgtatcca ataaaccctc ttgcagttgc atccgacttg tggtctcgct gttccttggg   3180
agggtctcct ctgagtgatt gactacccgt cagcggggt cttcatggg taacagtttc      3240 ttgaagttgg agaacaacat tctgagggta ggagtcgaat attaagtaat cctgactcaa   3300
ttagccactg ttttgaatcc acatactcca atactccgta aatagttcat tatgacagc     3360 gcagaaagag ctggggagaa ttgtgaaatt gttatccgct cacaattcca cacaacatac   3420
gagccggaag cataaagtgt aaagcctggg gtgcctaatg agtgagctaa ctcacattaa   3480
ttgcgttgcg ctcactgccc gctttccagt cgggaaacct gtcgtgccag ctgcattaat   3540
gaatcggcca acgcgcgggg agaggcggtt tgcgtattgg cgctcttcc gcttcctcgc    3600 tcactgactc gctgcgctcg gtcgttcggc tgcggcgagc ggtatcagct cactcaaagg   3660
cggtaatacg gttatccaca gaatcagggg ataacgcagg aaagaacatg tgagcaaaag   3720
gccagcaaaa ggccaggaac cgtaaaaagg ccgcgttgct ggcgtttttc cataggctcc   3780
gcccccctga cgagcatcac aaaaatcgac gctcaagtca gaggtggcga acccgacag    3840 gactataaag ataccaggcg tttcccctg gaagctccct cgtgcgctct cctgttccga     3900
ccctgccgct taccggatac ctgtccgcct ttctcccttc gggaagcgtg gcgctttctc   3960
atagctcacg ctgtaggtat ctcagttcgg tgtaggtcgt tcgctccaag ctgggctgtg   4020
tgcacgaacc ccccgttcag cccgaccgct gcgccttatc cggtaactat cgtcttgagt   4080
ccaacccggt aagacacgac ttatcgccac tggcagcagc cactggtaac aggattagca   4140
gagcgaggta tgtaggcggt gctacagagt tcttgaagtg gtggcctaac tacggctaca   4200
ctagaaggac agtatttggt atctgcgctc tgctgaagcc agttaccttc ggaaaaagag   4260
ttggtagctc ttgatccggc aaacaaacca ccgctggtag cggtggtttt tttgtttgca   4320
agcagcagat tacgcgcaga aaaaaggat ctcaagaaga tcctttgatc ttttctacgg     4380
ggtctgacgc tcagtggaac gaaaactcac gttaagggat tttggtcatg agattatcaa   4440
aaaggatctt cacctagatc cttttaaatt aaaaatgaag ttttaaatca atctaaagta   4500
tatatgagta aacttggtct gacagttacc aatgcttaat cagtgaggca cctatctcag   4560
cgatctgtct atttcgttca tccatagttg cctgactccc cgtcgtgtag ataactacga   4620
tacgggaggg cttaccatct ggccccagtg ctgcaatgat accgcgagac ccacgctcac   4680
cggctccaga tttatcagca ataaaccagc cagccggaag ggccgagcgc agaagtggtc   4740
ctgcaacttt atccgcctcc atccagtcta ttaattgttg ccgggaagct agagtaagta   4800
gttcgccagt taatagtttg cgcaacgttg ttgccattgc tacaggcatc gtggtgtcac   4860
gctcgtcgtt tggtatggct tcattcagct ccggttccca acgatcaagg cgagttacat   4920 gatccccat gttgtgcaaa aaagcggtta gctccttcgg tcctccgatc gttgtcagaa      4980
gtaagttggc cgcagtgtta tcactcatgg ttatggcagc actgcataat tctcttactg   5040
tcatgccatc cgtaagatgc ttttctgtga ctggtgagta ctcaaccaag tcattctgag   5100
aatagtgtat gcggcgaccg agttgctctt gcccggcgtc aatacgggat aataccgcgc   5160
cacatagcag aactttaaaa gtgctcatca ttggaaaacg ttcttcgggg cgaaaactct   5220
caaggatctt accgctgttg agatccagtt cgatgtaacc cactcgtgca cccaactgat   5280
cttcagcatc ttttactttc accagcgttt ctgggtgagc aaaaacagga aggcaaaatg   5340
ccgcaaaaaa gggaataagg gcgacacgga aatgttgaat actcatactc ttccttttc     5400
```

-continued

```
aatattattg aagcatttat cagggttatt gtctcatgag cggatacata tttgaatgta      5460
tttagaaaaa taaacaaata ggggttccgc gcacatttcc ccgaaaagtg ccacctgacg      5520
tctaagaaac cattattatc atgacattaa cctataaaaa taggcgtatc acgaggccct      5580
ttcgtctcgc gcgtttcggt gatgacggtg aaaacctctg acacatgcag ctcccggaga      5640
cggtcacagc ttgtctgtaa gcggatgccg ggagcagaca gcccgtcag ggcgcgtcag       5700 cgggtgttgg cgggtgtcgg ggctggctta actatgcggc atcagagcag attgtactga      5760
gagtgcacca tatgcggtgt gaaataccgc acagatgcgt aaggagaaaa taccgcatca      5820
ggcgccattc gccattcagg ctgcgcaact gttgggaagg gcgatcggtg cgggcctctt      5880
cgctattacg ccagctggcg aaaggggat gtgctgcaag gcgattaagt tgggtaacgc       5940
cagggttttc ccagtcacga cgttgtaaaa cgacggccag tgccannnnc gctctccctt      6000
atgcgactcc tgcattagga agcagcccag tagtaggttg aggccgttga gcaccgccgc      6060
cgcaaggaat ggtgcatgca aggagatggc gcccaacagt cccccggcca cggggcctgc      6120
caccataccc acgccgaaac aagcgctcat gagcccgaag tggcgagccc gatcttcccc      6180
atcggtgatg tcggcgatat aggcgccagc aaccgcacct gtggcgccgg tgatgccggc      6240
cacgatgcgt ccggcgtaga ggcgattagt ccaatttgtt aaagacagga tatcagtggt      6300
ccaggctcta gttttgactc aacaatatca ccagctgaag cctatagagt acgagccata      6360
gataaaataa aagattttat ttagtctcca gaaaa                                6395
```

<210> SEQ ID NO 10
<211> LENGTH: 413
<212> TYPE: PRT
<213> ORGANISM: Artificial Sequence
<220> FEATURE:
<223> OTHER INFORMATION: iCasp9 protein

<400> SEQUENCE: 10

```
Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
```

```
                  180                 185                 190
Ala Lys Lys Met Val Leu Ala Leu Leu Glu Leu Ala Arg Gln Asp His
                195                 200                 205

Gly Ala Leu Asp Cys Cys Val Val Ile Leu Ser His Gly Cys Gln
    210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
    290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
    370                 375                 380

Pro Gly Cys Phe Asn Phe Leu Arg Lys Lys Leu Phe Phe Lys Thr Ser
385                 390                 395                 400

Val Asp Tyr Pro Tyr Asp Val Pro Asp Tyr Ala Leu Asp
                405                 410

<210> SEQ ID NO 11
<211> LENGTH: 239
<212> TYPE: PRT
<213> ORGANISM: Aequorea victoria

<400> SEQUENCE: 11

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140
```

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 12
<211> LENGTH: 220
<212> TYPE: PRT
<213> ORGANISM: Escherichia coli

<400> SEQUENCE: 12

Met Ser Thr Phe Lys Val Leu Cys Gly Ala Val Leu Ser Arg Ile
1               5                   10                  15

Asp Ala Gly Gln Glu Gln Leu Gly Arg Arg Ile His Tyr Ser Gln Asn
                20                  25                  30

Asp Leu Val Glu Tyr Ser Pro Val Thr Glu Lys His Leu Thr Asp Gly
            35                  40                  45

Met Thr Val Arg Glu Leu Cys Ser Ala Ala Ile Thr Met Ser Asp Asn
        50                  55                  60

Thr Ala Ala Asn Leu Leu Leu Thr Thr Ile Gly Gly Pro Lys Glu Leu
65                  70                  75                  80

Thr Ala Phe Leu His Asn Met Gly Asp His Val Thr Arg Leu Asp Arg
                85                  90                  95

Trp Glu Pro Glu Leu Asn Glu Ala Ile Pro Asn Asp Glu Arg Asp Thr
                100                 105                 110

Thr Met Pro Val Ala Met Ala Thr Thr Leu Arg Lys Leu Leu Thr Gly
        115                 120                 125

Glu Leu Leu Thr Leu Ala Ser Arg Gln Gln Leu Ile Asp Trp Met Glu
130                 135                 140

Ala Asp Lys Val Ala Gly Pro Leu Leu Arg Ser Ala Leu Pro Ala Gly
145                 150                 155                 160

Trp Phe Ile Ala Asp Lys Ser Gly Ala Gly Glu Arg Gly Ser Arg Gly
                165                 170                 175

Ile Ile Ala Ala Leu Gly Pro Asp Gly Lys Pro Ser Arg Ile Val Val
            180                 185                 190

Ile Tyr Thr Thr Gly Ser Gln Ala Thr Met Asp Glu Arg Asn Arg Gln
        195                 200                 205

Ile Ala Glu Ile Gly Ala Ser Leu Ile Lys His Trp
210                 215                 220

<210> SEQ ID NO 13
<211> LENGTH: 23
<212> TYPE: PRT
<213> ORGANISM: Escherichia coli

<400> SEQUENCE: 13

Pro Phe Ala Ile Gln Ala Gln Leu Leu Gly Arg Ala Ile Gly Ala
1               5                   10                  15
```

Gly Leu Phe Ala Ile Thr Pro
        20

<210> SEQ ID NO 14
<211> LENGTH: 11
<212> TYPE: DNA
<213> ORGANISM: Artificial Sequence
<220> FEATURE:
<223> OTHER INFORMATION: Linker

<400> SEQUENCE: 14
attacgccac c                                                          11

<210> SEQ ID NO 15
<211> LENGTH: 13
<212> TYPE: DNA
<213> ORGANISM: Murine leukemia virus

<400> SEQUENCE: 15
cgtctgtact agt                                                        13

<210> SEQ ID NO 16
<211> LENGTH: 13
<212> TYPE: DNA
<213> ORGANISM: Homo sapiens

<400> SEQUENCE: 16
ccgcggacac tgc                                                        13

<210> SEQ ID NO 17
<211> LENGTH: 177
<212> TYPE: DNA
<213> ORGANISM: Artificial Sequence
<220> FEATURE:
<223> OTHER INFORMATION: Enhancer

<400> SEQUENCE: 17
gtgtaccttt attgactttg acatatttct gtccttttaa gttcggcggg cagctcggtt      60
gctcaattcg tctctggact cttttacttt gttcctgtgt gggggaagaa aaatattt      120 ctcctctaaa caccaaagat ccaaagataa aattcctttg atggagggaa aacagcc       177

<210> SEQ ID NO 18
<211> LENGTH: 237
<212> TYPE: DNA
<213> ORGANISM: Artificial Sequence
<220> FEATURE:
<223> OTHER INFORMATION: Enhancer

<400> SEQUENCE: 18
cacacacgat tagcatcttc tgatggcggg gttcagttta ccgggtcacg ctgcactggg      60
gaagattcga ggatttatgg aaaaagtcaa cagaacaaga attggagcag ccggaaagta    120
tttgctgcga actctgtact taggacttag ctttgagcaa tagccccgaa aggttttagc    180
actgtttgcg gtcagcacac aaaccgtggt tcaaagctcc tccttatctc ttcctgc       237

<210> SEQ ID NO 19
<211> LENGTH: 346
<212> TYPE: DNA
<213> ORGANISM: Artificial Sequence
<220> FEATURE:
<223> OTHER INFORMATION: enhancer

<400> SEQUENCE: 19

```
atgtcacctg accgacagtt tgaatagtcg ggggtagagc ctttcgtata ctaaagtcca      60
gtttgtttaa ccatattgct tcagtggggt ttcatgggct caggaagtaa cgaatgaacc     120
agacatagag ctatgaaagg tatgtggtgc gagctcagcc cttgcgacaa agctttgagc     180
aacagcccgc gtgggcttag ggttgtttgc agttggtgtt agagacctca cacaaagtca     240
tgtggcagat aacccggagg caaaattcaa acccagtcgc catatgctca tgtttaacgg     300
tgaccctgtg caccttttctg atcacatgct ttggaattgc aaagat                   346

<210> SEQ ID NO 20
<211> LENGTH: 15
<212> TYPE: DNA
<213> ORGANISM: Homo sapiens

<400> SEQUENCE: 20
ttctgacctc tgcag                                                       15

<210> SEQ ID NO 21
<211> LENGTH: 194
<212> TYPE: DNA
<213> ORGANISM: Artificial Sequence
<220> FEATURE:
<223> OTHER INFORMATION: Alb 123 promoter

<400> SEQUENCE: 21
gcttcagatg gcaaacatac ttaagggatt tagttaaaca actttttttt ttcgaattgg      60
caaggatcat atgattttgt aatggcgccg gaaccaatga aatgctagct tagtgtggtt     120
aatgatctac cggtattggt tagagaagta tattatcgcg agtttctctg cacacagacc     180
acctttcctg tcca                                                       194

<210> SEQ ID NO 22
<211> LENGTH: 15
<212> TYPE: DNA
<213> ORGANISM: Homo sapiens

<400> SEQUENCE: 22
ggttaatgat ctacc                                                       15

<210> SEQ ID NO 23
<211> LENGTH: 1242
<212> TYPE: DNA
<213> ORGANISM: Artificial Sequence
<220> FEATURE:
<223> OTHER INFORMATION: DNA encoding iCas9

<400> SEQUENCE: 23
atgctcgagg gagtgcaggt ggagactatc tccccaggag acgggcgcac cttccccaag      60
cgcggccaga cctgcgtggt gcactacacc gggatgcttg aagatggaaa gaaagttgat     120
tcctcccggg acagaaacaa gcccttttaag tttatgctag gcaagcagga ggtgatccga     180
ggctgggaag aaggggttgc ccagatgagt gtgggtcaga gagccaaact gactatatct     240
ccagattatg cctatggtgc cactgggcac ccaggcatca tcccaccaca tgccactctc     300
gtcttcgatg tggagcttct aaaactggaa tctggcggtg atccggagt cgacggatttt     360 ggtgatgtcg gtgctcttga gagtttgagg ggaaatgcag atttggctta catcctgagc     420
atggagccct gtggccactg cctcattatc aacaatgtga acttctgccg tgagtccggg     480
ctccgcaccc gcactggctc caacatcgac tgtgagaagt gcggcgtcg cttctcctcg     540 ctgcatttca tggtggaggt gaagggcgac ctgactgcca agaaaatggt gctggctttg     600
```

```
ctggagctgg cgcggcagga ccacggtgct ctggactgct gcgtggtggt cattctctct    660
cacggctgtc aggccagcca cctgcagttc caggggctg tctacggcac agatggatgc    720
cctgtgtcgg tcgagaagat tgtgaacatc ttcaatggga ccagctgccc cagcctggga    780
gggaagccca agctcttttt catccaggcc tgtggtgggg agcagaaaga ccatgggttt    840
gaggtggcct ccacttcccc tgaagacgag tcccctggca gtaacccga  gccagatgcc    900 accccgttcc aggaaggttt gaggaccttc gaccagctgg acgccatatc tagtttgccc    960
acacccagtg acatctttgt gtcctactct actttcccag gttttgtttc ctggagggac   1020
cccaagagtg gctcctggta cgttgagacc ctggacgaca tctttgagca gtgggctcac   1080
tctgaagacc tgcagtccct cctgcttagg gtcgctaatg ctgtttcggt gaaagggatt   1140
tataaacaga tgcctggttg ctttaatttc ctccggaaaa aacttttctt taaaacatca   1200
gtcgactatc cgtacgacgt accagactac gcactcgact aa                      1242
```

<210> SEQ ID NO 24
<211> LENGTH: 586
<212> TYPE: DNA
<213> ORGANISM: Artificial Sequence
<220> FEATURE:
<223> OTHER INFORMATION: IRES

<400> SEQUENCE: 24

```
attcatcgag cgggatcaat tccgccccc  ccctaacgtt actggccgaa gccgcttgga     60
ataaggccgg tgtgcgtttg tctatatgtt attttccacc atattgccgt cttttggcaa    120
tgtgagggcc cggaaacctg gccctgtctt cttgacgagc attcctaggg gtctttcccc    180
tctcgccaaa ggaatgcaag gtctgttgaa tgtcgtgaag gaagcagttc ctctggaagc    240
ttcttgaaga caaacaacgt ctgtagcgac cctttgcagg cagcggaacc ccccacctgg    300
cgacaggtgc ctctgcggcc aaaagccacg tgtataagat acacctgcaa aggcggcaca    360
accccagtgc cacgttgtga gttggatagt gtggaaaga  gtcaaatggc tctcctcaag    420
cgtattcaac aaggggctga aggatgccca gaaggtaccc cattgtatgg gatctgatct    480
ggggcctcgg tgcacatgct ttacatgtgt ttagtcgagg ttaaaaaacg tctaggcccc    540
ccgaaccacg gggacgtggt tttcctttga aaaacacgat aatacc                   586
```

<210> SEQ ID NO 25
<211> LENGTH: 720
<212> TYPE: DNA
<213> ORGANISM: Aequorea victoria

<400> SEQUENCE: 25

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 26
<211> LENGTH: 533
<212> TYPE: DNA
<213> ORGANISM: Artificial Sequence
<220> FEATURE:
<223> OTHER INFORMATION: DNA encoding a polyA tail

<400> SEQUENCE: 26

```
tagagtcgac ctgcaggcat gcaagcttca ggtagccggc taacgttaac aaccggtacc     60
tctagaacta tagctagcat gcgcaaattt aaagcgctga tatcgataaa ataaaagatt    120
ttatttagtc tccagaaaaa gggggggaatg aaagacccca cctgtaggtt tggcaagcta    180
gcttaagtaa cgccatttg caaggcatgg aaaatacata actgagaata gagaagttca     240
gatcaaggtt aggaacagag agacagcaga atatgggcca acaggatat ctgtggtaag     300 cagttcctgc cccggctcag ggccaagaac agatggtccc cagatgcggt cccgccctca    360
gcagtttcta gagaaccatc agatgtttcc agggtgcccc aaggacctga aaatgaccct    420
gtgccttatt tgaactaacc aatcagttcg cttctcgctt ctgttcgcgc gcttctgctc    480
cccgagctca ataaaagagc ccacaacccc tcactcggcg cgccagtcct ccg           533
```

<210> SEQ ID NO 27
<211> LENGTH: 23
<212> TYPE: DNA
<213> ORGANISM: Escherichia coli

<400> SEQUENCE: 27

```
aattgttatc cgctcacaat tcc                                              23
```

<210> SEQ ID NO 28
<211> LENGTH: 683
<212> TYPE: DNA
<213> ORGANISM: Artificial Sequence
<220> FEATURE:
<223> OTHER INFORMATION: ColE1 origin

<400> SEQUENCE: 28

```
ggccgcgttg ctggcgtttt tccataggct ccgcccccct gacgagcatc acaaaaatcg     60
acgctcaagt cagaggtggc gaaacccgac aggactataa agataccagg cgtttccccc    120
tggaagctcc ctcgtgcgct ctcctgttcc gaccctgccg cttaccggat acctgtccgc    180
ctttctccct cgggaagcg tggcgctttc tcatagctca cgctgtaggt atctcagttc     240
ggtgtaggtc gttcgctcca agctgggctg tgtgcacgaa ccccccgttc agcccgaccg    300
ctgcgcctta ccggtaact atcgtcttga gtccaacccg gtaagacacg acttatcgcc    360
actggcagca gccactggta acaggattag cagagcgagg tatgtaggcg gtgctacaga    420
gttcttgaag tggtggccta actacggcta cactagaagg acagtatttg gtatctgcgc    480
tctgctgaag ccagttacct tcggaaaaag agttggtagc tcttgatccg gcaaacaaac    540
caccgctggt agcggtggtt tttttgtttg caagcagcag attacgcgca gaaaaaaagg    600
atctcaagaa gatcctttga tcttttctac ggggtctgac gctcagtgga acgaaaactc    660
acgttaaggg attttggtca tga                                             683
```

<210> SEQ ID NO 29
<211> LENGTH: 660
<212> TYPE: DNA
<213> ORGANISM: Escherichia coli

<400> SEQUENCE: 29

```
ccaatgctta atcagtgagg cacctatctc agcgatctgt ctatttcgtt catccatagt        60
tgcctgactc cccgtcgtgt agataactac gatacgggag ggcttaccat ctggccccag       120
tgctgcaatg ataccgcgag acccacgctc accggctcca gatttatcag caataaacca       180
gccagccgga agggccgagc gcagaagtgg tcctgcaact ttatccgcct ccatccagtc       240
tattaattgt tgccgggaag ctagagtaag tagttcgcca gttaatagtt tgcgcaacgt       300
tgttgccatt gctacaggca tcgtggtgtc acgctcgtcg tttggtatgg cttcattcag       360
ctccggttcc caacgatcaa ggcgagttac atgatccccc atgttgtgca aaaaagcggt       420
tagctccttc ggtcctccga tcgttgtcag aagtaagttg gccgcagtgt tatcactcat       480
ggttatggca gcactgcata attctcttac tgtcatgcca tccgtaagat gcttttctgt       540
gactggtgag tactcaacca agtcattctg agaatagtgt atgcggcgac cgagttgctc       600
ttgcccggcg tcaatacggg ataataccgc gccacatagc agaactttaa aagtgctcat       660
```

<210> SEQ ID NO 30
<211> LENGTH: 69
<212> TYPE: DNA
<213> ORGANISM: Escherichia coli

<400> SEQUENCE: 30

```
ccattcgcca ttcaggctgc gcaactgttg ggaagggcga tcggtgcggg cctcttcgct        60
attacgcca                                                                69
```

<210> SEQ ID NO 31
<211> LENGTH: 18
<212> TYPE: DNA
<213> ORGANISM: Artificial Sequence
<220> FEATURE:
<223> OTHER INFORMATION: M13-forward

<400> SEQUENCE: 31

```
tgtaaaacga cggccagt                                                      18
```

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32

```
gagggcctat ttcccatgat t                                                  21
```

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33

```
gactatcata tgcttaccgt                                                    20
```

<210> SEQ ID NO 34

```
<211> LENGTH: 35
<212> TYPE: DNA
<213> ORGANISM: Rattus rattus

<400> SEQUENCE: 34
agccgaccaa cctcactatg cactataggt atgag                           35

<210> SEQ ID NO 35
<211> LENGTH: 33
<212> TYPE: DNA
<213> ORGANISM: Rattus rattus

<400> SEQUENCE: 35
tacctcccac ctcttcgtta cccagctact tgc                             33

<210> SEQ ID NO 36
<211> LENGTH: 31
<212> TYPE: DNA
<213> ORGANISM: Artificial Sequence
<220> FEATURE:
<223> OTHER INFORMATION: CRISPR mediated mutation

<400> SEQUENCE: 36
agccgaccaa cctatgcact ataggtatga g                               31

<210> SEQ ID NO 37
<211> LENGTH: 24
<212> TYPE: DNA
<213> ORGANISM: Artificial Sequence
<220> FEATURE:
<223> OTHER INFORMATION: CRISPR mediated mutation

<400> SEQUENCE: 37
agcactatgc actataggta tgag                                       24

<210> SEQ ID NO 38
<211> LENGTH: 30
<212> TYPE: DNA
<213> ORGANISM: Artificial Sequence
<220> FEATURE:
<223> OTHER INFORMATION: CRISPR mediated mutation

<400> SEQUENCE: 38
agccgaccaa ctatgcacta taggtatgag                                 30

<210> SEQ ID NO 39
<211> LENGTH: 36
<212> TYPE: DNA
<213> ORGANISM: Artificial Sequence
<220> FEATURE:
<223> OTHER INFORMATION: CRISPR mediated mutation

<400> SEQUENCE: 39
agccgaccaa ccttcactat gcactatagg tatgag                          36

<210> SEQ ID NO 40
<211> LENGTH: 31
<212> TYPE: DNA
<213> ORGANISM: Artificial Sequence
<220> FEATURE:
<223> OTHER INFORMATION: CRISPR mediated mutation

<400> SEQUENCE: 40
agccgaccaa cctatgcact ataggtatga g                               31
```

```
<210> SEQ ID NO 41
<211> LENGTH: 36
<212> TYPE: DNA
<213> ORGANISM: Artificial Sequence
<220> FEATURE:
<223> OTHER INFORMATION: CRISPR mediated mutation

<400> SEQUENCE: 41
agccgaccaa ccttcactat gcactatagg tatgag                        36

<210> SEQ ID NO 42
<211> LENGTH: 31
<212> TYPE: DNA
<213> ORGANISM: Artificial Sequence
<220> FEATURE:
<223> OTHER INFORMATION: CRISPR mediated mutation

<400> SEQUENCE: 42
agccgaccaa cctatgcact ataggtatga g                             31

<210> SEQ ID NO 43
<211> LENGTH: 30
<212> TYPE: DNA
<213> ORGANISM: Artificial Sequence
<220> FEATURE:
<223> OTHER INFORMATION: CRISPR mediated mutation

<400> SEQUENCE: 43
agccgaccaa ctatgcacta taggtatgag                               30

<210> SEQ ID NO 44
<211> LENGTH: 30
<212> TYPE: DNA
<213> ORGANISM: Artificial Sequence
<220> FEATURE:
<223> OTHER INFORMATION: CRISPR mediated mutation

<400> SEQUENCE: 44
agccgaccaa ctatgcacta taggtatgag                               30

<210> SEQ ID NO 45
<211> LENGTH: 30
<212> TYPE: DNA
<213> ORGANISM: Artificial Sequence
<220> FEATURE:
<223> OTHER INFORMATION: CRISPR mediated mutation

<400> SEQUENCE: 45
agccgaccaa ctatgcacta taggtatgag                               30

<210> SEQ ID NO 46
<211> LENGTH: 26
<212> TYPE: DNA
<213> ORGANISM: Artificial Sequence
<220> FEATURE:
<223> OTHER INFORMATION: CRISPR mediated mutation

<400> SEQUENCE: 46
agccgactat gcactatagg tatgag                                   26

<210> SEQ ID NO 47
<211> LENGTH: 15
<212> TYPE: DNA
<213> ORGANISM: Artificial Sequence
<220> FEATURE:
<223> OTHER INFORMATION: CRISPR mediated mutation
```

```
<400> SEQUENCE: 47
tacctcccta cttgc                                                          15

<210> SEQ ID NO 48
<211> LENGTH: 35
<212> TYPE: DNA
<213> ORGANISM: Artificial Sequence
<220> FEATURE:
<223> OTHER INFORMATION: CRISPR mediated mutation

<400> SEQUENCE: 48
tacctcccag gcctcttcgt tacccagcta cttgc                                    35
```